US012594405B2

(12) United States Patent

Mazzone et al.

(10) Patent No.: US 12,594,405 B2

(45) Date of Patent: Apr. 7, 2026

(54) CATHETER HAVING COMPLIANT BALLOON

(71) Applicant: Otsuka Medical Devices Co., Ltd., Tokyo (JP)

(72) Inventors: James D. Mazzone, San Jose, CA (US); Eric Dailey, San Jose, CA (US); Ryan R. Donovan, Santa Clara, CA (US); Jaime Merino, Mountain View, CA (US); Shruthi R. Thirumalai, San Jose, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 481 days.

(21) Appl. No.: 17/812,884

(22) Filed: Jul. 15, 2022

(65) Prior Publication Data

US 2023/0026169 A1 Jan. 26, 2023

Related U.S. Application Data

(60) Provisional application No. 63/367,119, filed on Jun. 27, 2022, provisional application No. 63/223,517, filed on Jul. 19, 2021.

(51) Int. Cl.
A61M 25/10 (2013.01)
A61N 7/02 (2006.01)
A61N 7/00 (2006.01)

(52) U.S. Cl.
CPC .......... A61M 25/1002 (2013.01); A61N 7/02 (2013.01); A61M 2205/0216 (2013.01); A61N 2007/0026 (2013.01); A61N 2007/003 (2013.01)

(58) Field of Classification Search
CPC .......... A61B 17/00234; A61B 17/3207; A61B 17/3478; A61B 2017/003;
(Continued)

(56) References Cited

U.S. PATENT DOCUMENTS

| | | | |
|---|---|---|---|
| 4,554,925 A | 11/1985 | Young | |
| 4,643,186 A | 2/1987 | Rosen | |

(Continued)

FOREIGN PATENT DOCUMENTS

| | | |
|---|---|---|
| AU | 2011/239363 | 5/2012 |
| CA | 2895995 | 6/2014 |

(Continued)

OTHER PUBLICATIONS

Ahmed, Muneeb et al., "Thermal Ablation Therapy for Hepatocellular Carcinoma," J. Vasc. Interv, Radiol., vol. 13, No. 9 pt. 2, 2002.
(Continued)

*Primary Examiner* — Todd J Scherbel
(74) *Attorney, Agent, or Firm* — Theresa Ann Raymer

(57) ABSTRACT

A catheter comprises a catheter shaft having a fluid channel, an ultrasound transducer and a compliant balloon mounted on the catheter shaft and having an interior in fluid communication with the fluid channel and containing the ultrasound transducer. The compliant balloon includes a balloon wall having a working section radially surrounding the ultrasound transducer. The working section has a predetermined straightness when the working section has a first diameter and when the working section has a second diameter that is at least 2 mm greater than the first diameter. Other embodiments are also described and claimed.

36 Claims, 13 Drawing Sheets

(58) Field of Classification Search
CPC ........... A61B 2017/00309; A61B 2017/00331;
A61B 2017/22065; A61B 2017/22071;
A61M 2025/1004; A61M 25/1002; A61M
2205/0216; A61N 7/02; A61N 2007/0026;
A61N 2007/003
See application file for complete search history.

(56) References Cited

U.S. PATENT DOCUMENTS

| | | | |
|---|---|---|---|
| 4,650,466 A | 3/1987 | Luther |
| 4,709,698 A | 12/1987 | Johnston et al. |
| 4,841,977 A | 6/1989 | Griffith et al. |
| 4,983,169 A | 1/1991 | Furukawa |
| 5,000,185 A | 3/1991 | Yock |
| 5,114,423 A | 5/1992 | Kasprzyk |
| 5,368,591 A | 11/1994 | Lennox |
| 5,391,197 A | 2/1995 | Burdette et al. |
| 5,423,811 A | 6/1995 | Imran et al. |
| 5,447,497 A | 9/1995 | Sogard et al. |
| 5,558,672 A | 9/1996 | Edwards et al. |
| 5,575,788 A | 11/1996 | Baker et al. |
| 5,657,755 A | 8/1997 | Desai |
| 5,685,839 A | 11/1997 | Edwards et al. |
| 5,688,266 A | 11/1997 | Edwards et al. |
| 5,800,482 A | 9/1998 | Pomeranz et al. |
| 6,066,134 A | 5/2000 | Eggers et al. |
| 6,097,985 A | 8/2000 | Kasevich et al. |
| 6,117,101 A | 9/2000 | Diederich et al. |
| 6,254,598 B1 | 7/2001 | Edwards |
| 6,283,989 B1 | 9/2001 | Laufer et al. |
| 6,292,695 B1 | 9/2001 | Webster |
| 6,296,619 B1 | 10/2001 | Brisken et al. |
| 6,383,151 B1 | 5/2002 | Diederich et al. |
| 6,514,249 B1 | 2/2003 | Maguire et al. |
| 6,529,756 B1 | 3/2003 | Phar |
| 6,564,096 B2 | 5/2003 | Mest |
| 6,575,933 B1 | 6/2003 | Wittenberger et al. |
| 6,584,360 B2 | 6/2003 | Francischelli et al. |
| 6,635,054 B2 | 10/2003 | Fjield et al. |
| 6,648,883 B2 | 11/2003 | Francischelli et al. |
| 6,669,655 B1 | 12/2003 | Acker |
| 6,692,490 B1 | 2/2004 | Edwards |
| 6,719,755 B2 | 4/2004 | Sliwa, Jr. et al. |
| 6,763,722 B2 | 7/2004 | Field et al. |
| 6,837,886 B2 | 1/2005 | Collins |
| 6,845,267 B2 | 1/2005 | Harrison et al. |
| 6,954,977 B2 | 10/2005 | Maguire |
| 7,052,695 B2 | 5/2006 | Kalish |
| 7,156,816 B2 | 1/2007 | Schwartz et al. |
| 7,162,303 B2 | 1/2007 | Levin et al. |
| 7,371,231 B2 | 5/2008 | Rioux et al. |
| 7,510,536 B2 | 3/2009 | Foley et al. |
| 7,617,005 B2 | 11/2009 | Demarais et al. |
| 7,621,873 B2 | 11/2009 | Owen et al. |
| 7,653,438 B2 | 1/2010 | Deem et al. |
| 7,717,948 B2 | 5/2010 | Demarais et al. |
| 7,942,871 B2 | 5/2011 | Thapliyal et al. |
| 8,024,050 B2 | 9/2011 | Libbus et al. |
| 8,025,688 B2 | 9/2011 | Diederich et al. |
| 8,137,274 B2 | 3/2012 | Weng et al. |
| 8,333,757 B2 | 12/2012 | Mazzone et al. |
| 8,447,414 B2 | 5/2013 | Johnson et al. |
| 8,480,619 B2 | 7/2013 | Porter |
| 8,483,831 B1 | 7/2013 | Hiavka et al. |
| 8,626,300 B2 | 1/2014 | Demarais et al. |
| 8,702,619 B2 | 4/2014 | Wang |
| 8,774,913 B2 | 7/2014 | Demarais et al. |
| 8,790,281 B2 | 7/2014 | Diederich et al. |
| 8,818,514 B2 | 8/2014 | Zarins et al. |
| 8,845,629 B2 | 9/2014 | Demarais et al. |
| 8,932,289 B2 | 1/2015 | Mayse et al. |
| 9,022,948 B2 | 5/2015 | Wang |
| 9,023,037 B2 | 5/2015 | Zarins et al. |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,162,040 B2 | 10/2015 | Vo et al. |
| 9,186,198 B2 | 11/2015 | Demarais et al. |
| 9,186,212 B2 | 11/2015 | Nabulovsky et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie |
| 9,339,332 B2 | 5/2016 | Srivastava |
| 9,345,530 B2 | 5/2016 | Ballakur et al. |
| 9,375,154 B2 | 6/2016 | Wang |
| 9,427,579 B2 | 8/2016 | Fain et al. |
| 9,439,598 B2 | 9/2016 | Shimada et al. |
| 9,649,064 B2 | 5/2017 | Toth et al. |
| 9,700,372 B2 | 7/2017 | Schaer |
| 9,707,034 B2 | 7/2017 | Schaer |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harringtpm |
| 10,016,233 B2 | 7/2018 | Pike |
| 10,022,085 B2 | 7/2018 | Toth et al. |
| 10,039,901 B2 | 8/2018 | Warnking |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |
| 10,182,865 B2 | 1/2019 | Naga et al. |
| 10,226,633 B2 | 3/2019 | Toth et al. |
| 10,245,429 B2 | 4/2019 | Deem et al. |
| 10,292,610 B2 | 5/2019 | Srivastava |
| 10,293,190 B2 | 5/2019 | Zarins et al. |
| 10,350,440 B2 | 7/2019 | Taylor |
| 10,363,359 B2 | 7/2019 | Toth et al. |
| 10,368,775 B2 | 8/2019 | Hettrick et al. |
| 10,368,944 B2 | 8/2019 | Schaer |
| 10,376,310 B2 | 8/2019 | Fain et al. |
| 10,383,685 B2 | 8/2019 | Gross et al. |
| 10,398,332 B2 | 9/2019 | Min et al. |
| 10,456,605 B2 | 10/2019 | Taylor |
| 10,470,684 B2 | 11/2019 | Toth et al. |
| 10,478,249 B2 | 11/2019 | Gross et al. |
| 10,499,877 B2 | 12/2019 | Peng et al. |
| 10,499,937 B2 | 12/2019 | Warnking |
| 10,543,037 B2 | 1/2020 | Shah |
| 10,850,091 B2 | 12/2020 | Zarins et al. |
| 11,305,098 B2 | 4/2022 | Zhou et al. |
| 11,801,085 B2 | 10/2023 | Wu et al. |
| 2001/0008976 A1 | 7/2001 | Wang |
| 2001/0023365 A1 | 9/2001 | Medhkour et al. |
| 2002/0042610 A1 | 4/2002 | Sliwa, Jr. et al. |
| 2002/0072741 A1 | 6/2002 | Sliwa, Jr. et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0028111 A1 | 2/2003 | Vaezy et al. |
| 2003/0074039 A1 | 4/2003 | Puskas |
| 2003/0114878 A1 | 6/2003 | Diederich et al. |
| 2003/0125726 A1 | 7/2003 | Maguire et al. |
| 2003/0181963 A1 | 9/2003 | Pellegrino et al. |
| 2003/0216721 A1 | 11/2003 | Diederich et al. |
| 2003/0216792 A1 | 11/2003 | Levin |
| 2004/0017395 A1 | 1/2004 | Cook |

(56)                References Cited

U.S. PATENT DOCUMENTS

| | | | |
|---|---|---|---|
| 2004/0019349 A1 | 1/2004 | Fuimaono et al. | |
| 2004/0082859 A1* | 4/2004 | Schaer | A61B 18/1492 |
| | | | 600/459 |
| 2004/0097819 A1 | 5/2004 | Duarte | |
| 2004/0106880 A1 | 6/2004 | Weng et al. | |
| 2004/0122494 A1 | 6/2004 | Eggers et al. | |
| 2004/0181178 A1 | 9/2004 | Aldrich et al. | |
| 2004/0242999 A1 | 12/2004 | Vitek et al. | |
| 2005/0038340 A1 | 2/2005 | Vaezy et al. | |
| 2005/0159738 A1 | 7/2005 | Visram et al. | |
| 2005/0165388 A1* | 7/2005 | Bhola | A61B 18/1492 |
| | | | 606/41 |
| 2005/0203501 A1 | 9/2005 | Aldrich et al. | |
| 2005/0215990 A1 | 9/2005 | Govari | |
| 2005/0228283 A1 | 10/2005 | Gifford et al. | |
| 2005/0228459 A1 | 10/2005 | Levin et al. | |
| 2005/0228460 A1 | 10/2005 | Levin et al. | |
| 2005/0261672 A1 | 11/2005 | Deem et al. | |
| 2005/0288730 A1 | 12/2005 | Deem | |
| 2006/0041277 A1 | 2/2006 | Deem et al. | |
| 2006/0052695 A1 | 3/2006 | Adam et al. | |
| 2006/0058711 A1 | 3/2006 | Harhen et al. | |
| 2006/0064081 A1 | 3/2006 | Rosinko | |
| 2006/0118127 A1 | 6/2006 | Chinn | |
| 2006/0142827 A1 | 6/2006 | Willard et al. | |
| 2006/0184069 A1 | 8/2006 | Vaitekunas | |
| 2006/0217772 A1 | 9/2006 | Libbus et al. | |
| 2006/0235286 A1 | 10/2006 | Stone et al. | |
| 2007/0060921 A1 | 3/2007 | Janssen et al. | |
| 2007/0072741 A1 | 3/2007 | Robideau | |
| 2007/0106292 A1 | 5/2007 | Kaplan | |
| 2007/0112300 A1 | 5/2007 | Roman et al. | |
| 2007/0135875 A1 | 6/2007 | Demarais et al. | |
| 2008/0039746 A1 | 2/2008 | Hissong et al. | |
| 2008/0215031 A1 | 9/2008 | Belfort et al. | |
| 2009/0012513 A1 | 1/2009 | Utley et al. | |
| 2009/0234407 A1 | 9/2009 | Hastings et al. | |
| 2009/0248005 A1 | 10/2009 | Rusin et al. | |
| 2010/0056862 A1* | 3/2010 | Bakos | A61B 17/3478 |
| | | | 600/106 |
| 2010/0130926 A1 | 5/2010 | Lee et al. | |
| 2010/0168570 A1 | 7/2010 | Sliwa et al. | |
| 2011/0118723 A1 | 5/2011 | Turner et al. | |
| 2011/0125206 A1 | 5/2011 | Bornzin | |
| 2011/0208096 A1 | 8/2011 | Demarais et al. | |
| 2012/0004656 A1 | 1/2012 | Jackson et al. | |
| 2012/0029511 A1 | 2/2012 | Smith et al. | |
| 2012/0265198 A1 | 10/2012 | Crow et al. | |
| 2012/0296232 A1 | 11/2012 | Ng | |
| 2013/0023897 A1 | 1/2013 | Wallace | |
| 2013/0085489 A1 | 4/2013 | Fain et al. | |
| 2013/0090649 A1 | 4/2013 | Smith et al. | |
| 2013/0096550 A1 | 4/2013 | Hill | |
| 2013/0116737 A1 | 5/2013 | Edwards et al. | |
| 2013/0123770 A1 | 5/2013 | Smith | |
| 2013/0131743 A1 | 5/2013 | Yamasaki et al. | |
| 2013/0150749 A1 | 6/2013 | McLean et al. | |
| 2013/0165925 A1 | 6/2013 | Mathur et al. | |
| 2013/0172872 A1 | 7/2013 | Subramaniam | |
| 2013/0274614 A1 | 10/2013 | Shimada et al. | |
| 2013/0289369 A1 | 10/2013 | Margolis | |
| 2013/0289682 A1 | 10/2013 | Barman et al. | |
| 2014/0018788 A1 | 1/2014 | Engelman et al. | |
| 2014/0058294 A1 | 2/2014 | Gross et al. | |
| 2014/0257266 A1 | 9/2014 | Kasprzyk et al. | |
| 2014/0257271 A1 | 9/2014 | Mayse et al. | |
| 2014/0274614 A1 | 9/2014 | Min et al. | |
| 2014/0275924 A1 | 9/2014 | Min et al. | |
| 2014/0288551 A1 | 9/2014 | Bharmi et al. | |
| 2014/0288616 A1 | 9/2014 | Rawat et al. | |
| 2014/0303617 A1 | 10/2014 | Shimada | |
| 2015/0119877 A1 | 4/2015 | Jameson et al. | |
| 2015/0289931 A1 | 10/2015 | Puryear et al. | |
| 2015/0320475 A1 | 11/2015 | Turovskiy | |
| 2015/0360007 A1 | 12/2015 | Schneider et al. | |

| | | |
|---|---|---|
| 2016/0000345 A1 | 1/2016 | Kobayashi et al. |
| 2016/0016016 A1 | 1/2016 | Taylor et al. |
| 2016/0045121 A1 | 2/2016 | Akingba et al. |
| 2017/0007310 A1 | 1/2017 | Rajagopalan et al. |
| 2017/0027460 A1 | 2/2017 | Shimada et al. |
| 2017/0035310 A1 | 2/2017 | Shimada et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0001054 A1 | 1/2020 | Jimenez et al. |
| 2020/0046248 A1 | 2/2020 | Toth et al. |
| 2020/0077907 A1 | 3/2020 | Shimada et al. |
| 2020/0230373 A1 | 7/2020 | Stankus |
| 2020/0297980 A1 | 9/2020 | Murphy et al. |

FOREIGN PATENT DOCUMENTS

| | | | |
|---|---|---|---|
| CA | 2925946 | | 5/2015 |
| EP | 1299035 | | 4/2003 |
| EP | 1503685 | | 2/2005 |
| EP | 1579889 | | 9/2005 |
| EP | 1351738 | B1 | 1/2007 |
| EP | 0748232 | B2 | 10/2008 |
| EP | 2359764 | | 8/2011 |
| EP | 2415495 | A1 | 2/2012 |
| EP | 2430996 | | 3/2012 |
| EP | 2842604 | | 3/2015 |
| EP | 2865350 | A2 | 4/2015 |
| EP | 2968984 | | 1/2016 |
| EP | 2995250 | | 3/2016 |
| EP | 2734259 | | 11/2016 |
| EP | 3157612 | | 4/2017 |
| EP | 3217904 | | 9/2017 |
| EP | 3245962 | A2 | 11/2017 |
| EP | 3368156 | | 2/2020 |
| EP | 3799931 | | 4/2021 |
| WO | WO 99/02096 | | 1/1999 |
| WO | WO 01/087169 | | 11/2001 |
| WO | WO 01/095820 | | 12/2001 |
| WO | WO2002/005897 | | 1/2002 |
| WO | WO 2002/019934 | | 3/2002 |
| WO | WO2003/022167 | | 3/2003 |
| WO | WO2003/051450 | | 6/2003 |
| WO | WO 2005/070316 | | 8/2005 |
| WO | WO2006/041881 | | 4/2006 |
| WO | WO2006/060053 | | 6/2006 |
| WO | WO 2007/001981 | | 1/2007 |
| WO | WO2007/014003 | | 2/2007 |
| WO | WO 2007/036035 | | 4/2007 |
| WO | WO 2008/099424 | | 8/2008 |
| WO | WO 2012/009486 | | 1/2012 |
| WO | WO 2015/057411 | | 4/2015 |
| WO | WO 2015/103541 | | 7/2015 |
| WO | WO 2017/099950 | | 11/2016 |

(56)                    References Cited

FOREIGN PATENT DOCUMENTS

WO      WO 2019/023280      1/2019
WO      WO2019/050617       3/2019

OTHER PUBLICATIONS

Benito, Fernando et al., "Radiofrequency catheter ablation of accessory pathways in infants," Heart, vol. 78, p. 160-162, 1997.
Chang, Isaac A. et al., "Thermal Modeling of Lesion Growth with Radiofrequency Ablation Devices," Biomedical Engineering Online vol. 3, p. 27, 2004.
Chung, Andrew et al., "Thermal dosimetry of a focused ultrasound beam in vivo by magnetic resonance imaging," Medical Physics, vol. 26, No. 9, p. 2017-2026, Sep. 1999.
Damianou, Christakis et al., "High Intensity Focused Ultrasound Ablation of Kidney Guided MRI," Ultrasound in Med. & Biol., vol. 30, No. 3, p. 397-404, 2004.
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Diederich, Chris J. et al., "Ultrasound Technology for Hyperthermia," Ultrasound in Med. & Biol., vol. 25, No. 6, p. 871-887, 1999.
Fry, F.J. et al., "Production of Reversible Changes in the Central Nervous System by Ultrasound," Science, vol. 127, p. 83-84, Jan. 1958.
Gavrilov, L.R. et al., The Effect of Focused Ultrasound on the Skin and Deep Nerve Structures of Man and Animal, p. 279-292.
Gavrilov, L.R., "Use of Focused Ultrasound for Stimulation of Nerve Structures," Ultrasonics, p. 132-138, May 1984.
Graham, S.J. et al., "Quantifying Tissue Damage Due to Focused Ultrasound Heating Observed by MRI" Magnetic Resonance in Medicine vol. 41, p. 321-328, 1999.
Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.
Hacker, Axel et al., "Extracorporeal Organotripsy for Renal Tumours," Current Opinion in Urology, vol. 13, p. 221-225, 2003.
Hausberg, Martin et al., "Sympathetic Nerve Activity in End-Stage Renal Disease," Circulation, vol. 106, p. 1974-1979, 2002.
Ho, Siew Yen et al., "Anatomy of the Left Atrium: Implications for Radiofrequency Ablation of Atrial Fibrillation," J Cardiovasc Electrophysiol., vol. 10, p. 1525-1533, Nov. 1999.
Israel, Gary M. et al., "MRI of the Kidney and Urinary Tract," Journal of Magnetic Resonance Imaging, vol. 24, p. 725-734, 2006.
Jiang, S.C. et al., "Effects of Thermal Properties and Geometrical Dimensions on Skin Burn Injuries," Burns, vol. 28, p. 713-717, 2002.
Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lauder, Lucas et al., "Renal Denervation in the Management of Hypertension," EuroIntervention, vol. 20, p. e467-e478, 2024.

Lele, P.P., "Effects of Focused Ultrasonic Radiation on Peripheral Nerve, with Observations on Local Heating," Experimental Neurology, vol. 8, p. 47-83, 1963.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Mahfoud, Felix et al., "Device Therapy of Hypertension," Circulation Research nol. 128, p. 1080-1099, Apr. 2021.
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue vols. Using High Intensity Focused Ultrasound" Ultrasound in Med. & Biol. vol. 22 no. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Mitchell, G.A.G et al., "An Anatomical Evaluation of Operations for Hypertension," Proceedings of the Anatomical Society vol. LIV., No. 10, p. 545-560.
Mompeo, Blanca et al., "The Gross Anatomy of the Renal Sympathetic Nerves Revisited," Clinical Anatomy vol. 29, p. 660-664, Apr. 2016.
Moore, J.H. et al., "The Biophysical Effects of Ultrasound on Median Nerve Distal Latencies," Electromyogr. Clin. Neurophysiol., vol. 40, p. 169-190, 2000.
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, Jan./Feb. 1995.
Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.
Nikfarjam, Mehrdad et al., "Mechanisms of Focal Heat Destruction of Liver Tumors," Journal of Surgical Research, vol. 127, No. 2, p. 208-223, Aug. 2005.
Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803 e.8, Sep. 2005.
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.
Papademetriou, Vasilios et al., "Renal Nerve Ablation for Resistant Hypertension, How Did We Get Here, Present Status, and Future Directions," Circulation, No. 129, p. 1440-1451, 2014.
Pozzoli, Alberto et al., "Electrophysiological Efficacy of Epicor High-Intensity Focused Ultrasound," European Journal of Cardio-Thoracic surgery, vol. 42, p. 129-134, 2012.
Riis, Thomas et al., "Effective Ultrasonic Stimulation in Human Peripheral Nervous System," IEE Transactions on Biomedical Engineering, vol. XX, No. XX, p. 1-8, XXXX 2021.
Roux, N. et al., "The Myocardial Sleeves of the Pulmonary Veins: Potential Implications for Atrial Fibrillation," Surg. Radiol. Anat., vol. 26, p. 285-289, Feb. 2004.
Schuarte, Patrick et al., "Catheter Ablation of Cardiac Autonomic Nerves for Prevention of Vagal Atrial Fibrillation," Circulation vol. 102, p. 2774-2780, 2000.
Tellez, Armando et al., "Renal Artery Nerve Distribution and Density in the Porcine Model: Biologic Implications for the Development of Radiofrequency Ablation Therapies," Translational Research vol. 162 No. 6, p. 381-389, Dec. 2013.

(56) References Cited

OTHER PUBLICATIONS

Ter Haar, G., "Ultrasound Focal Beam Surgery," Ultrasound in Med. & Biol., vol. 21, No. 9, p. 1089-1100, 1995.

Ter Haar, G.R. et al., "Ultrasonic Heating of Mammalian Tissues In vivo," Br. J. Cancer vol. 45, Supp. V., p. 65-67, 1982.

Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.

Trippodo, Nick C. et al., "Similarities of Genetic (Spontaneous) Hypertension," Circulation Research vol. 48, No. 3, p. 309-319, Mar. 1981.

Urban, Bruce A. et al., "Three-dimensional vol. rendered CT Angiography of the Renal Arteries and Veins: Normal Anatomy, Variants, and Clinical Applications," RG vol. 21 No. 2, p. 373-386, Mar.-Apr. 2001.

Wang, Shyh-Hau et al., "Effects of Low Intensity Ultrasound on the Conduction Property of Neural Tissues," IEEE International Ultrasonics, Ferroelectrics, and Frequency Control Joint $50^{th}$ Anniversary Conference, p. 1824-1827, 2004.

Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.

Wells, P.N.T., "Functional Modification: Clinical Applications," Biomedical Ultrasonics, p. 470-504, 1977.

Winternitz, Sherry R. et al., "Importance of the Renal Nerves in the Pathogenesis of Experimental Hypertension," Hypertension (supp. III), vol. 4, No. 5, p. III-08-III-115, Sep.-Oct. 1982.

Wulff, V.J. et al., "Effects of Ultrasonic Vibrations on Nerve Tissues," P.S.E.B.M., vol. 76, p. 361-366, 1951.

Yarmolenko, Pavel S. et al., "Thresholds for thermal damage to normal tissues: An update," Int. J. Hyperthermia, vol. 27 No. 4, p. 320-343, Jun. 2011.

Young, Robert R. et al., "Functional Effects of Focused Ultrasound on Mammalian Nerves," Science, vol. 134, p. 1521-1522, Nov. 1961.

Zimmer, J.E. et al., "The Feasibility of Using Ultrasound for Cardiac Ablation," IEEE Transactions on Biomedical Engineering, vol. 42, No. 9, p. 891-897, Sep. 1995.

International Search Report and Written Opinion dated Feb. 20, 2023 in International Application No. PCT/IB2022/056561.

Borchert, Bianca et al., "Lethal Atrioesophageal Fistual After Pulmonary Vein Isolation using High- Intensity Focused Ultrasound (Hifu)" J. Hrthm vol. 5, Issue 1, p. 145-148, Jan. 2008.

Calkins, Hugh et al., "Temperature Monitoring During Radiofrequency Catheter Ablation Procedures Using Closed Loop Control," Circulation vol. 90, No. 3, p. 1279-1286, Sep. 1994.

Deardorff, Dana L et al., "Control of interstitial thermal coagulation: Comparative evaluation of microwave and ultrasound applicators," Medical Physics vol. 28, No. 1, p. 104-117, Jan. 2001.

Dinerman, Jay L et al., "Temperature Monitoring During Radiofrequency Ablation," Journal of Cardiovascular Electrophysiology, vol. 7 No. 2, p. 163-173, Feb. 1996.

Esler, Murray et al., "The future of renal denervation," Autonomic Neuroscience: Basic and Clinical, vol. 204, p. 131-138, May 2017.

Filonenko, E.A et al., "Heating of Biological Tissues by Two-Dimensional Phased Arrays with Random and Regular Element Distributions," Acoustical Physics, vol. 50 No. 2, p. 222-231, 2004.

Fry, William J., "Action of Ultrasound on Nerve Tissue-A review," The Journal of the Acoustical Society of America, vol. 25 No. 1, p. 1-5, Jan. 1953.

Fry, Frank J., "Precision High Intensity Focusing Ultrasonic Machines for Surgery," High Intensity Focused U.S., 152-156, Sep. 6-7, 1957.

Haines, David, "Biophysics of Ablation: Application to Technology," Journal of Cardiovascular Electrophysiology, vol. 15, No. 10, pg. S2-S11, Oct. 2004.

Hynynen, K et al., "Design of Ultrasonic Transducers for Local Hyperthermia," Ultrasound in Med. & Biol., vol. 7, No. 4, p. 397-402, Feb. 1981.

Hynynen, K. et al., "Temperature measurements during ultrasound hyperthermia," Medical Physics vol. 16, No. 4, p. 618-626, Jul./Aug. 1989.

Jolesz, Ferenc A. et al., "MR Imaging—Controlled Focused Ultrasound Ablation: A Noninvasive Image-Guided Surgery," Magnetic Resonance Imaging Clinics of North America, vol. 13, Issue 3, p. 545-560, 2005.

Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.

Lafon, C. et al., "Design and Preliminary Results of an Ultrasound Applicator for Interstitial Thermal Coagulation," Ultrasound in Medicine & Biology, vol. 24, No. 1, p. 113-122, 1998.

Lewis, Matthew A. et al., "Thermometry and Ablation Monitoring with Ultrasound," Int. J. Hyperthermia vol. 31, Issue 2, p. 163-181, Mar. 2015.

Liu, Xinmeng et al., "Visualization and mapping of the right phrenic nerve by intracardiac echocardiography during atrial fibrillation ablation," Europace vol. 25, p. 1352-1360, 2023.

Mendelsohn, Farrell O., "Microanatomy of the Renal Sympathetic Nervous System," Endovascular Today, p. 59- 62, Oct. 2013.

Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.

Quadri, Syed A. et al., "High-intensity focused ultrasound: past, present, and future in neurosurgery," Neurosurgical Focus, vol. 44, No. 2, p. 1-9, Feb. 2018.

Ross, Anthony B. et al., "Highly directional transurethral ultrasound applicators with rotational control for MRI-guided prostatic thermal therapy," Physics in Medicine & Biology, vol. 49, p. 189-204, Jan. 2004.

Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.

Sanghvi, Kintur et al., "Rationale and design for studies of renal denervation in the absence (SPYRAL HTN OFF-MED) and presence (SPYRAL HTN ON-MED of antihypertensive medications," American Heart Journal, vol. 180, p. e1-e2. Oct. 2016.

Satou, Shunsuke et al., "Observation of renal sympathetic nerves by intravascular ultrasound," Hypertension Research vol. 42, p. 1092-1094, 2019.

Schmidt, Boris et al., "Balloon Catheters for Pulmonary Vein Isolation," Herz vol. 33, p. 580-584, 2008.

Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.

Stauffer, P.R. et al., "13 Interstitial Heating Technologies," Thermoradiotherapy and Thermochemotherapy, p. 279-320, 1995.

Swanson, David K. et al., "Tissue temperature Feedback Control of Power, The Key to Successful Ablation," Innovations, vol. 6 No. 4, p. 276-282, Jul./Aug. 2011.

Tabei, Makoto et al., "A k-space method for coupled first-order acoustic propagation equations," J. Acoust. Soc. Am., vol. 111, No. 1, pt. 1, p. 53-63, Jan. 2002.

Tzafriri, Abraham R. et al., "Innervation Patterns May Limit Response to Endovascular Renal Denervation," Journal of the American College of Cardiology, vol. 64, No. 11, p. 1079-1087, Sep. 2014.

Umemura, Shin-ichiro, "Focused ultrasound transducer for thermal treatment," International Journal of Hyperthermia, vol. 31, No. 2, p. 216-221, 2015.

Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.

Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.

Applications, Second Edition, Edited by Shoei K. Stephen Huang, MD & David J. Wilber, MD, p. 103-112, 2000.

(56) References Cited

OTHER PUBLICATIONS

AGA Medical Corporation, "Amplatzer Sizing Balloon Summary of Safety and Effectiveness." Jul. 12, 2000.

Aomori Olympus Optical Co., Ltd., "SMDA 510(k) Summary for Balloon Catheter," Nov. 14, 2003.

Angiodynamics, Inc., K032069, WorkHorse II Percutaneous Transluminal Angioplasty Balloon Catheter, Letter from Department of Health & Human Services re premarket notification, Aug. 27, 2003.

ArteriA Medical Science, Inc., 510(k) Summary, ArteriA Occlusion Balloon, Oct. 28, 2002.

Boston Scientific, Peripheral Interventions, Product Catalogue, » 2015.

Choi, Charles D., "An Integrated Compliant Balloon Ultrasound Catheter for Intravascular Strain Imaging," IEEE Transactions on Ultrasonics, Ferroelectrics, and Frequency Control, vol. 49, No. 11, Nov. 2002.

Choi, C.D., et al., « Strain Imaging of Vascular Pathologies Using a Compliant Balloon Catheter, 2000 IEEE Ultrasonics Symposium, 1771-74, 2000.

Cook Incorporated, Special 510(k) Premarket Notification, PTA Balloon Catheter, Jun. 26, 2003.

Cook Urological, "510(k) Premarket Notification, Pursuit Balloon Dilation Catheter," Jan. 8, 1999.

CryoVascular Systems, Inc., "510(k) Summary for Polar Cath, a Percutaneous Transluminal Angioplasty Catheter," Aug. 29, 2003.

Lopes, Demetrius, "Balloon Design and Performance: Presentation of Various Types of Balloons on the Market," Rush University Medical Center, Chicago Balloon Summit 2016.

Martin, Louis G., et al., "Long-Term Results of Angioplasty in 110 Patients with Renal Artery Stenosis," Angioplasty and Endoprostheses, Journal of Vascular and Interventional Radiology, Nov. 1992, p. 619-622.

Mehta, Manish, "Compliant Occlusion Balloons. Use of Compliant Occlusion Balloons during EVAR for AAA rupture," Insert to Endovascular Today, Nov. 2008, pp. 28-31.

Meyers, Philip, M., "Temporary Endovascular Balloon Occlusion of the Internal Carotid Artery with a Nondetachable Silicone Balloon Catheter: Analysis of Technique and Cost," AJNR Am. J. Neuroradiol 20:559-564, Apr. 1999.

Micro Therapeutics, Inc., Special 510(k): HyperForm Occlusion Balloon Catheter, Attachment 6, Jun. 20, 2001.

Micro Therapeutics, Inc., Special 510(k): HyperGlide Occulsion Balloon Catheter, Attachment 4, Jun. 18, 2002.

Olympus America, "Balloon Catheter, Multi-3V Plus Extraction Balloons," downloaded from https://medical.olympusamerica.com/products/multi-3v-plus-extraction-balloons, Jun. 10, 2022.

Qureshi, Athar M., "Transcatheter Angioplasty for Acquired Pulmonary Vein Stenosis after Radiofrequency Ablation," Circulation, 1336-42; Sep. 16, 2003.

Saab, Mark A., "Applications of High-Pressure Balloons in the Medical Device Industry," Medical Device & Diagnostic Industry Magazine, 2000.

Sos, Thomas A., "Technical Aspects of Percutaneous Transluminal Angioplasty in Renovascular Disease," Nephron 44: Suppl. 1, pp. 45-50, 1986.

Tautorat, Carsten et al., "Balloon-based measuring system for compliance investigations," Current Directions in Biomedical Engineering 2018: 4(1): pp. 539-542, 2018.

Van Der Giessen, Willem J. et al., "A New Intracoronary Measurement Catheter, Metricath, Compared to Intravascular Ultrasound and Quantitative Coronary Angiography in a Stented Porcine Coronary Model," Catheterization and Cardiovascular Interventions, 57: pp. 2-9, 2002.

Wang, Paul J., "Overview of Balloon Approaches to AF Ablation," Journal of the American College of Cardiology, vol. 68, No. 25, 2016.

Accornero, Neri et al., "Selective Activation of Peripheral Nerve Fibre Groups of Different Diameter by Triangular Shaped Stimulus Pulses", J. Physiol. (1977), 273, _ 539-560, 22 Q9S.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).

American Heart Association—Pulmonary Hypertension: High Blood Pressure in the Heart-to-Lung System, (last reviewed Oct. 31, 2016).

Appeal Brief of Patent Owner from Reexamination 95-002, 110.

Aytac, et al., "Correlation Between the Diameter of the Main Renal Artery and the Presence of an Accessory Renal Artery", J Ultrasound Med 22:433-439, 2003 (.

Azizi, Michel et al., Ultrasound renal denervation for hypertension resistant to a triple medication pill (RADIANCE-HTN TRIO): a randomised, multicentre, single-blind, sham-controlled trial, 397 Lancet 2476 (2021).

Bailey, M.R. et al., Physical Mechanisms of the Therapeutic Effect of Ultrasound (A Review), Acoustical Physics, vol. 49, No. 4, 2003, pp. 369-388.

Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.

Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.

Bhatt, D.L., et al., A Controlled Trial of Renal Denervation for Resistant Hypertension, New England J. Med., 370:1393-1401 (2014).

Bhatt, Deepak L. et al., Long-term outcomes after catheter-based renal artery denervation for resistant hypertension: final follow-up of the randomised SYMPLICITY HTN-3 Trial, 400 Lancet 1405 (2022).

Billard, B.E. et al., Effects of Physical Parameters on High Temperature Ultrasound Hyperthermia, Ultrasound in Med. & Biol. vol. 16, No. 4, pp. 409-420, 1990.

Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).

Blanketjin, Peter, Sympathetic Hyperactivity in Chronic Kidney Disease, Neprhol Dial Transplant, vol. 19, No. 6, 1354-1357 (2004).

Blum et al., Treatment of Ostial Renal-Artery Stenoses with Vascular Endoprostheses after Unsuccessful Balloon Angioplasty, N. Engl. J. Med. 336 459-65 (1997).

Bonsignore, C., "A Decade of Evolution in Stent Design", Proceedings of the International Conference on Shape Memory and Superelastic Technologies, (2003).

Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).

Bush, et al., "Endovascular revascularization of renal artery stenosis: Technical and clinical results", Journal of Vascular Surgery, 2001, May, 1041-1049 (2001).

Camasao, D. B. et al., The mechanical characterization of blood vessels and their substitutes in the continuous quest for physiological-relevant performances: A critical review, Materials Today Bio, vol. 10 (2021).

Carter, J., "Microneurography and Sympathetic Nerve Activity: A Decade-By-Decade Journey across 50 Years," Journal of Neurophysiology, vol. 121, No. 4. doi: 10.1 152/jn.00570.2018.

Carter, Stefan et al., Measurement of Renal Artery Pressures by Catheterization in Patients with and without Renal Artery Stenosis, Circulation, vol. XXXIII, 443-449 (1966).

Chapelon, J.Y., "Treatment of Localised Prostate Cancer with Transrectal High Intensity Focused Ultrasound,"European Journal of Ultrasound 9, 31-38, 1999.

Charlesworth, Peter et al., Renal Artery Injury from a Fogarty Balloon Catheter, Journal of Vascular Surgery, vol. 1, No. 4, 573-576 (1984).

Chart showing priority claims of the '629 patent, exhibit to Petition for Inter Partes Review of U.S. Pat. No. 8,845,629, filed Jan. 13,

(56) References Cited

OTHER PUBLICATIONS 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Coates, Paul et al., "Time, Temperature, Power, and Impedance Considerations for Radiofrequency Catheter Renal Denervation," Cardiovascular Revascularization Medicine 42, 171-177 (2022).
Corrected Patent Owner's Response to Office Action, dated May 10, 2013, from File History of Inter Partes Reexamination U.S. Appl. No. 95/002,110.
Correspondence from PTAB Deputy Chief Clerk to Counsel re conference call request—Exhibit 3001 in the Patent Trial and Appeal Board, United States Patent and Trademark Office, Petition No. PTAB-IPR2022-00431.
Curriculum Vitae of Dr. Chris Daft.
Curriculum Vitae of Dr. John M. Moriarty.
Curriculum Vitae of Dr. Michael Bohm.
Curriculum Vitae of Farrell Mendelsohn.
Dangas, G., et al., Intravascular Ultrasound-Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Deardorff, Dana et al., Ultrasound Applicators with Internal Cooling for Interstitial Thermal Therapy, SPIE vol. 3594, 36-46, Jan. 1999.
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP2261905 dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner's Response, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Dibona, Gerald F., "Neural Control of the Kidney, Past, Present and Future," 41 [Part II] Hypertension 621 24 (2003).
Dibona, Gerald, Sympathetic Nervous System and Kidney in Hypertension, Current Opinion in Nephrology and Hypertension, vol. 11, 197-200 (2002).

Dibona, Gerald F. et al., "Neural Control of Renal Function", 77 Physiological Reviews No. 1, 75 (1997).
Diederich, et al., "Catheter-based Ultrasound Applicators for Selective Thermal Ablation: progress towards MRI-guided applications in prostate," International Journal of Hyperthermia, 20:7, 739-756.
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al al.," Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_doi:10.1109fTBME.2002. 807323.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019—Preliminary Remarks for EP appeal No. T2680/16-3.3.4.01.
European Search Report in Application No. 12180431.4 dated Jan. 17, 2013.
European Communication in Application No. 12180431.4 dated Oct. 23, 2013.
European Office Action in Application No. 12180431.4.
European Patent No. 12167931, Claims of the Main Request dated Sep. 30, 2016.
European Search Report (Supplementary) in Application No. 14775754.6 dated Feb. 17, 2016.
European Search Report in Application No. 218186547 dated Nov. 19, 2018.
European Search Report in Application No. 20202272.9 dated Mar. 1, 2021.
Fan, Xiaobing et al., "Control of the Necrosed Tissue vol. during Noninvasive Ultrasound Surgery using a 16-Element Phased Array," Department of Radiology, Brigham and Women's Hospital, Harvard Medical School, Oct. 31, 1994.
Fengler, Karl et al., A Three-Arm Randomized Trial of Different Renal Denervation Devices and Techniques in Patients with Resistant Hypertension (RADIOSOUND-HTN), 139 Circulation 590 (2019).
File History to EP1802370B1 Part 1.
File History to EP1802370B1 Part 2.
File History to EP1802370B1 Part 3.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).

(56) References Cited

OTHER PUBLICATIONS

Hansen et al., The Transplanted Human Kidney Does Not Achieve Functional Reinnervation, 87 Clinical Science 13 (1994).

Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.

He, D. S. et al., Application of Ultrasound Energy for Intracardiac Ablation of Arrhythmias, European Heart Journal, vol. 16, 961-966 (1995).

Heffner, H. et al., "Gain, Band Width, and Noise Characteristics of the Variable-Parameter Amplifier," Journal of Applied Physics, vol. 29, No. 9, Sep. 1 958, 1 1 pages.

Holmes, David R. et al., Pulmonary vein stenosis complicating ablation for atrial fibrillation: clinical spectrum and interventional considerations, 2 JACC Cardiovasc. Interv. 267 (2009).

Hsu, Thomas H. S. et al., Radiofrequency ablation of the kidney: acute and chronic histology in porcine model, 56 Urology 872 (2000).

Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).

Huang, et al., Renal Denervation Prevents and Reverses Hyperinsulinemia-Induced Hypertension in Rats, Hypertension 32 (1998) pp. 249-254.

Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.

Isles et al., Management of Renovascular Disease: A Review of Renal Artery Stenting in Ten Studies, QJM 92, 159-67 (1999).

Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.

Janssen, B. J. A., et al. "Renal nerves in hypertension." Miner Electrolyte Metab., 15:74-82 (1989).

Janzen, Nicolette et al., Minimally Invasive Ablative Approaches in the Treatment of Renal Cell Carcinoma, Current Urology Reports, vol. 3 (2002).

Kaltenbach, Benjamin et al., Renal Artery Stenosis After Renal Sympathetic Denervation, Journal of the American College of Cardiology, vol. 60, No. 25 (2012).

Kapural, Leonardo, et al., "Radiofrequency Ablation for Chronic Pain Control," Anesthetic Techniques in Pain Management, pp. 517-525, 2001.

Katholi, R.E., et al., Importance of Renal Sympathetic Tone in the Development of DOCA-Salt Hypertension in The Rat, Hypertension, 2:266-273 (1980).

Kim, Yun-Hyeon et al., Pulmonary vein diameter, cross-sectional area, and shape: CT analysis, Radiology Society of North America, vol. 235, No. 1, 49-50 (2005).

Kirsh, Danielle, Balloon Catheters: What are some key design considerations?, MASSDEVICE (Dec. 6, 2016).

Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).

Koomans, Hein et al., Sympathetic Hyperactivity in Chronic Renal Failure: A wake-up call, Frontiers in Nephrology, vol. 15, 524-537 (2004).

Kuo, et al., "Atrial Fibrillation: New Horizons", Chang Gung Med J vol. 26 No. Oct. 10, 2003.

Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).

Lee, Jong Deok et al., MR imaging-histopathologic correlation of radiofrequency thermal ablation lesion in a rabbit liver model: observation during acute and chronic stages, 2 Korean J. Radiol. 151 (2001).

Levin, S., et al., ARDIAN: Succeeding Where Drugs Fail—Treating Hypertension in the Cath Lab, In Vivo, 27:23 (2009).

Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).

Marine, Joseph E., Catheter ablation therapy for supraventricular arrhythmias, 298 JAMA 2768 (2007).

Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.

Matsumoto, Edward D. et al., Short-term efficacy of temperature-based radiofrequency ablation of small renal tumors, 65 Urology 877 (2005).

Medtronic Press Release, Medtronic Announces U.S. Renal Denervation Pivotal Trial Fails to Meet Primary Efficacy Endpoint While Meeting Primary Safety Endpoint (Jan. 9, 2014).

Medtronic Inc., Renal Denervation (RDN): Novel Catheter-Based Treatment for Hypertension, Scientific Background, 2011.

Medtronic Scientific Background, Hypertension and the Symplicity Renal Denervation System.

Medtronic, Symplicity RDN Common System Q&A.

Medtronic Inc., The Symplicity RDN System, 2012.

Millard, et al., Renal Embolization for Ablation of Function In Renal Failure And Hypertension, Postgraduate Med. J. 65, 729-734 (1989).

Mitchell, et al., "The Renal Nerves" British Journal of Urology, Read by invitation at the Sixth Annual Meeting of the British Association of Urological Surgeons on Jun. 30, 1950.

Morrissey, D. M. "Sympathectomy in the treatment of hypertension." Lancet, CCLXIV:403-408 (1953).

Nair et al., "The Need for and the Challenges of Measuring Renal Sympathetic Nerve Activity," Heart Rhythm 2016; 13:1166-1171.

Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).

Netter, Frank, Atlas of Human Anatomy, Icon Learning Systems, Rochester, NY (2002).

Neumann, Jutta, Sympathetic hyperactivity in chronic kidney disease: Pathogenesis, clinical relevance, and treatment, International Society of Nephrology, vol. 65, 1568-1576 (2004).

News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.

Notice of Deposition of Tucker, filed Dec. 30, 2022 in the Patent Trial and Appeal Board, United States Patent and Trademark Office, Petition No. PTAB-IPR2022-00431.

Notice of Deposition of van der Weide, filed Dec. 30, 2022 in the Patent Trial and Appeal Board, United States Patent and Trademark Office, Petition No. PTAB-IPR2022-00431.

Notice re filing date accorded, dated Feb. 10, 2022 in the Patent Trial and Appeal Board, United States Patent and Trademark Office, Petition No. PTAB-IPR2022-00431.

Nozawa, T., et al. "Effects of long-term renal sympathetic denervation on heart failure after myocardial infarction in rats." Heart Vessels, 16:51-56 (2002).

Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").

Olsson, R. et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.

(56) References Cited

OTHER PUBLICATIONS

Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.

Order Setting Oral Hearing 37 C.F.R. § 42.70, dated Mar. 24, 2023 in the Patent Trial and Appeal Board, United States Patent and Trademark Office, Petition No. PTAB-IPR2022-00431.

Osborn, J., "Catheter-Based Renal Nerve Ablation as a Novel Hypertension Therapy, Lost, and Then Found," in Translation.

Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).

Page, Irvine H. & George J. Heuer, The Effect of Renal Denervation on Patients Suffering from Nephritis, 14 J. Clinical Investigation 443 (1935) (received for publication in 1935).

Papademetriou, Vasilios et al., Renal Sympathetic Denervation for the Treatment of Difficult-to-Control or Resistant Hypertension, 2011 Int. J. Hypertension, Article 196518 (2011).

Papademetriou, et al., "Renal Sympathetic Denervation: Hibernation or Resurrection?", Cardiology 2016; 135, 11 pgs.

Papadopoulos, N., "Evaluation of a Small Flat Rectangular Therapeutic Ultrasonic Transducer Intended for Intravascular Use," Ultrasonics 74, 196-203, 2017.

Pappone C, et al., "Circumferential radiofrequency ablation of pulmonary vein ostia: a new anatomic approach for curing atrial fibrillation", Circulation. 2000; 102(21): 2619-2628. (2000).

Patent Owner's Amended Objections to Evidence Under 37 C.F.R. §42.64.

Patent Owner's Mandatory Notice, filed Feb. 3, 2022 in the Patent Trial and Appeal Board, United States Patent and Trademark Office, Petition No. PTAB-IPR2022-00431.

Patent Owner's Notice of Deposition of Dr. Chris Daft, filed Sep. 20, 2022 in the Patent Trial and Appeal Board, United States Patent and Trademark Office, Petition No. PTAB-IPR2022-00431.

Patent Owner's Notice of Deposition of Dr. Chris Daft filed Feb. 21, 2023 in the Patent Trial and Appeal Board, United States Patent and Trademark Office, Petition No. PTAB-IPR2022-00431.

Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.

Patent Owner's Notice of Deposition of Dr. John Moriarty, filed Feb. 21, 2023 in the Patent Trial and Appeal Board, United States Patent and Trademark Office, Petition No. PTAB-IPR2022-00431.

Patent Owner's Objections to Evidence, filed Aug. 18, 2022 in the Patent Trial and Appeal Board, United States Patent and Trademark Office, Petition No. PTAB-IPR2022-00431.

Patent Owner's Power of Attorney, filed Feb. 3, 2022 in the Patent Trial and Appeal Board, United States Patent and Trademark Office, Petition No. PTAB-IPR2022-00431.

Patent Owner Medtronic Ireland Power of Attorney, filed May 10, 2022 in the Patent Trial and Appeal Board, United States Patent and Trademark Office, Petition No. PTAB-IPR2022-00431.

Patent Owner's Preliminary Response, filed May 10, 2022 in the Patent Trial and Appeal Board, United States Patent and Trademark Office, Petition No. PTAB-IPR2022-00431.

Patent Owner's Request for Oral Hearing, filed Mar. 23, 2023 in the Patent Trial and Appeal Board, United States Patent and Trademark Office, Petition No. PTAB-IPR2022-00431.

Patent Owner's Response, filed Oct. 27, 2022 in the Patent Trial and Appeal Board, United States Patent and Trademark Office, Petition No. PTAB-IPR2022-00431.

Patent Owner's Sur-Reply, filed Mar. 9, 2023 in the Patent Trial and Appeal Board, United States Patent and Trademark Office, Petition No. PTAB-IPR2022-00431.

Patent Owner's Updated Mandatory Notice, filed May 10, 2022 in the Patent Trial and Appeal Board, United States Patent and Trademark Office, Petition No. PTAB-IPR2022-00431.

Peet, M.M., Hypertension and Its Surgical Treatment by Bilateral Supradiaphragmatic Splanchnicectomy, Am. J. Surgery, LXXV:48-68 (1948).

Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.

Petitioner ReCor's Biography of Dr. Neil C. Barman.

Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.

Petitioner's Power of Attorney for Recor Medical, Inc., filed Jan. 13, 2022 in the Patent Trial and Appeal Board, United States Patent and Trademark Office, Petition No. PTAB-IPR2022-00431.

Petitioner Reply, filed Jan. 23, 2023 in the Patent Trial and Appeal Board, United States Patent and Trademark Office, Petition No. PTAB-IPR2022-00431.

Petitioners' Request for Oral Argument, filed Mar. 21, 2023 in the Patent Trial and Appeal Board, United States Patent and Trademark Office, Petition No. PTAB-IPR2022-00431.

Petitioners' Updated Mandatory Notices, dated Jan. 18, 2022 in the Patent Trial and Appeal Board, United States Patent and Trademark Office, Petition No. PTAB-IPR2022-00431.

Plaintiff's Nullity Brief, dated Jan. 14, 2022, in the Munich Federal Patent Court, Nullity Suit 6 Ni 32/22.

Plaintiff's Reply to the May 11, 2022 Response, dated Jul. 18, 2022, in the Munich Federal Patent Court, Nullity Suit 6 Ni 32/22.

Plaintiff's Response to Court Order disagreeing with Stay of Proceedings dated Oct. 28, 2022 in Mannheim District Court, Infringement suit 7 O 147/21.

Plaintiff's Technical Brief dated Sep. 29, 2022 in the Mannheim District Court, Infringement suit 7 O 147/21.

Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).

Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.

Prochnau, Dirk et al., Catheter-based renal denervation for drug-resistant hypertension by using a standard electrophysiology catheter, EuroIntervention, vol. 7, 1077-1080 (2012).

Pugsley, et al., The vascular system: An overview of structure and function, Journal of Pharmacological and Toxicological Methods 44 (2000) 333-340.

Purerfellner, Helmut et al., Incidence, Management and Outcome in Significant Pulmonary Vein Stenosis Complicating Ablation for Atrial Fibrillation, 93 Am. J. Cardiol. 1428 (2004).

Purerfellner, Helmut & Martinek, Martin, Pulmonary vein stenosis following catheter ablation of atrial fibrillation, 20 Curr. Opin. Cardiol. 484 (2005).

Reaz, M.B.I., et al., "Techniques of EMG signal analysis: detection, processing, classification and applications," Biological Procedures Online, Jan. 2006, 25 pages.

Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.

Romanes, G.J., Cunningham's Textbook of Anatomy (11th ed. 1972).

Ryan, Steve, What are the Risks Associated with a Pulmonary Vein Ablation Procedure?, Atrial Fibrillation: Resources for Patients (last accessed Oct. 18, 2022).

Ryan, Thomas et al., Proceedings of Thermal Treatment of Tissue with Image Guidance, Progress in Biomedical Optics, vol. 3594 (1999).

Ryan, Thomas P., Thermal Treatment of Tissue with Image Guidance; Ultrasound Catheters For Circumferential Cardiac Ablation 1999.

(56)        References Cited

OTHER PUBLICATIONS

Sakakura, Kenichi et al., Anatomic Assessment of Sympathetic Peri-Arterial Renal Nerves in Man, Journal of the American College of Cardiology, vol. 64, No. 7, 635-643 (2014).

Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.

Sanchez-Quintana, Damian et al., How close are the phrenic nerves to cardiac structures? Implications for cardiac interventionalists, 16 J. Cardiovasc. Electrophysiol 309 (2005) ("Sánchez-Quintana").

Sato, Yu, et al., "Translational Value of Preclinical Models for Renal Denervation: a histological comparison of human versus porcine renal nerve anatomy," EuroIntervention, 18, e1120-e1128, 2023.

Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH. 0b013e328344db3a.

Schmieder, Ronald E., Renal denervation in patients with chronic kidney disease: current evidence and future perspectives, Nephrol. Dial. Transplant. gfac189 (2022).

Schneider, Peter, Endovascular Skills: Guidewire and Catheter Skills for Endovascular Surgery, 2nd ed., Marcel Dekker, Inc., New York, NY (2003).

Schneider, Peter A., Endovascular Skills, Quality Medical Publishing, Inc., 1998 ("Schneider").

Schmidt, Boris, et al., "Pulmonary Vein Isolation by High Intensity Focused Ultrasound," Indian Pacing and Electrophysiology Journal, pp. 126-133 (2006).

Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.

Shimizu, Kazumasa et al., Sympathetic Dysfunction in Heart Failure, Bailliere's Clinical Endocrinology and Metabolism, vol. 7, No., 2 (1993).

Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").

Slide deck from Medtronic Circulatory System Devices Panel Meeting, General Issues Panel: Clinical Evaluation of Anti-Hyperintensive Devices (Dec. 5, 2018).

Smithwick, R. H., et al., "Splanchnicectomy for essential hypertension." J. Am. Med. Assoc., 152:1501-1504 (1953).

Stella, A., et al. "Effects of reversible renal denervation on haemodynamic and excretory functions of the ipsilateral and contralateral kidney in the cat." J Hypertension, 4: 181-188 (1986)("Stella").

Stipulation Modifying Schedule, dated Dec. 30, 2022 in the Patent Trial and Appeal Board, United States Patent and Trademark Office, Petition No. PTAB-IPR2022-00431.

Stipulation Modifying Schedule, dated Feb. 16, 2023 in the Patent Trial and Appeal Board, United States Patent and Trademark Office, Petition No. PTAB-IPR2022-00431.

Stoeckel, D. et al., A Survey of Stent Designs, Min Invas Ther & Allied Technol 2002: 11(4) 137-147 (2002).

Swartz, John F. et al., Radiofrequency Endocardial Catheter Ablation of Accessory Atrioventricular Pathway Atrial Insertion Sites, 87 Circulation 487 (1993).

Tank, J. et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07. 012.

Tanaka, Kazushi et al., "A New Radiofrequency Thermal Balloon Catheter for Pulmonary Vein Isolation," Journal of the American College of Cardiology vol. 38, No. 7, 2001.

Teigen et al., Segmental Renal Artery Embolization for Treatment of Pediatric Renovascular Hypertension, J. Vasco Interv. Radiol. 3, 111-7 (1992).

Thatipelli, Mallik R., et al., CT angiography of renal artery anatomy for evaluating embolic protection devices, 18 J. Vasc. Interv. Radiol. 842 (2007).

The Doctors and Experts at WebMD, Webster's New World Medical Dictionary (3rd ed. 2008) ("WebsterMD").

Transcript of the Mar. 2, 2023 deposition of Dr. John Moriarty.

Transcript of the Mar. 3, 2023 deposition of Dr. Chris Daft.

Transcript of deposition of the Jan. 1, 2023 deposition of Dr. Robert Tucker.

Transcript of the Jan. 14, 2023 deposition of Dr. Daniel van der Weide.

Transcript of the Sep. 30, 2022 deposition of Dr. Chris Daft.

Transcript of the Oct. 1, 2022 deposition of Dr. Farrell Mendelsohn.

Tsao, Hsuan-Ming et al., Evaluation of Pulmonary Vein Stenosis after Catheter Ablation of Atrial Fibrillation, 6 Card. Electrophysiol. Rev. 397 (2002).

Turner, et al., "Initial Experience Using the Palmaz Corinthian Stent for Right Ventricular Outflow Obstruction in Infants and Small Children", Catheterization and Cardiovascular Interventions 51:444-449 (2000).

Uchida, et al., "Effect of radiofrequency catheter ablation on para-sympathetic denervation: A comparison of three different ablation sites." PACE, 21 :2517- 2521 (1998).

Ulmsten, Ulf et al., "The Safety and Efficacy of Meno TreatTM, a new balloon device for thermal endometrial ablation," Acta Obstet Gynecol Scand 2001; 80: 52-57.

Vaezy, Shahram et al., Image-Guided Acoustic Therapy, Annual Review Biomedical Engineering, vol. 3, 375-390 (2001).

Valente, John F. et al., Laparoscopic renal denervation for intractable ADPKD-related pain, 16 Nephrol. Dial. Transplant. 160 (2001).

Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").

Wanchoo, Nishey, Medtronic Gets European and Australian Approval for Symplicity Spyral Multi-Electrode Renal Denervation Catheter, Medgadget (2013).

Weinstock, Marta et al., "Renal Denervation Prevents Sodium Retention and Hypertension in Salt-Sensitive Rabbits with Genetic Baroreflex Impairment", 90 Clinical Science 287 (1996).

Xu, J. et al., "A Bidirectional Neuromodulation Technology for Nerve Recording and Stimulation, Micromachines," vol. 9, 1 1 538. Oct. 23, 2018. doi:10.3390/mi9110538.

Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.

Zazgornik, "Bilateral Nephrectomy: The best, but often overlooked, treatment for refractory hypertension in hemodialysis patients," Am. J. Hypertension, 11:1364-1370 (1998).

Ziegler et al., Sources of Urinary Catecholamines in Renal Denervated Transplant Recipients, 8 J. Hypertension No. 10, 927 (1990).

U.S. Appl. No. 17/453,636, filed Nov. 4, 2021, File History.

U.S. Appl. No. 10/408,665, File History.

U.S. Appl. No. 60/624,793, File History.

U.S. Appl. No. 60/370,190, File History.

U.S. Appl. No. 60/415,575, File History.

U.S. Appl. No. 60/442,970, File History.

U.S. Appl. No. 60/616,254, File History.

U.S. Appl. No. 60/747,137, File History.

U.S. Appl. No. 60/808,306, File History.

U.S. Appl. No. 60/816,999, File History.

U.S. Appl. No. 61/405,472, File History.

U.S. Appl. No. 11/532,814, Non-Final Office Action mailed Mar. 29, 2012.

U.S. Appl. No. 14/683,966, Non-Final Office Action mailed Jun. 12, 2017, 14 pgs.

U.S. Appl. No. 14/683,966, Response filed Nov. 10, 2017 to Non-Final Office Action mailed Jun. 12, 2017, 13 pgs.

(56)                  References Cited

OTHER PUBLICATIONS

U.S. Appl. No. 14/683,966, Notice of Allowance mailed Jan. 31, 2018, 8 pgs.
U.S. Appl. No. 14/683,966, PTO Response to Rule 312 Communication mailed Mar. 29, 2018, 2 pgs.
U.S. Appl. No. 14/683,966, 312 Amendment filed Mar. 13, 2018, 10 pgs.
U.S. Appl. No. 14/683,966, Corrected Notice of Allowance mailed May 22, 2018, 4 pgs.
U.S. Appl. No. 15/204,349, Preliminary Amendment filed Nov. 30, 2016, 3 pgs.
U.S. Appl. No. 15/204,349, Restriction Requirement mailed May 17, 2018, 7 pgs.
U.S. Appl. No. 15/204,349, Response filed Jun. 5, 2018 to Restriction Requirement mailed May 17, 2018, 7 pgs.
U.S. Appl. No. 15/204,349, Non-Final Office Action mailed Nov. 27, 2018, 14 pgs.
U.S. Appl. No. 15/204,349, Response filed Feb. 27, 2019 to Non-Final Office Action mailed Nov. 27, 2018, 10 pgs.
U.S. Appl. No. 15/204,349, Final Office Action mailed Apr. 22, 2019, 16 pgs.
U.S. Appl. No. 15/204,349, Response filed Jun. 24, 2019 to Final Office Action mailed Apr. 22, 2019, 12 pgs.
U.S. Appl. No. 15/204,349, Advisory Action mailed Jul. 9, 2019, 5 pgs.
U.S. Appl. No. 15/261,732, Notice of Allowance dated Sep. 25, 2018.
U.S. Appl. No. 15/299,694, Restriction Requirement mailed Aug. 6, 2018, 6 pgs.
U.S. Appl. No. 15/299,694, Response filed Oct. 8, 2018 to Restriction Requirement mailed Aug. 6, 2018, 7 pgs.
U.S. Appl. No. 15/299,694, Non-Final Office Action mailed Nov. 27, 2018, 15 pgs.
U.S. Appl. No. 15/299,694, Response filed Feb. 27, 2019 to Non-Final Office Action mailed Nov. 27, 2018, 10 pgs.
U.S. Appl. No. 15/299,694, Final Office Action mailed Apr. 22, 2019, 16 pgs.
U.S. Appl. No. 15/299,694, Response filed Jun. 24, 2019 to Final Office Action mailed Apr. 22, 2019, 11 pgs.
U.S. Appl. No. 15/299,694, Advisory Action mailed Jul. 9, 2019, 5 pgs.
U.S. Appl. No. 15/943,354, Preliminary Amendment filed Apr. 3, 2018, 9 pgs.
U.S. Appl. No. 15/943,354, Restriction Requirement mailed Nov. 20, 2019, 8 pages.
U.S. Appl. No. 15/943,354, Response filed Dec. 19, 2019 to Restriciton Requirement mailed Nov. 20, 2019, 8 pages.
U.S. Appl. No. 15/943,354, Non-Final Office Action mailed Jan. 13, 2020, 6 pages.
U.S. Appl. No. 15/943,354, Non-Final Office Action mailed Apr. 20, 2020, 7 pages.
U.S. Appl. No. 15/996,978, Preliminary Amendment filed Jun. 5, 2018, 11 pgs.
U.S. Appl. No. 15/996,978, Restriction Requirement mailed Feb. 7, 2020, 7 pages.
U.S. Appl. No. 15/996,978, Response filed Apr. 6, 2020 to Restriction Requirement mailed Feb. 7, 2020, 8 pages.
U.S. Appl. No. 15/996,978, Restriction Requirement mailed Apr. 16, 2020, 8 pages.
U.S. Appl. No. 15/996,978, Response filed May 1, 2020 to Restriction Requirement mailed Apr. 16, 2020, 8 pages.
U.S. Appl. No. 15/996,978, Non-Final Office Action mailed Jun. 11, 2020, 8 pages.
U.S. Appl. No. 16/219,874, Final Office Action mailed Dec. 21, 2020, 7 pages.
U.S. Appl. No. 16/517,180, Preliminary Amendment filed Jul. 19, 2019, 12 pgs.
U.S. Appl. No. 17/453,636, filed Nov. 4, 2021.
File History of U.S. Appl. No. 12/754,337.
File History to U.S. Pat. No. 9,943,666.
File History to U.S. Pat. No. 9,981, 108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-Final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.
Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.

* cited by examiner

502 ─┐
| ADVANCE A DISTAL REGION OF A TISSUE TREATMENT SYSTEM INTO A TARGET VESSEL |

504 ─┐
| INFLATE THE BALLOON AGAINST THE VESSEL WALL |

506 ─┐
| DELIVER ULTRASONIC ENERGY FROM THE TRANSDUCER TO THE VESSEL WALL |

CATHETER HAVING COMPLIANT BALLOON

This application claims the benefit of priority under 35 U.S.C. § 119(e) to U.S. Provisional Application No. 63/223,517, filed Jul. 19, 2021, titled ONE-SIZE-FITS-ALL RENAL ARTERY TREATMENT SYSTEM and U.S. Provisional Application No. 63/367,119 filed Jun. 27, 2022, titled CATHETER HAVING COMPLIANT BALLOON all of which are incorporated herein by reference in their entireties to provide continuity of disclosure.

BACKGROUND

Field

This application relates generally to minimally-invasive devices, systems and methods of delivering energy to a targeted anatomical location of a subject, and more specifically, to catheter-based, intraluminal devices and systems configured to deliver ultrasonic energy to treat tissue, such as nerve tissue.

Background Information

According to the Centers for Disease Control and Prevention (CDC), about one in every three adults suffer from high blood pressure, also known as hypertension. Left untreated, hypertension can result in renal disease, arrhythmias, and heart failure. In recent years, the treatment of hypertension has focused on interventional approaches to inactivate the renal nerves surrounding the renal artery. Autonomic nerves tend to follow blood vessels to the organs that they innervate. Catheters may reach specific structures, such as the renal nerves, that are proximate to the lumens in which the catheters travel. Accordingly, catheter-based systems can deliver energy from within the lumens to inactivate the renal nerves.

One approach to renal nerve deactivation employs a radio frequency (RF) generator connected to a catheter having multiple electrodes placed against the intima of the renal artery and used to create an electrical field in the vessel wall and surrounding tissue that results in resistive (ohmic) heating of the tissue to a temperature sufficient to ablate the tissue and the renal nerve passing through that tissue. To treat all the renal nerves surrounding the renal arteries, the RF electrodes are repositioned several times around the inside of the renal artery. However, the relatively confined electric fields created by the RF electrodes may miss some of the renal nerves, leading to an incomplete treatment. Additionally, to heat the renal nerves, the RF electrodes must contact the intima, posing a risk of damage or necrosis to the intima, which in turn can lead to thrombus formation, fibrosis of the vessel wall, mechanical weakening of the vessel, and possible vessel dissection.

Another approach to renal nerve deactivation is the use of high-intensity focused ultrasound (HIFU). HIFU relies on vibrational energy to cause frictional heating and disruption of the tissue, and in turn, raise the tissue temperature sufficiently to cause ablation or remodeling.

U.S. Pat. Nos. 9,943,666, 9,981,108, and 10,039,901 to Warnking, U.S. Pat. Nos. 9,700,372, 9,707,034, and 10,368,944 to Schaer, and U.S. Pat. Nos. 10,350,440 and 10,456,605 to Taylor, the entire contents of each of which is incorporated by reference herein, solve many of the drawbacks of RF and HIFU systems. An example embodiment of the system includes an ultrasound transducer positioned along a distal end of a catheter designed to be inserted into a blood vessel, e.g., a renal artery. Electrical cabling, which is received within a cabling lumen of the catheter, can be used to power the ultrasound transducer. The ultrasound transducer emits one or more therapeutic doses of unfocused ultrasound energy, which heats the tissue adjacent to the body lumen within which the transducer is disposed. Such unfocused ultrasound energy may, for example, ablate target nerves surrounding that body lumen, but without damaging non-target tissue such as the inner lining of the body lumen or unintended organs outside of the body lumen. The system may include a balloon mounted at the distal end of the catheter that is designed to cool the blood vessel when a cooling fluid is delivered to the balloon. Such a design enables creation of one or more ablation zones sufficient to achieve long-term nerve inactivation at different locations around the circumference of the blood vessel.

SUMMARY

The present invention is defined in the independent claims. Further embodiments of the invention are defined in the dependent claims.

A catheter is provided herein. The catheter comprises a catheter shaft having a fluid channel, an ultrasound transducer, and a compliant balloon mounted on the catheter shaft and having an interior in fluid communication with the fluid channel and containing the ultrasound transducer. The compliant balloon includes a balloon wall having a working section radially surrounding the ultrasound transducer. The compliant balloon can include a balloon wall having a working section radially surrounding the ultrasound transducer, a proximal shoulder proximal to the working section, and a distal shoulder distal to the working section where the balloon wall is thicker at the proximal shoulder and the distal shoulder than at the working section. The working section has a predetermined straightness when the working section has a first diameter and when the working section has a second diameter that is at least 2 mm greater than the first diameter.

A method is provided herein. The method includes advancing the catheter into a target vessel having a vessel wall, and inflating the compliant balloon to an inflation pressure against the vessel wall. Ultrasonic energy is delivered from the ultrasonic transducer to the vessel wall.

A kit is provided herein. The kit includes a first catheter and a second catheter, each of which covers a different, and overlapping, inflation diameter range. The first catheter can include a first compliant balloon that has a first inflation diameter range when fluid is circulated through the balloon at a flow rate to cause an inflation pressure in a range of 10 to 30 psi. The second catheter can include a second compliant balloon that has a second inflation diameter range when fluid is circulated through the balloon at a flow rate to cause the inflation pressure in a range of 10 to 30 psi. The first inflation diameter range can overlap the second diameter range. Accordingly, the kit can be used to treat vessel sizes over a wide range, e.g., from 3 to 9 mm, by selecting the catheter having the inflation diameter range that corresponds to the target anatomy.

The above summary does not include an exhaustive list of all aspects of the present invention. It is contemplated that the invention can be practiced from all suitable combinations of the various aspects summarized above, as well as those disclosed in the Detailed Description below and particularly pointed out in the claims. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Figure 1:
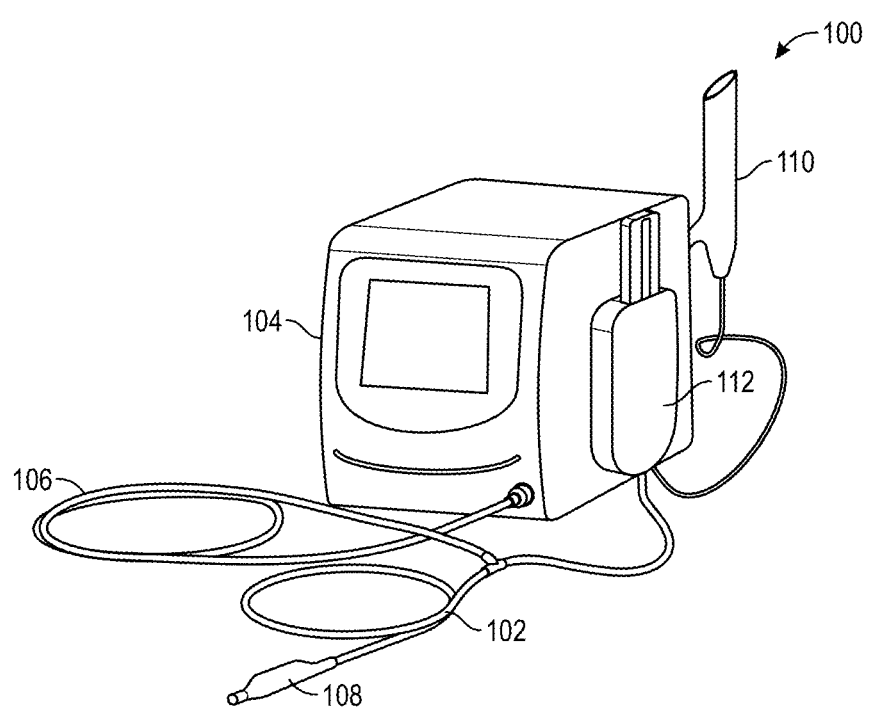
FIG. 1 is a perspective view of a tissue treatment system, in accordance with an embodiment.

Embodiments describe a tissue treatment system having a compliant balloon, and methods of using the tissue treatment system. The tissue treatment system may be an acoustic-based tissue treatment system, e.g., an ultrasound-based tissue treatment system, used to delivery unfocused ultrasonic energy radially outwardly to heat, and thus treat, tissue within a target anatomical region. The unfocused ultrasonic energy may target select nerve tissue within the anatomical region, and may heat such tissue in such a manner as to neuromodulate, e.g., fully or partially ablate, necrose, or stimulate, the nerve tissue. The tissue treatment system can therefore be used to neuromodulate renal nerves to treat hypertension, chronic kidney disease, atrial fibrillation, or other medical conditions. Alternatively, the tissue treatment system may be used in other applications, such as to treat sympathetic nerves of the hepatic plexus within a hepatic artery responsible for blood glucose levels important to treating diabetes. Thus, reference to the system as being a renal denervation system, or being used in treating, e.g., neuromodulating, renal nerve tissue is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a tissue treatment system. Similarly, "proximal" may indicate a second direction opposite to the first direction. Such terms are provided to establish relative frames of reference, however, and are not intended to limit the use or orientation of a tissue treatment system to a specific configuration described in the various embodiments below.

Some existing catheter-based systems used for renal denervation employ non-compliant balloons to center a transducer within a target vessel, and to contain a circulating cooling fluid that protects the target vessel from being ablated by energy delivered from the transducer. The non-compliant balloons expand to roughly a predetermined diameter over an operating range of inflation pressures. More particularly, the non-compliant balloons have a narrow range of inflation diameters over a range of operating pressures. The non-compliant balloons target a narrow range of vessel lumen diameters, and thus, different device sizes are needed to treat differently sized patient anatomies. Given that the size of a renal artery can change not only from patient to patient, but also between left and right renal arteries of a same patient, or even along a length of a single renal artery of a patient, a substantial portfolio of device sizes may be needed to treat the general patient population. Accordingly, existing catheter-based systems that include non-compliant balloons require significant shelf space to stock the portfolio of device sizes. The large product portfolio also creates manufacturing complexities associated with producing a wide range of different device models. The device customer and the device manufacturer can benefit from a catheter-based system used for renal denervation that can treat a wide range of vessel lumen diameters with a same and/or better safety and efficacy profile as existing devices. Such a catheter-based system is described herein.

In an aspect, a tissue treatment system is provided. The system includes a compliant balloon and a transducer mounted on a catheter shaft. The compliant balloon has a balloon wall shaped to center the catheter shaft and the transducer within a target vessel when expanded into apposition with a vessel wall. The balloon wall has a working section radially surrounding the ultrasound transducer, a proximal shoulder proximal to the working section, and a distal shoulder distal to the working section and the balloon wall is thicker at the proximal shoulder and the distal shoulder than at the working section. More particularly, despite the balloon flexibility that allows the compliant balloon to expand into apposition with a wide range of vessel sizes, the catheter shaft and the transducer are adequately supported and centered in the target vessel. The compliant and supportive balloon allows for a single device to treat target vessels having varied lumen diameters. Thus, the single device can accommodate varied vessel lumen diameters in a same patient (left renal artery to right renal artery, or along a same renal artery) and from patient to patient. The compliant and supportive balloon can allow for a single device to be used per procedure, which can reduce a number of device exchanges required, and hence, can decrease procedure time and complexity, as well as cost. Accordingly, the tissue treatment system having a compliant balloon, as described below, can reduce a number of catheters and a procedural time required per procedure, as compared to existing catheter-based systems used for renal denervation.

The catheter-based system can have a stable run-to-run compliance curve that provides for repeatable and controllable expansion within a range of vessel sizes. After each inflation, a compliance curve of a compliant balloon may change. In order to treat a patient using only one catheter, the catheter-based system described herein includes a compliance curve that does not significantly change between inflations and/or changes in a controlled/known manner. The stable compliance curve allows for the system to be inflated several times within several locations of a vessel, yet be predictably sized to ensure good apposition with the vessel wall and uniform energy delivery. Furthermore, the stable compliance curve can reduce software complexity because a controller used to control inflation of the system can be programmed to inflate the balloon based on the stable compliance curve.

Supporting and centering a transducer in a blood vessel can contribute to uniform energy delivery. The pressure of the balloon of an ultrasound ablation catheter may, however, fluctuate as a function of the required flow rate and/or the diameter of the blood vessel being treated. At higher pressures, e.g., used in larger diameter blood vessel and/or during higher flow rate conditions, it may be easier for a larger range of compliant balloon materials to center the transducer. But under lower pressure conditions, e.g., in smaller blood vessels and/or lower flow rate conditions, the same compliant balloon may not sufficiently center the transducer. The catheter-based system described below can support and center the ultrasound transducer over an operating range of pressures and within a range of vessel sizes in order to enable more uniform ablations circumferentially around a blood vessel. More particularly, the catheter-based system can include a balloon capable of centering the ultrasound transducer both within smaller vessels at lower inflation pressures and within larger vessels at higher inflation pressures.

A radial access catheter can be less painful to insert, is associated with fewer complications such as bleeding and infection at an access site, and can decrease an overall treatment time. Patients may be discharged on the same day as treatment. The catheter-based system described below can provide a balloon compatible with a guide sheath configured to be inserted via a radial blood vessel of an arm. For example, a balloon of the system can have a crossing-profile that is less than 5 French, less than 0.060 inch (0.1524 cm), and/or less than 0.058 inch (0.14732 cm). Furthermore, the balloon may have a crossing-profile that is 4 French.

The system described below can provide an ultrasound ablation treatment that is consistently safe and effective. To achieve this end, a balloon is described that does not significantly interfere with sonication of a transducer. In certain embodiments, a balloon is provided consisting of material and a selective thickness such that the balloon does not interfere with an energy transmission of a transducer.

In certain embodiments, a compliant balloon that is arterial limiting is provided. In certain arterial limited embodiments, balloon material is chosen such that the wrinkles of the balloon do not interfere with the sonication. In certain arterial limited embodiments, balloon material is chosen such that the balloon wrinkles in a predictable manner such that the energy profile may be adjusted so that the wrinkles do not interfere with the sonication of the transducer.

A tissue treatment system including a catheter having a compliant medical balloon configured for use in a wide range of vessel lumen diameters is provided herein. In an embodiment, the compliant balloon is mounted on a catheter shaft and has an interior containing an ultrasound transducer. The compliant balloon may be formed from a material, and have a structure, that enables the balloon to expand into apposition with a wide range of body lumens. For example, the compliant balloon can be formed from a polyether-based thermoplastic polyurethane, and have a working section that has a predetermined straightness over a range of inflation diameters. The range of inflation diameters can include several diameters that are at least 2 mm different. For example, a first diameter can be in a range of 3.5 to 6 mm, e.g., 5 mm, and a second diameter can be in a range of 8 to 9 mm, e.g., 8.5 mm.

As used herein, an inflation diameter refers to an outer diameter of a cross-sectional shape of the balloon, passing through a center of the transducer. More particularly, a transverse plane oriented orthogonal to a central axis of the balloon can intersect the balloon at an outer profile of the balloon. The outer dimension, e.g., outer diameter, of that profile represents the inflation diameter of the balloon. In an embodiment, the outer diameter can be measured by inflating the balloon, and measuring the outer dimension at the balloon surface radially outward from the transducer. For example, the balloon can be supported and inflated in free space to a given inflation pressure, and a measurement tool, such as a laser caliper, can be used to measure the outer diameter of the inflated balloon.

The predetermined straightness of the working section of the balloon can support and center the transducer within a target vessel. In an embodiment, the predetermined straightness includes a cylindricity of the working section being less than a predetermined threshold, e.g., 1 mm. Straightness can be determined with respect to other geometric characterizations, such as a ratio of a radius of curvature of the working section to a length of the compliant balloon, or a ratio of radiuses of curvature of the working section at different inflation diameters. The predetermined straightness of the compliant balloon can compare favorably in terms of tissue contact and transducer support, as compared to typical compliant balloons that tend toward a spherical profile when inflated.

Referring to FIG. 1, a perspective view of selected components of a tissue treatment system is shown in accordance with an embodiment. A tissue treatment system 100 may be a catheter-based system. More particularly, the system can include a catheter 102 that can be delivered intraluminally, e.g., intravascularly, to a target anatomical region of a subject. When so placed, a transducer of the system (FIG. 2A) can be positioned within a target anatomy, e.g., within a body lumen such as a blood vessel. As described below, the transducer can be an ultrasound transducer that may be disposed within a medical balloon 108. The transducer can be activated to deliver unfocused ultrasonic energy radially outwardly so as to suitably heat, and thus treat, tissue within the target anatomical region. The transducer can be activated at a frequency, time, and energy level suitable for treating the targeted tissue.

The tissue treatment system 100 may include the catheter 102, a controller 104, and a connection cable 106. In certain embodiments, the tissue treatment system 100 optionally further includes a balloon 108 (or other suitable expandable member), a reservoir 110, a cartridge 112, and a control mechanism, such as a handheld remote control. In certain embodiments, the controller 104 is connected to the catheter 102 through the cartridge 112 and the connection cable 106. In certain embodiments, the controller 104 interfaces with the cartridge 112 to provide cooling fluid to the catheter 102 for inflating and deflating the balloon 108.

In an embodiment, a balloon catheter 102 can include a compliant balloon 108 configured to accommodate a range of target vessel sizes, as described below. The compliant balloon 108 can accommodate differences in vessel lumen diameter along the artery length and between left and right renal arteries. For example, the compliant balloon 108 may be configured to treat a blood vessel having a vessel lumen diameter between 3 to 9 mm in diameter. Thus, the compliant balloon 108 can mitigate the need to use several different balloon catheters 102 per procedure. Accordingly, the balloon 108 can reduce procedure times and complexity.

Figure 2A:
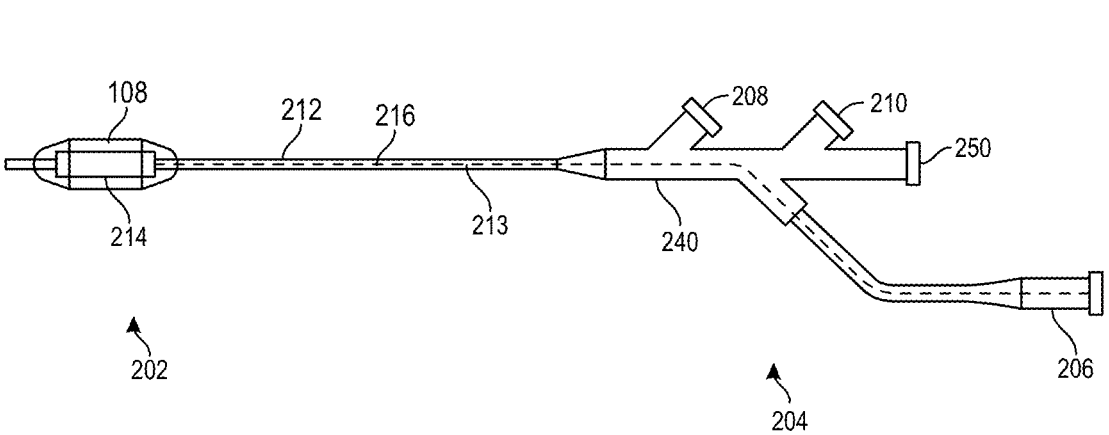
FIG. 2A is a side view of selected components of the tissue treatment system of FIG. 1, in accordance with an embodiment.

Referring to FIG. 2A, a side view of selected components of the tissue treatment system of FIG. 1 is shown in accordance with an embodiment. The tissue treatment catheter 102 can include a distal region 202 and a proximal region 204. The catheter 102 may have a length that depends on a treatment application. For example, in certain embodiments suitable for, e.g., renal denervation through a femoral access delivery method, the catheter 102 can have a working length (measured from a distal tip of the catheter 102 to a proximal hub 240 of the catheter 102) of 80 to 90 cm, e.g., 85 cm, in the femoral access delivery method. In embodiments suitable for, e.g., renal denervation through a radial access delivery method, the catheter 102 can have a working length of a comparatively longer length. More particularly, the working length can be 150 to 160 cm, e.g., 155 cm. Furthermore, an overall length of the catheter 102 for such application, including a length of cabling extending to an electrical coupling 206, can be longer. More particularly, the cabling can have a length of about 305 cm from the proximal hub 240 to the electrical coupling 206.

The catheter 102 can have a profile that is suitable to accessing a renal artery through the femoral and radial access locations. For example, the catheter 102 may be 4 to 6 French in diameter, e.g., 5 French. The profile is facilitated in part by a catheter shaft 212 having an outer diameter in a range of 0.050 to 0.060 inch, e.g., 0.057 inch.

The distal region 202 of the tissue treatment system 100 may be a portion of the device that is advanced into a target anatomy, e.g., a target vessel having a vessel wall, to treat the target vessel. The distal region 202 can include the balloon 108 mounted on a catheter shaft 212. The balloon 108 can be a compliant balloon having the characteristics described in detail below. For example, the balloon 108 can have a cylindricity that supports and centers a transducer 108 within a range of vessel diameters, and thus, contributes to uniform energy delivery.

The catheter shaft 212 can be an elongated tubular structure that extends longitudinally from a proximal end to a distal end. The balloon 108 can be mounted and supported on the catheter shaft 212 at the distal end. Furthermore, the ultrasound transducer 214 can be mounted on the catheter shaft 212 and contained within the balloon 108. Accordingly, the catheter shaft 212 can facilitate delivery of a cooling fluid to the balloon 108 and delivery of electrical energy to the transducer 104.

The catheter shaft 212 can include one or more lumens (FIG. 4) that may be used as fluid conduits, electrical cabling passageways, guidewire lumens, and/or the like. In an embodiment, the catheter shaft 212 can include a guidewire lumen 213 that is shaped, sized and otherwise configured to receive a guidewire. In an embodiment, the guidewire lumen 213 is an over-the-wire type guidewire lumen, extending from a distal tip of the catheter 102 through an entire length of the catheter shaft 212 to an exit port 250 in the proximal hub 240 of the catheter 102. As described below, the lumen(s) of the catheter shaft 212 may also communicate inflation/cooling fluid from the proximal region 204 to the balloon 108 during balloon expansion.

In an embodiment, a transducer 214 is mounted on the catheter shaft 212 at the distal region 202, within an interior of the balloon 108. The transducer 214 can be an ultrasound transducer 214 used to emit energy toward the vessel wall. For example, the transducer 214 can emit ultrasound energy circumferentially, e.g., 360 degrees, around the vessel wall. In an embodiment, electric cabling 216 extends from the proximal region 204 to the distal region 202, and is connected to the transducer 214 to generate energy for emission to target tissue.

The ultrasound transducer 214 may include first and second electrodes that are arranged on either side of a cylindrical piezoelectric material, such as lead zirconate titanate (PZT). To energize the transducer 214, a voltage is applied across the first and the second electrodes at frequencies selected to cause the piezoelectric material to resonate, thereby generating vibration energy that is emitted radially outward from the transducer 214. The transducer 214 is designed to provide a generally uniform and predictable emission profile, to inhibit damage to surrounding non-target tissue. In addition, a cooling fluid is circulated through the balloon 108, both prior to, during, and after activation of the transducer 214, so as to reduce heating of an inner lining of the body lumen and to cool the transducer 214. In this manner, the peak temperatures achieved by tissue within the cooling zone remain lower than for tissue located outside the cooling zone.

The proximal region 204 may include one or more connectors or couplings. The connectors or couplings can be electrically connected to the transducer 214 via the electric cabling 216. For example, the proximal region 204 may include one or more electrical coupling 206 that connects to a proximal end of the electric cabling 216. A distal end of the electric cabling 216 can be connected to the transducer 214.

The catheter 102 may be coupled to the controller 104 by connecting the electrical coupling 206 to the connection cable 106. The connection cable 106 may be removably connected to the controller 104 and/or the catheter 102 via a port on the controller 104 and/or the catheter 102. Accordingly, the controller 104 can be used with several catheters 102 during a procedure by disconnecting the coupling of a first catheter, exchanging the first catheter with a second catheter, and connecting a coupling of the second catheter to the controller 104. In certain embodiments, e.g., where only one catheter needs to be used during a procedure, the connection cable 106 may be permanently connected to the controller 104.

In certain embodiments, the proximal region 204 of the catheter 102 may further include one or more fluidic ports. For example, the proximal hub 240 can include a fluidic inlet port 208 and a fluidic outlet port 210, via which an expandable member, e.g., the balloon 108, may be fluidly coupled to the reservoir 110 (FIG. 1). The reservoir 110 can therefore supply cooling fluid to the balloon 108 through the fluidic ports. The reservoir 110 optionally may be included with the controller 104, e.g., attached to the outer housing of the controller 104 as shown in FIG. 1. Alternatively, the reservoir 110 may be provided separately.

Figure 2B:
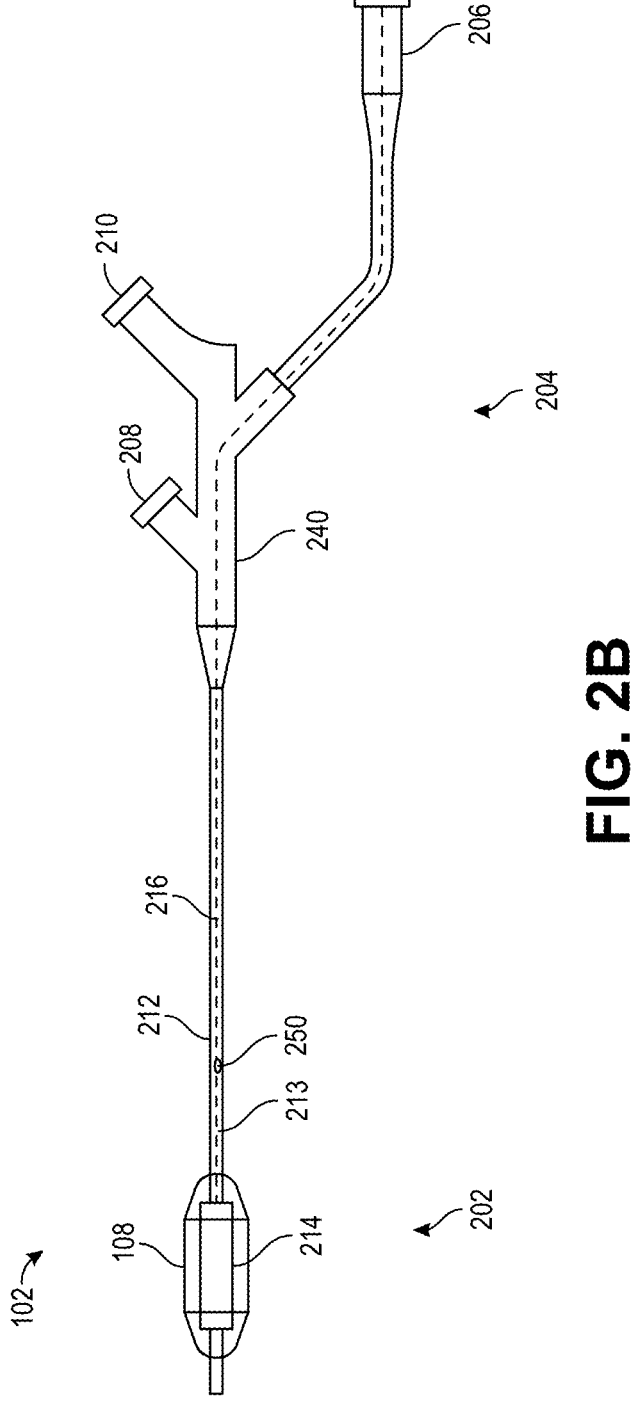
FIG. 2B is a side view of selected components of the tissue treatment system of FIG. 1, in accordance with an embodiment.

Referring to FIG. 2B, a side view of selected components of the tissue treatment system of FIG. 1 is shown in accordance with an embodiment. In an embodiment, the catheter 102 can have a rapid-exchange type guidewire lumen 213. More particularly, the guidewire lumen 213 can extend from the distal tip of the catheter 102 through a partial length of the catheter shaft 212 to an exit port 250 in the distal portion 202 of the catheter 102. For example, a distance from the distal tip to the rapid exchange port 250 may be in a range of 20 to 30 cm, e.g., 23 cm. The proximal hub 240 illustrated in FIG. 2B may differ from the proximal hub 240 illustrated in FIG. 2A, given that the exit port 250 may be moved from the proximal portion 204 to the distal portion 202. Other components of rapid exchange version of the catheter 102 may be similar to those of the over-the-wire version of the catheter 102, and thus, the descriptions of the components illustrated in FIG. 2A can apply to similarly numbered components illustrated in FIG. 2B.

Figure 3:
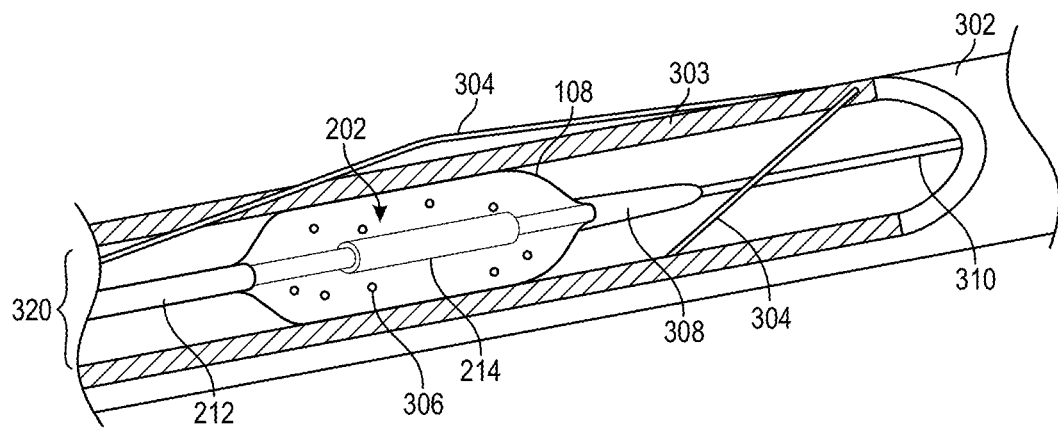
FIG. 3 is a perspective view of selected components of the tissue treatment system of FIG. 1 inserted into a body lumen, in accordance with an embodiment.

Referring to FIG. 3, a perspective view of additional selected components of the tissue treatment system of FIG. 1 inserted into a body lumen is shown in accordance with an embodiment. The tissue treatment system 100 can be inserted into a body lumen of a subject. For example, a distal region 202 of the catheter 102 of the tissue treatment system 100 can be advanced into a target vessel 302, e.g., a blood vessel such as a renal artery. The target vessel 302 can have a plurality of nerves 304 in an outer layer, e.g., an adventitia layer, of the target vessel 302. In an embodiment, the tissue treatment system 100 includes a guidewire support tip 308 having a lumen that connects to the guidewire lumen 213 of the catheter shaft 212. The support tip 308 can receive the guidewire 310 to allow the device to be tracked over a guidewire 310 to the target anatomy.

When the distal region 202 is disposed in the vessel lumen of the target vessel 302, the transducer 214 and the balloon 108 (or another suitable expandable member) are positioned radially inward from the plurality of nerves 304. The transducer 214 may be disposed partially or completely within the interior of the balloon 108. The balloon 108 can be filled with an inflation fluid 306, e.g., a cooling fluid, to expand the balloon 108. When the balloon 108 is inflated with the inflation fluid 306, the balloon 108 can contact an interior surface, e.g., an intima, of the target vessel. The expanded balloon 108 may therefore have an inflated diameter equal to a lumen diameter 320 of the target vessel 302, and appose the target vessel 302 and center the transducer 214 within the target vessel 302.

In certain embodiments, the transducer 214 may be programmed to output an acoustic signal when the balloon 108 fully occludes the target lumen. The balloon 108 may center the transducer 214 within the target lumen. In certain embodiments, e.g., suitable for renal denervation, the balloon 108 may be a compliant balloon 108, as described below, which may be inflated in the patient during a procedure at a working pressure of about 1.4 to 2 atm using the inflation fluid 306. The balloon 108 is sized for insertion in the target lumen and, in the case of insertion of the renal artery, for example, the balloon 108 may be selected to have expansion sizes including outer diameters of one or more of 3.5 mm, 4.2 mm, 5 mm, 6 mm, 7 mm, 8 mm, or 9 mm. The balloon 108 may have a burst strength of greater than 45 psi.

In some embodiments, when inflated by being filled with the inflation fluid 306 under the control of the controller 104 within the target vessel 302, a balloon wall of the balloon 108 may be generally parallel with an outer surface of the transducer 214. Optionally, the balloon 108 may be inflated sufficiently as to be in apposition with the target vessel. For example, when inflated, the balloon 108 may at least partially contact, and thus be in apposition with, the inner wall of the target vessel. In other embodiments, the balloon 108 is configured not to contact the target vessel when expanded. The balloon 108 may be maintained at a specified size by pushing fluid into, e.g., via the inlet port 208, and pulling fluid out of, e.g., via the outlet port 210, the balloon 108 at a specified flow rate. More particularly, the inflation fluid 306 can circulate within the balloon 108 to expand the balloon 108.

Figure 4:
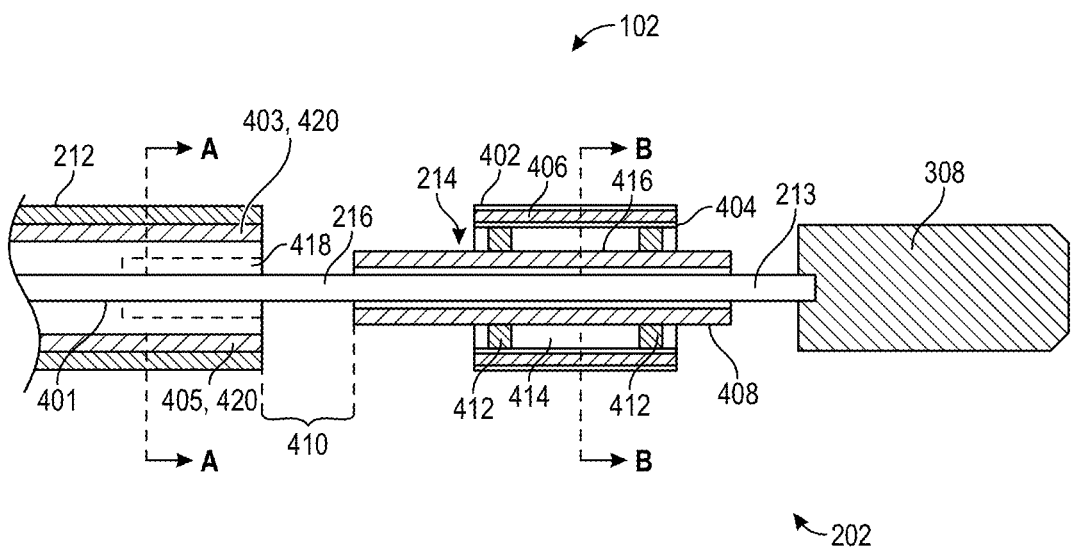
FIG. 4 is a longitudinal cross-sectional view of a distal region of a tissue treatment system, in accordance with an embodiment.

Referring to FIG. 4, a longitudinal cross-sectional view of the distal region of a tissue treatment system is shown in accordance with an embodiment. In certain embodiments, the catheter shaft 212 may be about 1.8 mm in diameter. As described above, the catheter shaft 212 includes one or more lumens that may be used as fluid conduits, passageways for electrical cabling or the guidewire 310, etc. For example, the catheter shaft 212 may include the guidewire lumen 213 that is shaped, sized and otherwise configured to receive the guidewire 310. The catheter shaft 212 may include a cable lumen 401 (extending through a same shaft as the guidewire lumen 213) for receiving the electrical cabling, and/or fluid lumens for transferring the inflation/cooling fluid, e.g., water, sterile water, saline, 5% dextrose (D5W), other liquids or gases, etc., from and to a fluid source, e.g., the reservoir 110, at the proximal region 204 of the catheter 102 external to the patient. The catheter shaft 212 can include one or more fluid channels 420 to move fluid into or out of a balloon 108. For example, the fluid channel(s) can include an inlet channel 403 to deliver the inflation fluid 306 from the inlet port 208 to the balloon 108 under control of the controller 104. Similarly, the fluid channel(s) can include an outlet channel 405 to remove fluid from the balloon 108 to the outlet port 210. Accordingly, the inlet channel 403 and the outlet channel 405 are in fluid communication with the balloon 108 to circulate fluid through the balloon 108 at a flow rate selected to inflate the balloon 108. The flow rate also controls heat transfer between the balloon 108 and the vessel wall 303 to reduce a likelihood of overheating tissue during treatment. For example, the flow rate can provide for active cooling of about the first millimeter of tissue to preserve the integrity of, e.g., the renal arterial wall.

In certain embodiments suitable for, e.g., renal denervation, the guidewire 310 has a diameter of about 0.36 mm and a length of from about 180 cm to about 300 cm, and is delivered using a 7 French guide catheter 102, having a minimum inner diameter of 2.06 mm and a length less than about 80 cm. In certain embodiments, a 6 French guide catheter 102 is used to deliver the guidewire 310. In certain embodiments, the guide catheter 102 has a length of about 55 cm. In certain embodiments, the guide catheter 102 has a length of about 85 cm and a hemostatic valve is attached to the hub of the guide for continuous irrigation of the guide to decrease the risk of thromboembolism. In certain embodiments, the guidewire lumen 213 is located in the center of the catheter shaft 212 in order to center the transducer 214.

The ultrasound transducer 214 may include a cylindrical tube 402 made of a piezoelectric material, e.g., lead zirconate titanate (PZT), etc., with inner and outer electrodes 404, 406 along the inner and outer surfaces of cylindrical tube 402, respectively. In certain embodiments suitable for, e.g., renal denervation, the piezoelectric material comprises PZT-8 (Navy III). Raw PZT transducers 214 may be plated with layers of copper, nickel and gold to create electrodes on the inner and outer surfaces of the cylinder. Application of alternating current across inner and outer electrodes 406 causes the piezoelectric material to vibrate transverse to the longitudinal direction of the cylindrical tube 402 and radially emit ultrasonic waves.

In addition, the transducer 214 is generally supported via backing member or post 408. In certain embodiments, backing member 408 comprises stainless steel coated with nickel and gold, wherein nickel is used as a bonding material between the stainless steel and gold plating. In certain embodiments suitable for, e.g., renal denervation, the outer diameter of the transducer 214 is about 1.5 mm, the inner diameter is about 1 mm, and the transducer 214 has a length, for example, in a range of 3 to 9 mm, such as 6 mm. The backing member 408 may extend from the distal end of the catheter shaft 212 to the support tip 308. For example, the distal end of the backing member 408 may be positioned within an adjacent opening in the support tip 308, and the proximal end of the backing member 408 may be moveably coupled to the distal end of the catheter shaft 212 via the electrical cabling. In other embodiments, there is a gap 410 between the distal end of the catheter shaft 212 and the backing member 408 supporting the transducer 214, and/or a gap between the backing member 408 and the support tip 308.

In order to permit liquid cooling along both the inner and outer electrodes 406, the backing member 408 may include one or more stand-off assemblies 412. The stand-off assemblies may define one or more annular openings 414 through which cooling fluid may enter the space between the backing member 408 and the inner electrode 404. The backing member 408 may serve as a fluid barrier between the inflation/cooling fluid circulated within the balloon 108 and the lumen of the backing member 408 that receives the guidewire 310. The stand-off assemblies of the backing member 408 may be positioned along each end of the ultrasound transducer 214 (separated by a main post body 416) and couple the cylindrical tube 402 of the ultrasound transducer 214 to the backing member 408. The stand-off assembly 412 may have a plurality of lugs, ribs, or attachment points that engage the inner electrode 404 of the transducer 214. In certain embodiments, the attachment points are soldered to the inner electrode 404 of the transducer 214. The number, dimensions, and placement of the ribs may vary, as desired or required. For example, a total of three ribs are generally equally-spaced apart from one another at an angle of 120 degrees, defining the annular openings 414 through which fluid and blood may enter the interior space of the cylindrical tube 402 between the inner electrode 404 disposed along the inner surface of the cylindrical tube 402 and the backing member 408. In certain embodiments, the maximum outer diameter of the stand-off assemblies is about 1 mm, the outer diameter of the main post body 416 is about 0.76 mm, and the inner diameter of the backing member 408 is about 0.56 mm.

The stand-off assemblies may be electrically conductive, so as to electrically couple the inner electrode 404 of the ultrasound transducer 214 to the backing member 408. One or more conductors of the electrical cabling may be electrically coupled to the backing member 408. Thus, as the controller 104 is activated, current may be delivered from the electrical cabling to the inner electrode 404 of the ultrasound transducer 214 via the backing member 408 and the stand-off assemblies, which advantageously eliminates the need to couple the electrical cabling directly to the inner electrode 404 of the transducer 214.

In an embodiment, the backing member 408 may have an isolation tube (not shown) disposed along its interior surface so as to prevent or reduce the likelihood of electrical conduction between the guidewire 310 and the backing member 408. The isolation tube may be formed of a non-conductive material, e.g., a polymer such as polyimide. The isolation tube may extend from the distal end of the catheter shaft 212 through the lumen of the backing member 408 within the transducer 214 to the support tip 308. The transducer 214 can be mounted on the isolation tube and/or the electrical cabling. In this manner, the transducer 214 can be distally offset from the distal end of catheter shaft 212 by the gap 410.

The catheter 102 may also include a bore 418 extending from the distal end of the catheter shaft 212 proximally within the catheter 102. The bore 418 can be sized and shaped to receive at least a portion of the backing member 408, the electrically insulating isolation tube, and/or the ultrasound transducer 214. Accordingly, during delivery of the catheter 102 to the anatomical region being treated, the backing member 408, the isolation tube, and/or the ultrasound transducer 214 may be retracted within the bore 418 of the catheter 102, e.g., by retracting the electrical cabling, thereby providing sufficient stiffness to the catheter 102 such that the catheter 102 may be delivered in a safe manner.

Figure 5:
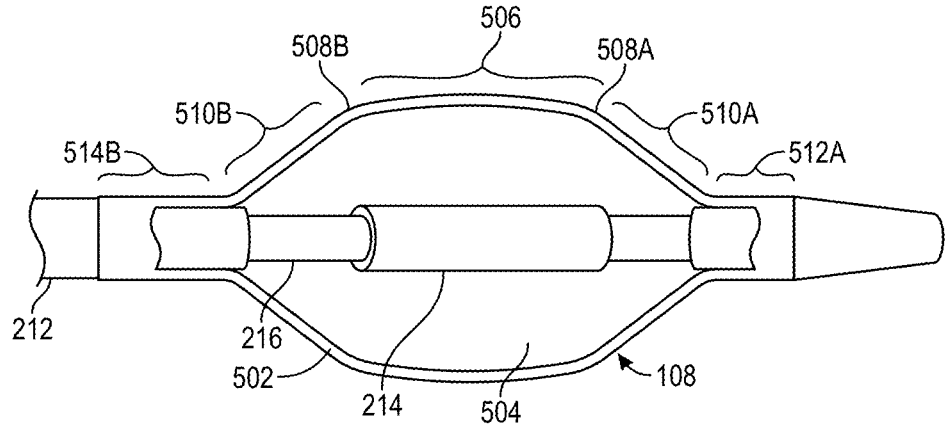
FIG. 5 is a side view of a tissue treatment system having a compliant balloon inflated to a first inflation diameter, in accordance with an embodiment.

Referring to FIG. 5, a side view of a tissue treatment system having a compliant balloon inflated to a first inflation diameter is shown in accordance with an embodiment. In certain embodiments, the balloon 108 is compliant and configured to be deployed in a wide range of lumen, blood vessel, or artery sizes. For example, the balloon 108 may be capable of adapting to arteries with an inner diameter of 3 mm to 8 mm. Accordingly, using the compliant balloon 108 permits only one catheter 102 to be used during a procedure, advantageously decreasing operating time, e.g., from about 1 hour to about 15 minutes for, e.g., a renal denervation procedure. In certain embodiments, the use of a compliant balloon advantageously decreases the complexity, and thereby the rate of complications, of the procedure.

In certain embodiments, the tissue treatment system 100 is configured to measure the lumen, blood vessel, or artery sizes, and since the balloon 108 is configured to accommodate a wide range of lumen sizes, e.g., 3 to 9 mm renal or accessory arteries, the controller 104 can be programmed to automatically inflate the balloon 108 to the appropriate diameter. Such automation advantageously provides improvements to the complexity of the procedure and mitigates a risk of user error. In certain embodiments, the tissue treatment system 100 having a compliant balloon 108 does not require the user to choose a balloon size and/or switch out catheters to provide multiple sized balloons during a single procedure.

The compliant medical balloon 108 can include a balloon wall 502, which at any longitudinal location, may have a generally annular cross-section. More particularly, the balloon wall 502 can have an outer surface that expands into contact with the target tissue, and an inner surface that defines an interior 504 of the balloon 108. As described above, the transducer 214 can be mounted on the catheter shaft 212, either directly or indirectly (e.g., via the electrical cabling).

The transducer 214 can be positioned within the interior 504 of the balloon 108. More particularly, the balloon 108 can have a balloon body 506, and the balloon body 506 can radially surround the transducer 214. For example, the balloon body 506 can be a generally cylindrical portion of the balloon wall 502 that extends radially around the transducer 214 relative to a longitudinal axis of the catheter shaft 212. The balloon body 506 can extend longitudinally between a plurality of corners 508. For example, a distal corner 508A can define a distal extent of the balloon body 506, and a proximal corner 508B can define a proximal extent of the balloon body 506. In an embodiment, a distance between the corners 508, which defines a length of the balloon body 506, can be equal to or greater than a length of the transducer 214. More particularly, the balloon body length may be, at a minimum, the length of the transducer 214. Accordingly, the transducer 214 can be positioned such that a proximal end of the transducer 214 is distal to the proximal corner 508B of the balloon 108, and a distal end of the transducer 214 is proximal to the distal corner 508A of the balloon 108. The corners 508 can transition the balloon body 506 into a plurality of shoulders 510. Furthermore, in addition to transitioning the balloon 108 sections, the shape of the corners 508 can have a primary impact on the ability of the balloon 108 to center the transducer 214 within the target vessel 302.

In an embodiment, the plurality of shoulders 510 include a distal shoulder 510A (distal to the balloon body 506) that connects the balloon body 506 to a distal mounting section 512A of the balloon wall 502. Similarly, a proximal shoulder 510B (proximal to the balloon body 506) can connect the balloon body 506 to a proximal mounting section 514B of the balloon wall 502. Accordingly, the shoulders 510 transition the portions of the balloon wall 502 that connect balloon 108 to the catheter shaft 212 with the portion of the balloon wall 502 that interacts with the target tissue during expansion.

The transducer 214 can be mounted on the isolation tube and/or the backing member. In this case the proximal mounting section 514B can be mounted on the catheter shaft 212 proximal to the transducer, but the distal mounting section 514A can be mounted on the transducer, backing member 408 or support tip 308. The mounting sections may be connected to the catheter shaft 212 via thermal, adhesive, or mechanical joints that hermetically seal the balloon 108 to the catheter shaft 212. Accordingly, the interior 504 of the balloon 108, which is between the mounting points, can surround the transducer 214 and provide a space for the inflation/cooling fluid to circulate around the transducer 214 during treatment.

It will be appreciated that, as opposed to compliant balloons 108 that primarily function to occlude a target anatomy, the balloon 108 of the tissue treatment system 100 functions to center the transducer 214 within the target vessel 302. The flexibility of the balloon 108 required to achieve the inflation methodologies described below, however, may lead to the transducer 214 becoming eccentric with the vessel lumen if particular features are not implemented in the balloon 108. More particularly, a shape and material of the balloon 108 can be provided as described below to provide a compliant balloon 108 that is also supportive enough to center the transducer 214 within the target vessel 302 during use.

The shape of the balloon 108 can contribute to optimally centering the transducer 214 within the target vessel 302. In an embodiment, the balloon body 506 and the plurality of shoulders 510 meet at round corners 508. The corners 508 may be considered round because, rather than the transition between the shoulder 510 and the balloon body 506 being sharp or angular, the transition has a smooth, arcuate profile. The profile can be described as having a full radius, as opposed to a discrete change in radius that would be apparent, for example, in medical balloons typically used for angioplasty procedures. It has been shown that, as compared to balloon shapes having sharp corners, the round corners 508 of the balloon 108 provide that, when the balloon 108 is inflated within the target vessel 302, the catheter shaft 212 (and the transducer 214 mounted on the catheter shaft 212) remains centered in the target vessel 302.

The material of the balloon 108 can contribute to optimally centering the transducer 214 within the target vessel 302. In certain embodiments, e.g., suitable for renal denervation, the balloon 108 may comprise nylon, polyether block amide (PEBAX®), or other suitable polymers. In an embodiment, the balloon wall 502 is formed from an elastomeric material. For example, the elastomeric material can include a urethane material, such as a thermoplastic polyurethane (TPU). The TPU can be a polyether-based TPU, such as Pellethane®. Alternatively, the balloon wall 502 may be formed from another medical grade polyether-based TPU, such as Isothane®.

Isothane® is a urethane material having a material specification that is closely controlled. As compared to other types of urethane, Isothane® may be particularly useful in that variation in material properties between lots of material are low. More particularly, from lot to lot, Isothane® may have fewer gels and more consistent block chains as compared to other materials. Accordingly, in an embodiment, the raw material used to form the balloon 108 is Isothane®.

A hardness of the balloon material can contribute to the compliance of the balloon 108, e.g., an ability of the balloon to expand and conform to different vessel lumen diameters. The hardness can also contribute to the ability of the balloon 108 to supportively center the transducer 214. Accordingly, the material used to form the balloon wall 502 may have a Shore durometer between about 95 A and about 55 D. More particularly, the balloon wall material can have a Shore D durometer in a range of 50 to 60. For example, the balloon 108 may be formed from Pellethane® having a Shore D durometer of 55, or Isothane® having a shore durometer of 5095 A, 7195 A, or 5055 D. In a particular embodiment, it has been shown that the balloon wall 502 formed from Isothane® having a Shore D durometer of 55 can provide excellent results in balancing the performance goals of compliant expansion with supportive strength.

Whereas non-compliant balloon inflation is limited by the balloon itself, i.e., the balloon diameter is generally fixed when inflated at different pressures within the expected operating range, and therefore can accommodate a limited range of vessel sizes, compliant balloon expansion can employ multiple methods of inflation that allow the compliant balloon to accommodate a larger range of vessel sizes. The compliant medical balloon 108 of the tissue treatment system 100 described above can be deployed in the target vessel 302 using any of several inflation methodologies. Such methodologies can be termed a "pressure limiting approach," an "arterial limiting approach," and a "hybrid approach."

The pressure limiting approach involves using specific inflation pressures to attain specific balloon diameters to gain apposition to various vessel sizes. The arterial limiting approach involves using a fixed inflation pressure that is used regardless of arterial diameter. The hybrid approach is a combination of the arterial limiting and pressure limiting approaches. The hybrid approach involves using a fixed inflation pressure to gain apposition to smaller arterial diameters, but using alternate (higher) inflation pressures to gain apposition to larger arterial diameters. The strength of the artery effectively determines the size of the balloon 108 at low pressures, and at higher pressures the balloon pressure determines the size of the balloon 108. These inflation paradigms are described in further detail below.

Still referring to FIG. 5, the balloon is shown in a first state and, more particularly, at a first inflation diameter. The inflation diameter can be an outer dimension of the balloon body 506. In an embodiment, the balloon wall 502 has a shape and stiffness (as described herein) such that, when the compliant balloon 108 is inflated to a first inflation pressure of 10 psi, the balloon body 506 of the balloon wall 502 has a cylindrical profile and a first inflation diameter of 3.5 mm to 6 mm. The inflation pressure can correspond to a flow rate of fluid circulated through the interior 504 of the balloon 108 between the inlet channel 403 and the outlet channel 405. For example, the fluid may be circulated at a flow rate of 15 to 35 mL/min (e.g., 25 to 35 mL/min) to inflate the balloon 108 to the inflation pressure of 10 psi, which results in the first inflation diameter of 3 to 6 mm (e.g., 3.5 to 6 mm). The balloon body 506 of the balloon 108 can have the first inflation diameter of 3.5 mm at a first inflation pressure of 10 psi and a flow rate of 30 mL/min.

In certain embodiments used for the pressure limiting approach, a single balloon 108 can have an inflation diameter that is directly related to the pressure in the balloon 108. More particularly, the outer diameter of the balloon 108 is directly related to the pressure in the balloon 108. According to this embodiment, the higher the pressure, the bigger the balloon 108. It is contemplated that the balloon 108 may have an expansion range of 3.5 to 9 mm. More particularly, the balloon 108 may have a nominal size of 3.5 mm when inflated to the state shown in FIG. 5, however, as the inflation pressure is increased, the inflation diameter may also increase.

Figure 6:
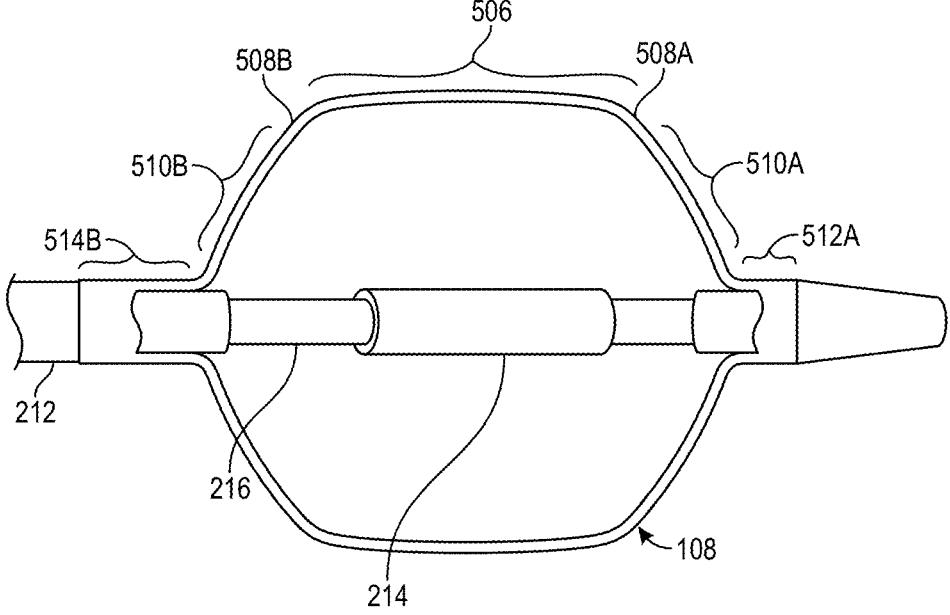
FIG. 6 is a side view of a tissue treatment system having a compliant balloon inflated to a second inflation diameter, in accordance with an embodiment.

Referring to FIG. 6, a side view of a tissue treatment system having a compliant balloon inflated to a second inflation diameter is shown in accordance with an embodiment. When the medical balloon 108 is inflated to a second inflation diameter, e.g., 8 mm, the balloon wall 502 can have essentially the same sections described above. More particularly, the medical balloon 108 can include the mounting sections 512, shoulders 510, and balloon body 506. The corners 508, which transition the balloon body 506 into the shoulders 510, can be rounded. In an embodiment, the arcuate corners 508 can have a same radius as the balloon body 506 and the shoulders 510 such that the balloon wall 502 has a single, arcuate profile of a same radius between the distal mounting section 512 and the proximal mounting section 514. As in FIG. 5, the balloon body 506 can be longer than, and surround, the transducer 214 mounted on the catheter shaft 212.

Although the shoulders 510 may be rounded, the balloon 108 may have angular shoulders instead. More particularly, angular shoulders, as describe with respect to FIGS. 21-23, may be incorporated in the balloon design. Angular corners have been shown to center and support the transducer when combined with the other features described with respect to FIGS. 21-23.

In an embodiment, the balloon wall 502 has a shape and stiffness (as described herein) such that, when the compliant balloon 108 is inflated to a second inflation pressure of 30 psi, the balloon body 506 of the balloon wall 502 has a cylindrical profile and a second inflation diameter of 8 mm to 9 mm. The inflation pressure can correspond to a flow rate of fluid circulated through the interior 504 of the balloon 108 between the inlet channel 403 and the outlet channel 405. For example, the fluid may be circulated at a flow rate of 35 to 50 mL/min (e.g., 40 to 45 mL/min) to inflate the balloon 108 to the inflation pressure of 30 psi, which results in the first inflation diameter of 8 to 9 mm. For example, the balloon body 506 of the balloon 108 can have the second inflation diameter of 8 mm at a second inflation pressure of 30 psi and a flow rate of 40 to 45 mL/min.

Figure 7:
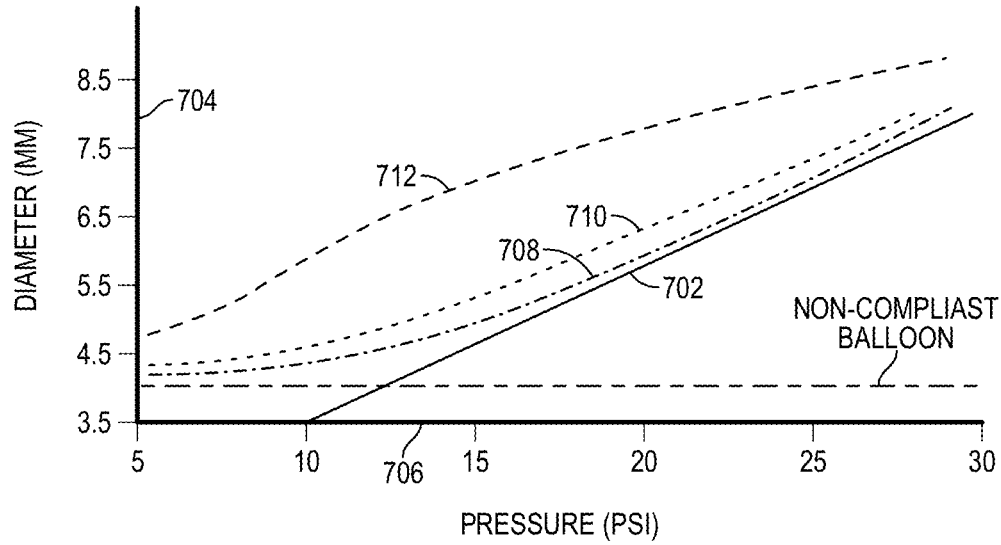
FIG. 7 is a diagram of balloon pressure curves of balloons being inflated according to a pressure limiting approach, in accordance with an embodiment.

Referring to FIG. 7, a diagram of balloon pressure curves of balloons being inflated according to a pressure limiting approach is shown in accordance with an embodiment. In the pressure limiting approach, the balloon 108 can have a pressure curve that approximates an ideal inflation curve 702. The ideal inflation curve 702 can extend linearly from the first inflation diameter of 3.5 mm at the first inflation pressure of 10 psi to a second inflation diameter of 8 mm at a second inflation pressure of 30 psi. The balloon 108 can therefore accommodate a 3.5 to 8 mm vessel lumen diameter of a same vessel or several vessels. More particularly, an inflation diameter 704 of the balloon 108 corresponds to an inflation pressure 706 of the balloon 108.

The balloon 108 can be inflated by circulating the inflation fluid 306 within the balloon 108. More particularly, circulating the inflation fluid 306 within the balloon 108 generates the inflation pressure that expands the balloon 108 to the inflation diameter. The inflation pressure can be proportional to the flow rate. Accordingly, the inflation fluid 306 can be circulated within the balloon 108 based on a lumen diameter 320 of the target vessel 302 to inflate the balloon 108 to the desired size. For example, the flow rate associated with the second inflation pressure (and the second inflation diameter) may be greater than the flow rate associated with the first inflation pressure (and the first inflation diameter). By way of example, the inflation fluid 306 may be circulated through the balloon 108 at a flow rate between 25 and 45 mL/min to achieve the inflation diameters 704 along the ideal inflation curve 702. In an embodiment, when the inflation fluid 306 is sterile water, the flow rate may be 30 mL/min to achieve the inflation pressure of 10 psi associated with the inflation diameter of 3.5 mm. When the inflation fluid 306 is sterile water, the flow rate may be 40-45 mL/min to achieve the inflation pressure of 30 psi associated with the inflation diameter of 8 mm. In another embodiment, when the inflation fluid 306 is D5W, the flow rate may be 27 mL/min to achieve the inflation pressure of 10 psi associated with the inflation diameter of 3.5 mm. When the inflation fluid 306 is D5W, the flow rate may be 40 mL/min to achieve the inflation pressure of 30 psi associated with the inflation diameter of 8 mm. Accordingly, the pressure limiting approach can utilize flow rates of at least 30 mL/min to achieve inflation pressures of 10-30 psi. It has been shown that a flow rate of 30 mL/min or more circulates fluid sufficiently to adequately cool tissue during renal denervation.

In an embodiment, the balloon 108 approximates the ideal inflation curve 702 over several inflation cycles. For example, the balloon 108 can be inflated to the first inflation diameter (or the second inflation diameter) a first time 708 when the tissue treatment system 100 is introduced into a renal artery. The balloon 108 may be inflated one or more additional times, e.g., a fifth time 710, to treat different regions along a length of the renal artery. It has been shown that, using the materials described above, the inflation curves for the balloon 108 at each inflation cycle approximate each other and the ideal pressure curve. For example, when the balloon 108 is formed from Isothane® 55D, the inflation diameter when the balloon 108 is inflated the first time 708 is within 10% of the inflation diameter when the balloon 108 is inflated the fifth time. By contrast, balloons formed from other materials not contemplated above may exhibit less consistent inflation curves over several cycles. For example, balloons formed from other materials not contemplated above may exhibit inflation diameters 704 at an Nth time 712 that are more than 10% different than inflation diameters 704 at a first time 708. Accordingly, the balloon 108 described herein provides good inflation consistency that permits a single device to be inflated several times to treat a same or different vessels during a single procedure.

Figure 8:
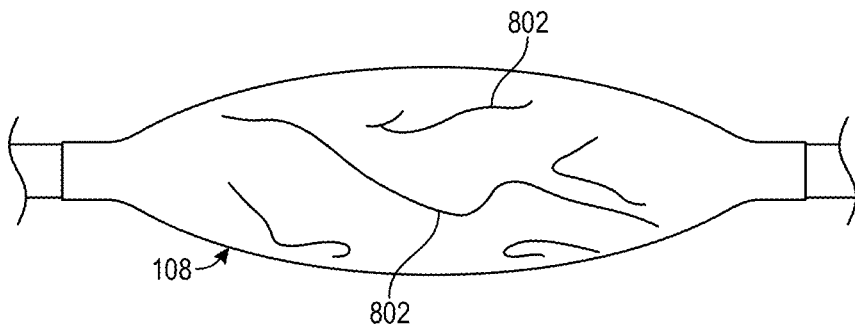
FIG. 8 is a perspective view of a compliant balloon inflated to a predetermined inflation pressure according to an arterial limiting approach, in accordance with an embodiment.

Referring to FIG. 8, a side view of a tissue treatment system having a compliant balloon inflated to a predetermined inflation pressure according to an arterial limiting approach is shown in accordance with an embodiment. In the arterial approach, a single large balloon 108, e.g., having an 8 mm inflation diameter, may be inflated to a low pressure, e.g., 10 psi or less, within the target vessel 302. The target vessel 302 can have a vessel lumen diameter 320 that is less than the nominal inflation diameter. For example, the balloon 108 of FIG. 5, rather than having a nominal diameter of 3.5 mm, may have a nominal diameter of 8 mm. Therefore, when the balloon 108 is placed in the target vessel 302 having a smaller vessel lumen diameter, e.g., an artery with an inner diameter of 4 mm, the balloon body 506 will contact the vessel wall 303 before the balloon 108 reaches the nominal diameter. A hoop strength of the artery, in combination with the low inflation pressure, can therefore keep the balloon 108 at a smaller-than-nominal diameter and can maintain the balloon body 506 in a generally cylindrical profile. More particularly, the hoop strength of the renal artery and the inflation pressure can prevent the compliant balloon 108 from expanding to the nominal inflation diameter of the compliant balloon.

In smaller vessels, the balloon 108 may need to be made of excess or thicker material compared to balloons 108 normally intended to accommodate only small body lumens because the balloon 108 must accommodate a wide range of body lumen dimensions. Accordingly, wrinkles 802 that would otherwise be ironed out due to expansion in larger body lumens can result. More particularly, when the balloon 108 is inflated in the target vessel 302 using the arterial limiting approach, the target vessel 302 can constrain the balloon 108, and thus, the balloon 108 can include several wrinkles 802 at the vessel wall 303 where the excess material folds to accommodate the smaller-than-normal diameter. The compliant balloon 108 can be a Pellethane® balloon having a Shore D durometer of 55 and have a double wall thickness of 0.0004 to 0.0014 inch, e.g., 0.0009 inch, and may include several wrinkles 802 that do not significantly interfere with energy delivery of the catheter. For example, the wrinkles 802 can have a predictable wrinkle pattern that does not interfere with substantially with energy delivery. The predictable wrinkle pattern can have a low density of wrinkles, or may have wrinkles that occur in particular locations that are not in the primary energy delivery path. Accordingly, the wrinkles can accommodate the smaller-than-normal diameter without inhibiting treatment of the target tissue.

In the arterial limiting approach, the balloon 108 is inflated to a predetermined inflation pressure, regardless of a vessel lumen diameter. More particularly, the low pressure used for the arterial limiting approach can be a fixed pressure that is used regardless of the vessel lumen diameter. For example, the predetermined inflation pressure can be 10 psi or less, and may be used in any target vessel 302 having a vessel lumen diameter less than the nominal diameter of the balloon 108. It will be appreciated that this inflation paradigm is distinct from the pressure limiting approach, which utilizes inflation pressures based on the lumen diameter that is being targeted.

Figure 9:
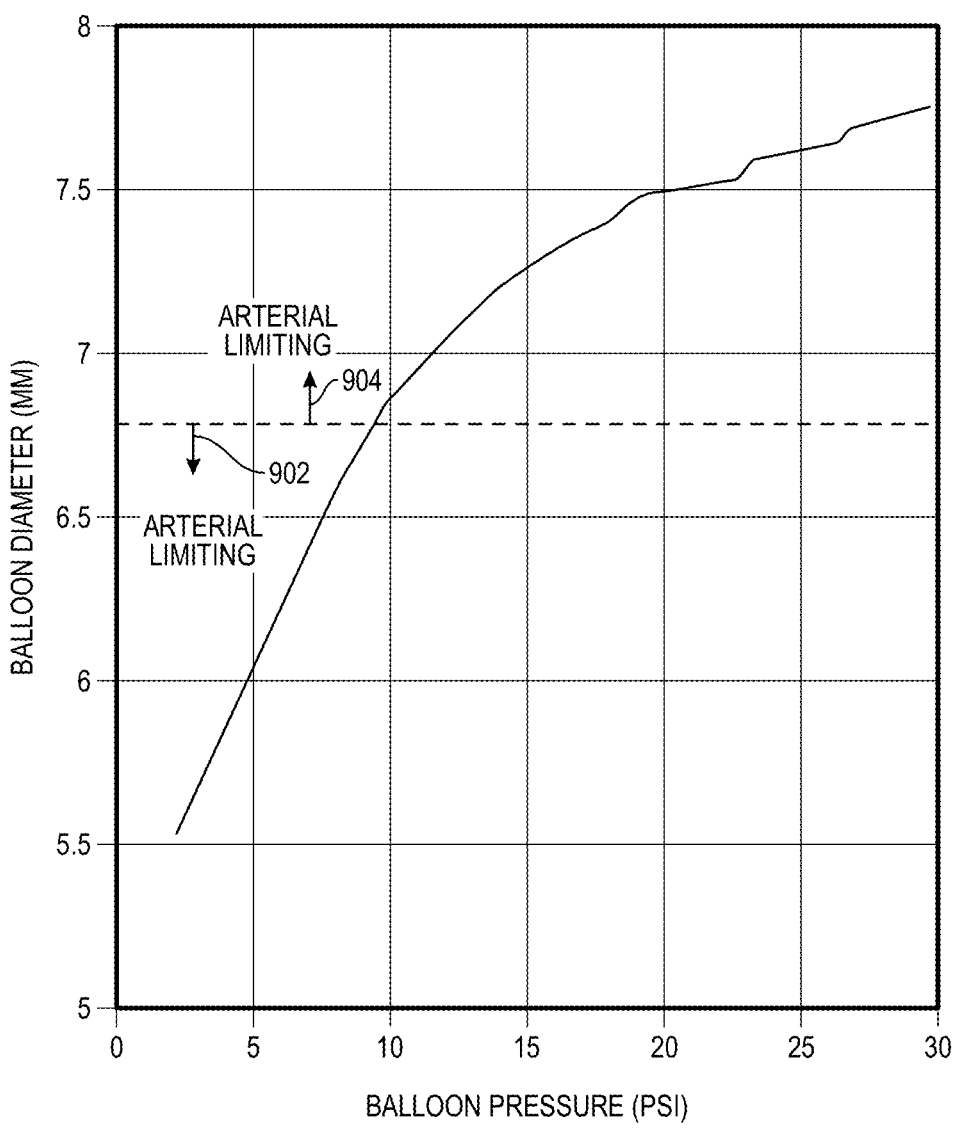
FIG. 9 is a diagram of a balloon pressure curve of a compliant balloon being inflated according to a hybrid inflation approach, in accordance with an embodiment.

Referring to FIG. 9, a diagram of a balloon pressure curve of a compliant balloon 108 being inflated according to a hybrid inflation approach is shown in accordance with an embodiment. In the hybrid inflation approach, a single, compliant balloon 108 having a nominal inflation diameter can be used to treat vessel lumen diameters smaller than the nominal inflation diameter and larger than the nominal inflation diameter. The compliant balloon 108 can similarly treat the lumen diameters in different vessels, or in different portions of a same vessel, e.g., a distal portion and a proximal portion of the vessel. The balloon 108 may be sized to be at or near a mid-point of a size appropriate for a set of body lumen diameters. For example, with respect to typical renal artery lumen sizes, a balloon 108 having a nominal diameter of 6.75 mm may be provided.

The hybrid approach is a combination of the arterial limiting approach and the pressure limiting approach. In the above example of the balloon 108 having the nominal diameter of 6.75 mm, for an artery less than 6.75 mm, the balloon 108 may be inflated to a low pressure, e.g., 10 psi. Over that inflation range, the balloon 108 may be in an arterial limiting range of operation 902. In the arterial limiting range of operation, the balloon 108 is arterial limited as described above with respect to FIG. 8. Accordingly, when the compliant balloon 108 is inflated to a first inflation pressure within a renal artery (or renal artery portion) having a first arterial diameter that is smaller than the nominal inflation diameter of the compliant balloon 108, the hoop strength of the renal artery and the inflation pressure prevents the compliant balloon 108 from expanding to the nominal inflation diameter of the compliant balloon 108.

By contrast, for an artery (or artery portion) larger than 6.75 mm, the pressure in the balloon 108 can be increased to increase the size of the balloon 108. The balloon 108, when operating above the 6.75 mm inflation diameter, can be operating in a pressure limiting range of operation 904. In the pressure limiting range of operation 904, the balloon 108 is pressure limited as described above with respect to FIG. 7. Accordingly, when the compliant balloon 108 is inflated to a second inflation pressure higher than the first inflation pressure within a renal artery (or renal artery portion) having a second arterial diameter larger than the nominal inflation diameter of the compliant balloon 108, the second inflation pressure expands the diameter of the compliant balloon 108 to be larger than the nominal inflation diameter of the compliant balloon 108. The inflation pressure can be gradually increased to expand the balloon 108 into apposition with gradually larger arterial diameters. The 6.75 mm nominal diameter is provided by way of example, and as in the embodiments above, the balloon 108 may have a nominal diameter of 3.5 mm, 3.7 mm, 4.5 mm, 5.5 mm, 6.5 mm, or any other diameter that delineates the arterial limiting range of the balloon 108 from the pressure limiting range of the balloon 108.

In an embodiment, the compliant balloon 108 has a nominal inflation diameter of about 4 mm. When the compliant balloon 108 is inflated to a first inflation pressure within a first arterial diameter of a renal artery having a diameter less than 4 mm, the hoop strength of the renal artery and the inflation pressure prevents the compliant balloon 108 from expanding to a diameter larger than the first arterial diameter of the renal artery. When the compliant balloon 108 is inflated to a second inflation pressure higher than the first inflation pressure within a renal artery having a second diameter larger than 4 mm, however, the second inflation pressure expands the diameter of the compliant balloon 108 to be in apposition with the second diameter of the renal artery.

As a further example of the hybrid approach, the compliant balloon 108 can be a Pellethane® balloon having a Shore D durometer of 55 and a nominal inflation diameter of 5.5 mm. The compliant balloon 108 can be inflated at a constant low balloon pressure for apposition in smaller arterial diameters, but for incrementally larger arterial diameters, the pressure is increased to match the balloon size to the artery diameter. Table 1 lists the balloon pressures used to reach the balloon diameter size range. Note that the inflation pressure for diameters up to, and slightly above, the nominal inflation diameter of the compliant balloon are a single, low pressure of 10 psi. The inflation pressures then gradually increase to achieve inflation diameters 704 above 6 mm.

TABLE 1

| Balloon Inflation Data | | |
| --- | --- | --- |
| Balloon Type | Diameter (mm) | Pressure (psi) |
| 5.5 mm Pellethane (55D) | ≤6.0 | 10 |
| | 6.1-6.5 | 12 |
| | 6.6-7.0 | 16 |
| | ≥7.0 | 20 |

As described above, the inflation pressure is dependent on the flow rate of the inflation fluid 306 within the balloon 108.

Table 2 provides approximate flow rate values of three selected pressures from the complete range of 10 to 20 psi that may be used to inflate the balloon 108 using a hybrid approach. Note that the flow rates are around or above 30 mL/min, which has been shown to effectively cool tissue during renal denervation.

TABLE 2

| Balloon Flow Rate Data | |
| --- | --- |
| Pressure (psi) | Flow Rate (mL/min) |
| 10 | ~24 |
| 15 | ~24 |
| 20 | ~29 |
| 30 | ~40 |

Figure 10:
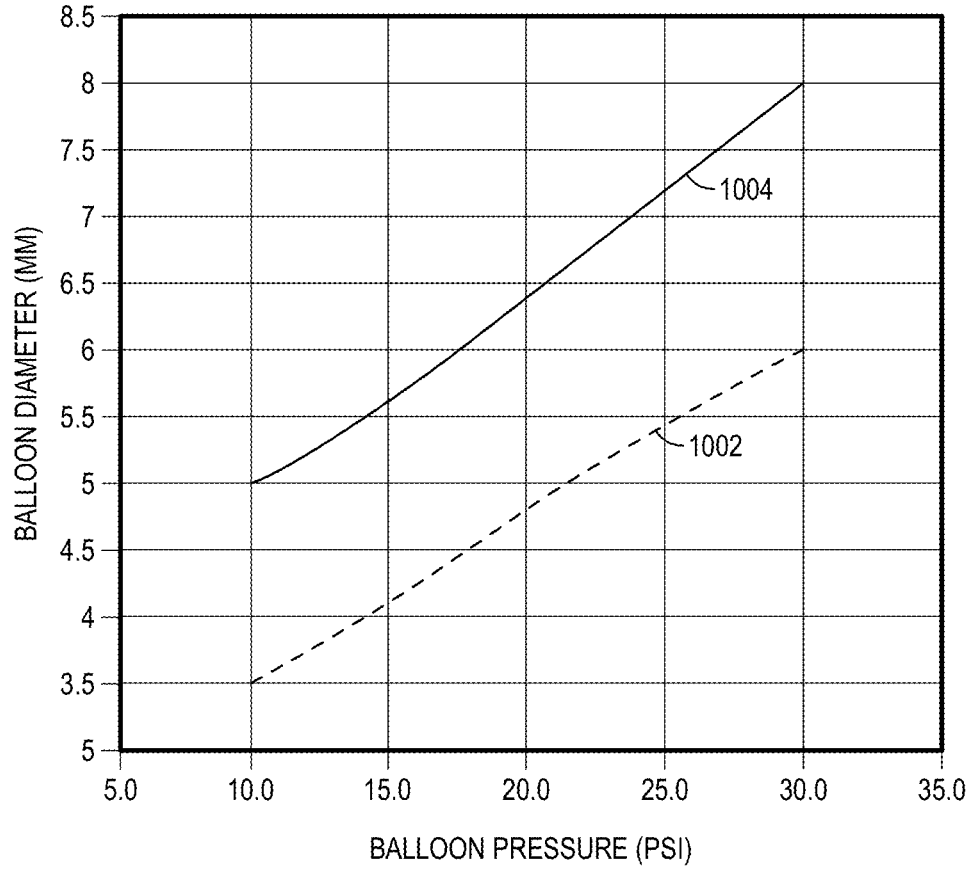
FIG. 10 is a diagram of balloon pressure curves of two compliant balloons being inflated according to a pressure limiting approach, in accordance with an embodiment.

Referring to FIG. 10, a diagram of balloon pressure curves of two compliant balloons being inflated according to a pressure limiting approach is shown in accordance with an embodiment. The diagram provides the foundation for an option to provide a product portfolio having a limited number of device models. For example, two catheters, each having respective compliant balloons, may be used to cover a range of vessel lumen diameters, e.g., 3 to 9 mm arteries. A first compliant balloon curve for a first catheter can cover a first vessel size range, e.g., 3 to 5 mm. A second compliant balloon curve for a second catheter can cover a second vessel size range, e.g., 4 to 9 mm. The two balloon curves can overlap by a predetermined amount to ensure full coverage of the 3-9 mm full range of inflation. For example, the overlap between the first inflation diameter range of the first compliant balloon curve and the second inflation diameter range of the second compliant balloon curve can be in a range of 0.5 to 5 mm, e.g., 1 mm. Each balloon 108 can achieve the respective coverage using inflation pressures between 10 to 30 psi, which correspond to the effective cooling fluid flow rates described above. Accordingly, the combined device portfolio can cover a vessel size range of 3 to 9 mm, which is sufficient for a majority of renal artery sizes. A portfolio of tissue treatment systems 100 having only two device models with compliant balloons 108 would provide a substantial improvement over a portfolio of five or more device models with non-compliant balloons 108. The two device models could be provided in a kit. More particularly, the kit could include two catheters having the balloon constructions described herein. The catheters in the kit could have respective compliance curves, such as those shown in FIG. 10, to cover a vessel size range of 3 to 9 mm, which is typically sufficient for the general population of renal artery sizes.

Figure 11:
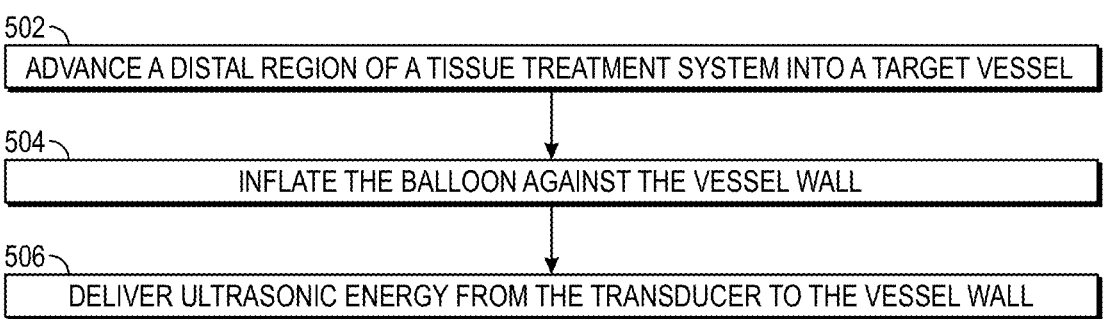
FIG. 11 is a flowchart of a method of delivering ultrasonic energy to a vessel wall using a tissue treatment system, in accordance with an embodiment.

Referring to FIG. 11, a flowchart of a method of delivering ultrasonic energy to a vessel wall using a tissue treatment system is shown in accordance with an embodiment. Having described the tissue treatment system 100 and the various inflation paradigms above, the method of treating tissue of the target vessel 302 can now be described.

A diameter of the target vessel, e.g., an arterial diameter of a renal artery, can be measured. By way of example, contrast media may be injected into the renal artery and viewed under fluoroscopy to evaluate the vessel size. The vessel diameter can be noted, and an appropriate inflation pressure may be used to inflate the balloon to the measured vessel diameter. The process of measuring the diameter of the target vessel can be performed prior to, or after, insertion of the treatment catheter. For example, in the case of a one-size-fits-all catheter, the vessel measurements may be made after the treatment catheter is inserted. Alternatively, when using a kit having two treatment catheters with differently sized balloons, the vessel measurements may be made prior to selecting and inserting one of the treatment catheters into the vessel.

At operation 502, the tissue treatment system 100 can be inserted into the patient and disposed within the target anatomy. For example, after positioning the guidewire 310 in the target vessel 302, the support tip 308 can be loaded onto the guidewire 310 and the distal region 202 can be tracked over the guidewire 310 into the target vessel 302.

At operation 504, the balloon 108 can be inflated against the vessel wall 303. The balloon 108 may be inflated according to any of the inflation paradigms described above. For example, the balloon 108 can be inflated using the pressure limiting approach by circulating fluid within the balloon 108, based on the lumen diameter of the target vessel 302, to inflate the balloon 108 into apposition with the vessel wall 303. By contrast, the balloon 108 can be inflated using the arterial limiting approach by inflating the balloon 108 to the predetermined inflation pressure, regardless of the lumen diameter of the target vessel 302, until the balloon 108 is apposed to and constrained by the target vessel 302. In the hybrid approach, the balloon 108 can be inflated by first circulating fluid within the balloon 108 at a first flow rate to inflate the balloon 108 to the predetermined inflation pressure within a first portion of a renal artery having a first arterial diameter that is smaller than a nominal inflation diameter of the compliant balloon 108. In such case, the hoop strength of the renal artery and the first predetermined inflation pressure prevents the compliant balloon 108 from expanding to a diameter larger than the first arterial diameter of the renal artery.

At operation 506, ultrasonic energy is delivered from the transducer 214 to the vessel wall 303. More particularly, the ultrasonic energy can be delivered to the first portion of the renal artery.

The compliant balloon 108 may be moved to a different artery or to a different portion of a same artery. The hybrid approach can include circulating inflation fluid 306 within the balloon 108 at a second flow rate, higher than the first flow rate, to inflate the balloon 108 to a second predetermined inflation pressure within a renal artery (or portion) having a second diameter that is larger than a nominal inflation diameter of the compliant balloon 108. The second inflation diameter may be larger than the first inflation diameter. More particularly, the second inflation pressure can expand the diameter of the compliant balloon 108 to be larger than the nominal inflation diameter of the compliant balloon 108. Depending on a size of the target vessel 302 location, the balloon 108 can appose the vessel wall 303 at the first inflation diameter or the second inflation diameter. When the balloon 108 is inflated within the target vessel 302 and apposed to the vessel wall 303, the catheter shaft 212 remains centered in the target vessel 302 and the transducer 214 is supported centrally within the vessel lumen due to the balloon shape and material described above. Ultrasonic energy can be delivered from the transducer 214 to the second portion of the renal artery.

It is contemplated that for 3.5 to 8 mm compliant balloons, a patient entry power will range from 27 to 38 W. In certain embodiments, a power setting may be used to achieve such patient entry power. More particularly, a particular energy density (energy per balloon volume) may be achieved by controlling generator power settings. In an embodiment, a 5.5 mm Pellethane® balloon 108 having a Shore D durometer of 55 can be used with an energy density in a range of 100 to 250 J/mL to achieve the patient entry power required to treat the target vessel. Using such energy density, acoustic power outputs can be reached that ablate renal nerves 304 having vessel diameters of 3 to 9 mm. The programmed power settings of the controller 104 may increase with lumen/balloon diameters to achieve consistent ablation depths. In an embodiment, a programmable logic block is configured to select an acoustic output power that is adjusted based on lumen diameter.

In certain embodiments, the tissue treatment system 100 and/or compliant balloon 108 can incorporate features to contribute to centering the transducer 214 within the vessel lumen. As described below, the compliant balloon 108 can incorporate features in addition to, or instead of, the rounded corners 508 and/or cylindrical balloon body 506 that center the transducer 214 across a range of vessel sizes. Furthermore, various centering mechanisms may be incorporated in the tissue treatment system 100 to supplement the inherent centering capability of the balloon 108. Several such features are described below.

Figure 12:
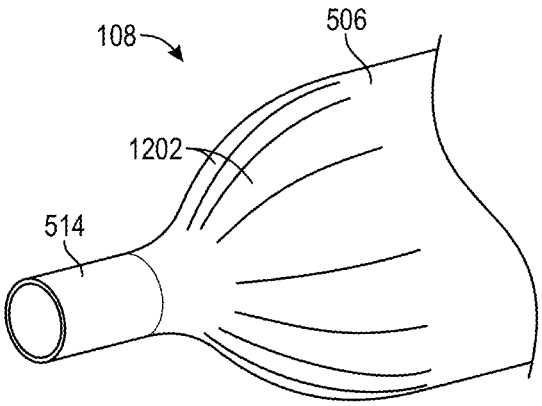
FIG. 12 is a perspective view of a compliant balloon having longitudinal ribs, in accordance with an embodiment.

Referring to FIG. 12, a perspective view of a compliant balloon having longitudinal ribs is shown in accordance with an embodiment. In an embodiment, the shoulders 510 of the compliant balloon 108 can include one or more longitudinal ribs 1202. For example, several longitudinal ribs 1202 can extend in the longitudinal direction from the balloon body 506 to the mounting section (either the distal or proximal mounting section 514) of the balloon 108. The longitudinal ribs 1202, arranged circumferentially about the longitudinal axis of the balloon 108, can provide a stiffened, pleated section. More particularly, the ribs can act as stiffening elements that resist deformation in the transverse direction. Accordingly, the pleats may stabilize the balloon 108 when the balloon is inflated within the target vessel 302, causing the balloon to inflate and deflate in a predictable manner without resulting in decentering the transducer 214.

In certain embodiments, the pleated section can also contribute to predictable folding of the balloon 108, e.g., during deflation. For example, the pleated section may incorporate multilayer, elastomeric, heat-set, and/or magnetic regions. The enhanced regions may be configured to cause the balloon 108 to preferentially fold into a low-profile deflated state. The low-profile state can have a primarily circular cross-section, as opposed to a flattened cross section having a larger maximum cross-sectional dimension. The low-profile circular cross-section can allow the balloon 108 to be retrieved from the patient anatomy with a reduced risk of causing vascular trauma during removal. Advantageously, balloon fold memory may also help reduce pinhole rates when the balloon 108 is subject to puncture risks, such as exposed wire from braiding of a guide catheter during a procedure. Accordingly, the pleated section can supplement centering of the transducer 214, reduce a likelihood of patient injury, and reduce a likelihood of device failure.

Figure 13:
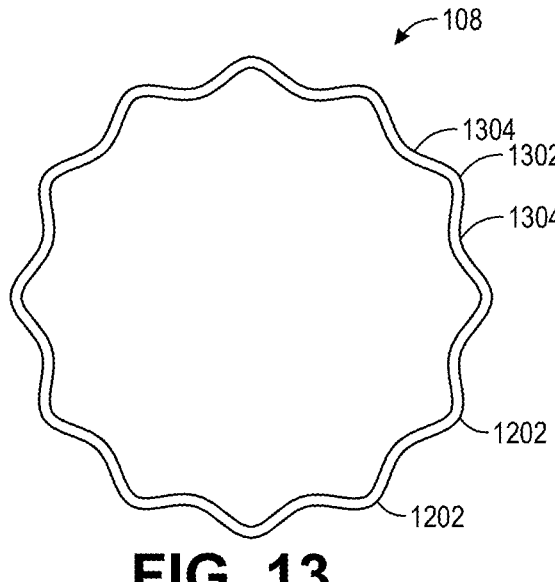
FIG. 13 is a cross-sectional view of the compliant balloon of FIG. 12, in accordance with an embodiment.

Referring to FIG. 13, a cross-sectional view of the compliant balloon of FIG. 12 is shown in accordance with an embodiment. In cross-section, it is seen that the longitudinal folds can be defined by a peak 1302 circumferentially between several valleys 1304. The balloon surface can be curved or angular at the peaks and valleys. For example, the cross-section can have the arcuate transitions shown in FIG. 13, or may have a circular, corrugated shape when the peaks and valleys are angular.

A balloon mold that may be used during the manufacturing of the balloon 108 can have an internal shape to create the longitudinal ribs 1202 when the balloon 108 is blown. The longitudinal ribs 1202 can be formed into the balloon 108, in addition to the rounded corners 508 described above. The rounded corners 508 and the longitudinal ribs 1202 may reduce tension applied from the shoulders 510 to the balloon body 506 of the balloon 108 and the geometrically "folded" profile permits the shoulders 510 to expand as the balloon 108 expands, advantageously permitting greater expansion of the balloon 108 without bursting, and permitting less balloon material to be used to accommodate a range of blood vessels. The greater expansibility provided by the longitudinal ribs 1202 can reduce wrinkling associated with other compliant (thicker-walled) balloon embodiments.

The balloon shoulders 510 may have, in addition to or instead of ribs, other features to contribute to transducer 214 centering. In an embodiment, the balloon wall 502 is thicker at the shoulders 510 than at the balloon body 506. The thickness of the shoulder 510 may be uniform, e.g., a same balloon wall thickness between the mounting section 514 and the corner 508, or variable, e.g., the balloon wall thickness may increase or decrease from the mounting section 514 to the corner 508. The thicker shoulders 510 can be stiffer than the balloon body 506, and thus, the shoulders 510 may be less susceptible to deformation than the balloon body 506 when the balloon 108 is inflated in the target vessel 302. Accordingly, the thickened taper section can resist transverse loads to maintain the catheter shaft 212 and the transducer 214 centered within the target vessel lumen. Additionally, a comparatively thinner balloon body 506 can contribute to uniform energy delivery to the tissue surrounding the balloon. More particularly, the comparatively thinner balloon body 506 can provide comparatively higher transmission of the ultrasonic energy emitted by the transducer and, thus, energy delivery to the surrounding tissue can be uniform and effective.

The balloon 108 may be shaped in other manners to achieve the transducer centering functionality. For example, the balloon 108 may have an inverse conical shape that resists transverse deformation. The inverse conical shape includes a generally cylindrical balloon body 506 between a proximal corner 508B and a distal corner 508A. The shoulders 510 can converge axially inward from the corners 508 such that the mounting sections 514 are at least partly radially within the balloon body 506. For example, the distal mounting section 512A can have a proximal end that is proximal to the distal corner 508A. Likewise, the proximal mounting section 514B can have a distal end that is distal to the proximal corner 508B. Like the other stiffening features described above, the inverse conical configuration can enable the balloon 108 to expand and deflate in a predictable way without causing the transducer 214 to decenter. The transducer 214 may therefore create a circumferentially uniform lesion along the vessel wall 303.

It is contemplated that any of the shoulder configurations described above can contribute to the balloon body 506 having a cylindrical shape when the balloon 108 is inflated within the target vessel 302. Maintaining the cylindrical balloon body shape can reduce the likelihood of introducing inefficiencies into the system. More particularly, a cylindrical balloon body 506 may allow for proper waveform propagation from the transducer 214 to the vessel wall 303, as compared to a non-cylindrical balloon body. Accordingly, the balloon shape can both center the transducer 214 and effectively transmit energy directed radially outward from the transducer 214.

Figures 14A, 14B:
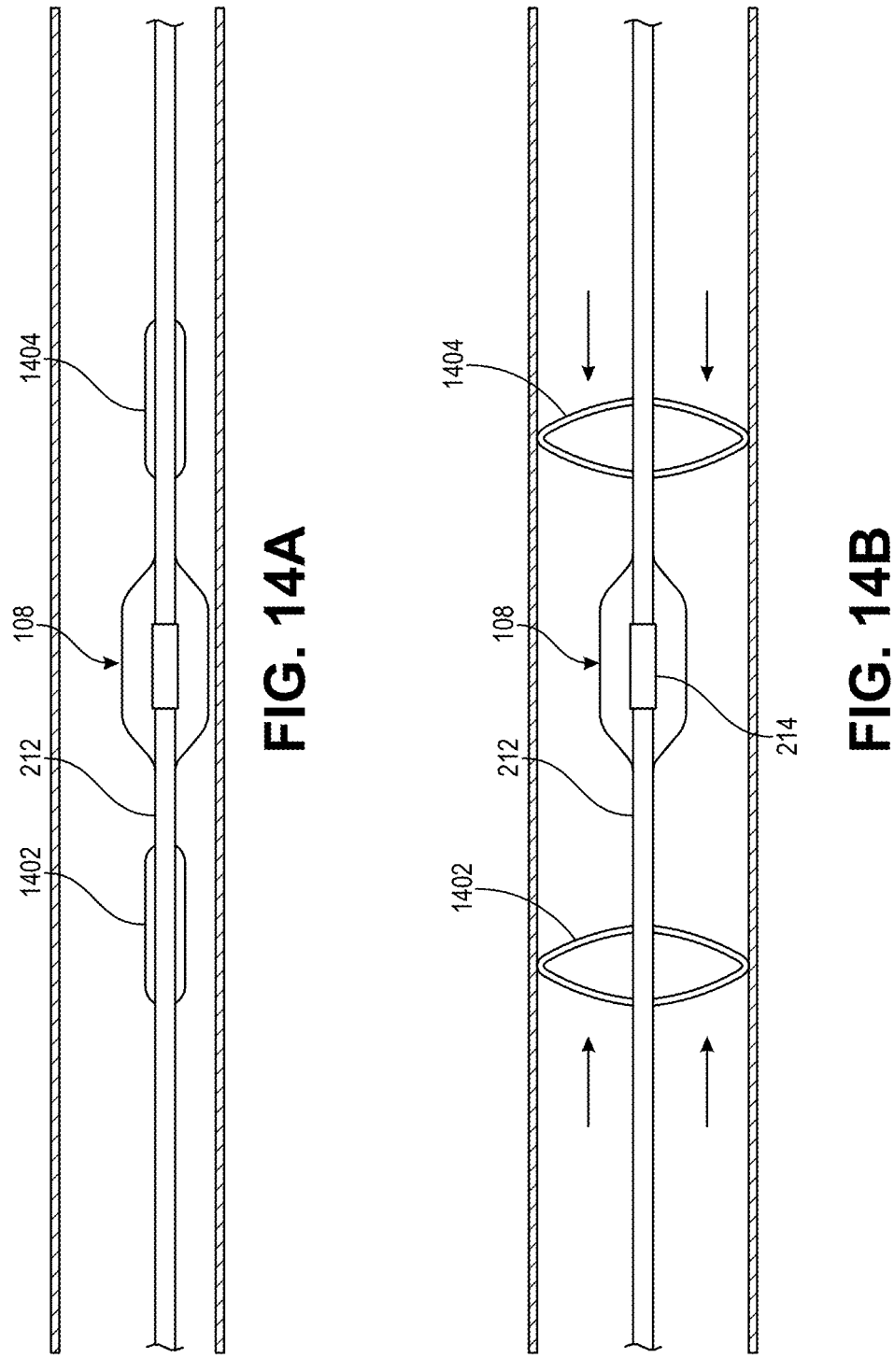
FIGS. 14A-14B are pictorial views of a tissue treatment system having a centering mechanism, in accordance with an embodiment.

Referring to FIG. 14A, a pictorial view of a tissue treatment system having a centering mechanism in an undeployed state is shown in accordance with an embodiment. In order to treat a wider range of artery sizes with only one device, the compliant balloon 108 may be used in combination with one or more centering mechanisms. At some expansion sizes, the compliant balloon 108 may not provide enough centering force to center the transducer 214 properly and/or reliably in a body lumen. Accordingly, an additional mechanical centering mechanisms may be used to supplement the inherent centering capability of the balloon 108.

The tissue treatment system 100 can include a distal centering mechanism 1402 mounted on the catheter shaft 212 distal to the balloon 108 and/or transducer 214, and a proximal centering mechanism 1404 mounted on the catheter shaft 212 proximal to the balloon 108 and/or transducer 214. The balloon 108 and/or the transducer 214 can be axially between the centering mechanisms. The centering mechanisms can be formed from nickel-titanium alloy, or another shape memory alloy, and thus, may be self-expandable. More particularly, the centering mechanism can be formed from nickel-titanium alloy, and may self-expand from a collapsed state (FIG. 14A) to an expanded state (FIG. 14B). In certain embodiments, the centering mechanisms can include flexible baskets attached to the catheter shaft 212. The centering mechanisms may, however, include other structures, such as the spiral springs described below.

Referring to FIG. 14B, a pictorial view of a tissue treatment system having a centering mechanism in a deployed state is shown in accordance with an embodiment. The centering mechanisms can be contained in a sleeve (not shown), e.g., a tubular sleeve that extends over the distal region 202 of the tissue treatment system 100 during delivery to the target anatomy. The sleeve could be retracted when the catheter 102 is properly position for an ablation to expose the centering mechanism and to allow the self-expandable structures of the centering mechanisms to increase in transverse dimension from the constrained state. When the sleeve is withdrawn, the structures expand to press against the artery wall, centering the transducer 214.

The centering mechanisms can work in conjunction with the balloon 108 to center the transducer 214 within the body lumen when the device is properly positioned for ablation, and can press against the artery wall to center the transducer 214 before the compliant balloon 108 is inflated. Advantageously, the mechanical centering mechanisms may be flexible, allowing the structures to be deployed into the target vessel 302 without predetermining a size of the vessel. More particularly, the structures can be flexible enough to be constrained by the vessel wall 303 when deployed within the target vessel 302.

In an embodiment, the centering mechanisms can include spiral, spring-like supports. For example, the centering mechanisms can include spiral springs, e.g., formed from nickel-titanium alloys, that have first ends attached to the catheter shaft 212, and which extend in a spiral manner around the catheter shaft 212 to second ends radially outward from the catheter shaft 212. As an example, the centering mechanisms can be conical, or tapered, springs that increase from a first diameter at the end connected to the catheter shaft 212 to a second, larger diameter at the end longitudinally separated from the first end.

In an alternative embodiment, instead of, or in addition to, the flexible baskets or the spiral springs, the centering mechanisms may include balloons 108. The balloon centering mechanisms can be stiffer, e.g., less compliant, than the compliant balloon 108 surrounding the transducer 214. More particularly, a durometer of the centering balloons may be higher than a durometer of the compliant balloon 108. The centering balloons can be compliant or semi-compliant. The centering balloons (and any of the supplemental centering mechanisms) can be mounted on the catheter shaft 212 distal and proximal to the transducer 214, and outside of a sonication field created by the transducer 214, such that the centering balloons do not interfere with sonication.

In certain embodiments, the balloon 108 may be integrated with the transducer 214, such that the balloon 108 comprises a hollow piezoelectric material including an inner surface and an outer surface. An inner electrode 404 may be disposed on the inner surface and an outer electrode 406 may be disposed on the outer surface. Such embodiments may advantageously enable access to smaller lumens, e.g., accessory renal arteries, ranging in diameter from about 2 mm to about 9 mm. In certain embodiments, a piezoelectric (PZT) film is attached to the inside of the balloon 108 or other expandable member. The balloon 108 may comprise a polyimide film, nylon, PEBAX®, Pellethane®, e.g., Pellethane® having a durometer of 80 A, Isothane®, e.g., Isothane® having a durometer of 5095 A, 7195 A, or 5055 D, and the combined balloon material and piezoelectric film may advantageously remain flexible. In certain embodiments, the PZT film is only located along a cylindrical portion of the balloon 108, e.g., along a portion of the balloon body 506. The PZT film-coated length may be 3-7 mm, e.g., 5 mm, in length, and may be surrounded by memory-folded ribbed shoulders 510, as described above. The burst pressure of the coated balloon 108 may be greater than 45 psi and may range in size from 2.5 mm to 7 mm.

In certain embodiments, the guidewire lumen 213 may be located proximal to, or share a wall with, the catheter shaft 212. More particularly, the tissue treatment system 100 can include a guidewire lumen 213 have a rapid-exchange design to enable expedited exchange of catheters 102 during a procedure. While such embodiments may increase the speed of a procedure, the displacement of the guidewire lumen 213 from the center of the catheter shaft 212 may result in the transducer 214 being off-centered within the body lumen, thereby causing nonuniform ablations. The centering mechanisms disclosed herein may aid in centering the transducer 214 in certain monorail embodiments. The monorail embodiments may or may not include compliant balloons 108.

Figure 15:
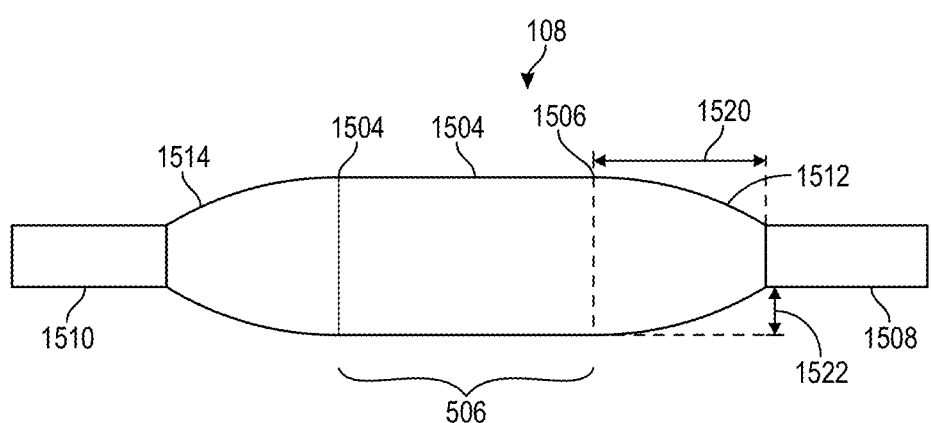
FIG. 15 is a side view of a compliant balloon of a tissue treatment system, in accordance with an embodiment.

Referring to FIG. 15, a side view of a compliant balloon of a treatment system is shown in accordance with an embodiment. The balloon 108 can have a working pressure range of 10 to 30 psi. At a nominal pressure of 10 psi, the balloon 108 can have a diameter of 4.0 mm. At inflation pressure of 30 psi, the balloon 108 can have a diameter of 8.0 mm.

Notably, the balloon 108 can have material and structural (e.g., wall thickness, profile, etc.) characteristics such that at both 10 psi and 30 psi, a balloon body 506 of the balloon 108 can be substantially cylindrical. More particularly, when the balloon 108 outer diameter is measured, the diameter at a proximal end 1502, a midpoint 1504, and a distal end 1506 of the balloon body 506 may have a same diameter within a narrow tolerance. For example, the diameter of the balloon 108 at the proximal end, midpoint, and distal end along the balloon body 506, when inflated to 2 atm, 10 atm, or 30 atm, may be the same within a tolerance of 0.020 inches. Accordingly, the balloon body 506 of the balloon 108 may be cylindrical at both 10 psi and 30 psi inflation pressures. The characteristic of having a balloon body 506 that remains cylindrical over a 20 atm inflation pressure range contributes to effectively centering the transducer 214 and providing good contact with the vessel wall 303 to ensure that ultrasound energy is efficiently transferred from the transducer 214 to the vessel wall 303.

In addition to the cylindrical balloon body 506 of the balloon 108, the balloon 108 can have a well-defined profile that contributes to the effective centering and sonication characteristics described above. In an embodiment, the compliant balloon 108 includes a distal mounting section 1508 and a proximal mounting section 1510. The mounting sections can have cylindrical profiles over their length, and can be mounted on the catheter shaft 212 of the catheter 102. For example, the mounting sections can be adhesive or thermal bonded to the catheter shaft 212. In an embodiment, the mounting sections are differently sized. For example, an inner diameter of the distal mounting section 512 may be less than an inner diameter of the proximal mounting section 514. The inner diameters can conform to respective shafts of the catheter 102 on which the mounting sections are disposed.

Regions of the balloon 108 axially between the balloon body 506 and the mounting sections may be referred to as shoulders. The balloon 108 can include several shoulders, e.g., a distal shoulder 1512 between the balloon body 506 and the distal mounting section 1508, and a proximal shoulder 1514 between the balloon body 506 and the proximal mounting section 1510. When the compliant balloon 108 is inflated to an inflation pressure, e.g., 10 psi and/or 30 psi, the shoulders can have rounded profiles.

As explained above, the rounded profiles of the shoulders during balloon inflation can contribute to effectively centering the balloon 108 within the body lumen. The rounded profiles may be defined by their length and height. For example, the distal shoulder 1512 can have a shoulder length 1520 and a shoulder width 1522. The shoulder length can be a longitudinal distance from the distal end of the balloon body to a proximal end of the distal mounting section. The shoulder width can be a radial distance between an outer surface of the distal mounting section 1508 and a radial location of the balloon body 506. In an embodiment, the shoulder length may be greater than the shoulder width. For example, the shoulder length may be in a range of 0.150 to 0.200 inches and the shoulder width may be in a range of 0.025 to 0.075 inches. Increasing the ratio of shoulder length to shoulder width may contribute to effective centering of the transducer 214 within the body lumen. In an embodiment, the ratio is 3 or greater, i.e., the shoulder length divided by the shoulder width is at least 3.

In addition to an overall profile of the balloon 108, a wall thickness of the balloon is also a factor in contributing to transducer centering. The compliant balloon 108 can have a balloon wall thickness that meets several criteria. The thickness can be high enough to make the balloon wall stiff enough to support the transducer 214 within the body lumen. The wall thickness may be high enough to ensure that the target inflation pressure of 30 psi can be safely and reliably achieved in vivo. And the wall thickness may be low enough to ensure that the wall material does not unduly interfere with ultrasound energy traveling through it from the transducer 214 to the target ablation area. In an embodiment, these criteria are met by a balloon wall 502 having a double wall thickness in a range of 0.0002 to 0.002 inches. More particularly, it is contemplated that the double wall thickness may be in a range of 0.0004 to 0.0014 inches to center the transducer 214 effectively and still be thin enough to transmit 98% or more of the acoustic energy emitted by the transducer 214 to the vessel wall 303.

The double wall thickness can be measured by squeezing together opposing balloon wall portions of the balloon 108 and measuring a thickness of the combined balloon wall portions. It is contemplated that a balloon 108 having the characteristics described above can have a nominal double wall thickness of 0.0009 inches. Such a thickness can transmit approximately 99% of the emitted acoustic energy to the vessel wall 303.

It is noted that power loss due to acoustic attenuation by the balloon wall 502 is linear in relation to the wall thickness. The balloon material can have an acoustic attenuation between 2-3 dB/MHz/CM. For example, the balloon material may have an acoustic attenuation of 2.5 dB/MHz/CM, and assuming a 9.0 MHz acoustic energy source, an 0.0004 inch balloon wall thickness would attenuate 0.0229 dB (translating to 99.47% acoustic energy transmission) while an 0.0014 inch balloon wall thickness would attenuate 0.08 dB (translating to 98.17% acoustic energy transmission). Accordingly, if the wall thickness is increased, the power loss can be compensated for by increasing power output by the acoustic energy source. However, a double wall thickness of 0.0004 inch to 0.0014 inch can provide excellent transmission that reduces the energy output requirements of the generator, provides good balloon flexibility, and properly centers the transducer 214 within the body lumen, as described above. Accordingly, although the balloon wall thickness ranges are not limiting, these ranges have been shown to be effective in achieving desirable performance results.

The balloon 108 having the characteristics described above may also benefit from having few foreign particles or bubbles within the balloon wall 502. Furthermore, a size of any such foreign particles or bubbles may be limited to ensure that voids and other weaknesses in the balloon wall 502 do not lead to balloon failure during use. In an embodiment, the compliant balloon 108 may have no foreign particles or bubbles greater than 0.2 mm². Accordingly, the balloon 108 may be adapted to mechanically support the transducer 214 within the body lumen, and doing so robustly with a reduced likelihood of failure.

In addition to mechanical characteristics of the balloon 108, material processing of the raw material into the balloon 108 can be an important consideration in achieving the balloon characteristics described above. A balloon forming process may include extruding raw balloon material, e.g., Isothane® particles, into a single lumen tubing. The single lumen tubing may thereafter be blown into a balloon mold to form the balloon 108 having the dimensional and mechanical characteristics described above. It has been found that a draw down ratio used during the extrusion of the single lumen tubing can contribute to forming a balloon 108, which in combination with the dimensional characteristics described above, produces a compliant balloon having sufficient stiffness, flexibility, and robustness to reliably center the transducer 214 within a body lumen during sonication. The draw down ratio is a ratio between the inner diameter of the single lumen tubing and an inner diameter of the tool used during extrusion. Typically, the draw down ratio used in balloon manufacturing is 2:1. In an embodiment, the draw down ratio used during processing of the balloon 108 described above is in a range of 1.1:1 to 1.25:1. This lower draw down ratio, although atypical as compared to conventional balloon forming processes, has been shown to result in the beneficial balloon characteristics described above.

Embodiments of a compliant balloon suitable for use in a catheter configured to treat a large range of body lumen diameters is described above. For example, the embodiments of FIGS. 5-6 and 15, as described above, have characteristics suitable for such a catheter 102. It will be appreciated that those characteristics may be combined in alternative embodiments. For example, the embodiments described below with respect to FIGS. 16-20 can include characteristics of the compliant balloons 108 described above. Accordingly, the following description is intended to add to, and not necessarily to replace, any of the description above. Furthermore, the embodiments of FIGS. 5-6 and 15 are not limiting, and other balloon designs having similar characteristics can be provided. For example, the specific compliant balloon embodiments described with respect to FIGS. 21-23 below may include different features, e.g., angular shoulders instead of rounded shoulders, and may still exhibit the benefits described with respect to the embodiments of FIGS. 5-6 and 15. Accordingly, this description is intended to be read as enabling, rather than limiting.

Figure 16:
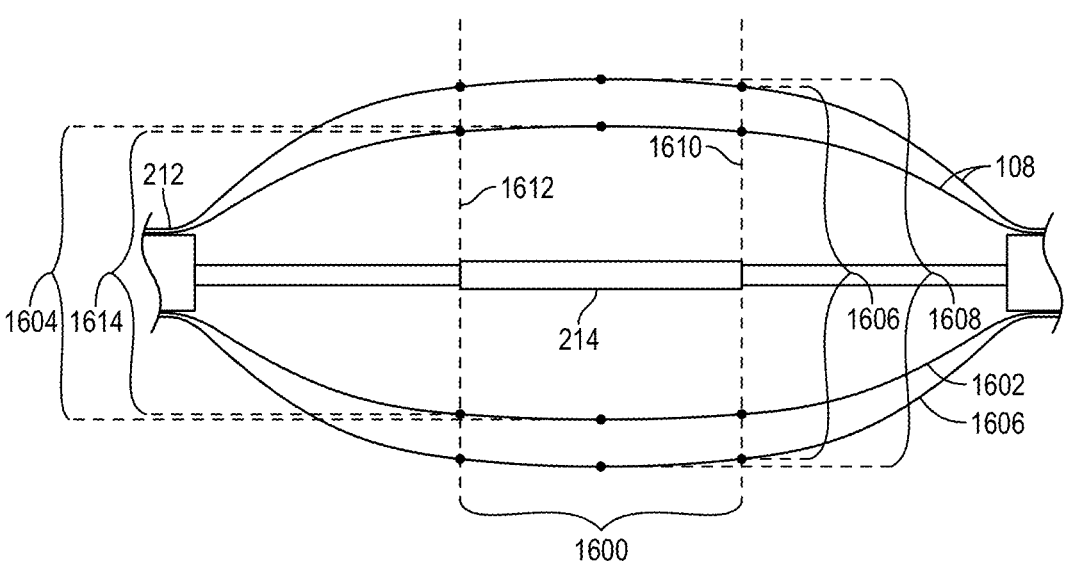
FIG. 16 is a profile view of a compliant balloon of a tissue treatment system, in accordance with an embodiment.

Referring to FIG. 16, a profile view of a compliant balloon of a treatment system is shown in accordance with an embodiment. As described above, the treatment system includes the compliant balloon 108 mounted on the catheter shaft 212. The compliant balloon 108 includes the interior 504 in fluid communication with the fluid channel 420 of the catheter shaft 212. Furthermore, the compliant balloon 108 contains the ultrasound transducer 214 within the interior 504.

It will be appreciated that the profile view illustrates the balloon 108 at two inflation diameters. More particularly, a first profile 1602 represents the balloon 108 when the balloon 108 is inflated such that the balloon body 506 has a first diameter 1604. Similarly, a second profile 1606 represents the balloon 108 when the balloon 108 is inflated such that the balloon body 506 has a second diameter 1608. Accordingly, FIG. 16 illustrates a change in the balloon profile as the balloon 108 inflates from a smaller diameter to a larger diameter. As described above, the balloon 108 may be compliant, and thus, may grow substantially during inflation.

By way of example and not limitation, the first diameter 1604 of the balloon body 506 may be within a range of 3.5 to 6 mm. For example, the first diameter 1604 may be 5 mm. Also by way of example, the second diameter 1608 of the balloon body 506 may be within a range of 8 to 9 mm. For example, the second diameter 1608 may be 8.5 mm. Accordingly, the second diameter 1608 of the balloon 108 may be at least 2 mm greater than the first diameter 1604 of the balloon 108. Due to the balloon compliance, such substantial growth may occur even over relatively small pressure changes. For example, the first profile 1602 may represent the balloon 108 inflated to a first inflation pressure of 2 to 10 psi, e.g., 2 psi, and the second profile 1606 may represent the balloon 108 inflated to a second inflation pressure of 10 to 30 psi, e.g., 12 psi. An inflation pressure of 2 psi can be a native balloon pressure, meaning an inflation pressure at which the balloon 108 expands to an as-molded profile without stretching. The native balloon pressure can be a pressure at which the balloon 108 inflates to a native profile without undergoing plastic deformation. Inflating the balloon 108 above the native inflation pressure, e.g., above 2 psi, can cause the balloon 108 to stretch and expand to a larger profile than the native profile. It will be appreciated that a growth of 2 mm in diameter over a pressure change of 10 psi is characteristic of a compliant balloon, and not a semi-compliant or non-compliant balloon.

In the case of traditional compliant balloons, as the balloon is inflated, the balloon profile will typically take on a spherical shape. The spherical shape produces a balloon body that is also rounded or curved substantially. In contrast, the compliant balloon 108 described herein has a balloon body 506 and/or a working section 1600 of the balloon body 506 that maintains a predetermined straightness, as described below. Maintaining the predetermined straightness over diameter growths of 2 mm or more has a technical effect of allowing for compliant expansion of a balloon against a range of vessel diameters while also maintaining a uniform shape. More particularly, the compliant balloon can have an essentially cylindrical shape both at smaller diameters and relatively larger diameters that differ from the smaller diameters by 2 mm or more. The essentially cylindrical shape may support and center the transducer within the vessels of varying sizes to provide uniform energy delivery in differently sized anatomies.

The balloon body 506 can have a working section 1600 located between the balloon shoulders. The working section 1600 of the balloon wall 502 may be defined with respect to the ultrasound transducer 214. More particularly, the working section 1600 may include the portion of the balloon wall 502 that is radially surrounding the ultrasound transducer 214. In an embodiment, the working section 1600 extends between a distal plane 1610 extending transverse to a central axis of the transducer 214, and a proximal plane 1612 also extending transverse to the central axis. The distal plane 1610 and the proximal plane 1612 can be parallel to each other. The planes can intersect the balloon profile and define the working section 1600 as the portion of the balloon profile or balloon body 506 that is longitudinally between the distal plane 1610 in the proximal plane 1612.

It will be appreciated that the working section 1600, when defined relative to the transducer 214, may be a variable portion of the balloon wall 502. More particularly, at the first diameter 1604, the portion of the balloon wall 502 radially surrounding the ultrasound transducer 214 may be different from the portion of the balloon wall 502 that radially surrounds the ultrasound transducer 214 at the second diameter 1608. Nonetheless, the working section 1600 can have a predetermined straightness when the working section 1600 has both the first diameter 1604 and the second diameter 1608.

The predetermined straightness can be defined in several ways. The compliant balloon 108 can have a substantially cylindrical working section 1600 at both the first diameter 1604 and the second diameter 1608, similar to the balloon body 506 illustrated in, and described with respect to, FIG. 15. The idealized cylindrical balloon body 506 of FIG. 15 may, however, be an approximation of an actual balloon working section. More particularly, the working section 1600 may have some curvature, and may nonetheless be substantially cylindrical. The substantial cylindricity of the working section 1600 can compare favorably to the spherical shapes of typical inflated compliant balloons.

In an embodiment, the predetermined straightness of the working section 1600 includes a cylindricity of the working section 1600 being less than a predetermined threshold. Cylindricity can be defined as a difference between a maximum diameter and a minimum diameter of the working section 1600 over a length of the working section 1600. For example, referring to the first profile 1602, the first diameter 1604 may be measured at a location approximately midway between the distal plane 1610 and the proximal plane 1612. The inflated balloon 108 may have a slight outward curvature along the working section 1600, and thus, the first diameter 1604 may be greater than a diameter of the working section 1600 at either the distal plane 1610 or the proximal plane 1612. More particularly, a first minimum diameter 1614 of the working section 1600 when the balloon 108 has the first profile 1602 may be less than the first diameter 1604. A cylindricity of the working section 1600 when the balloon 108 has the first profile 1602 can be determined by subtracting the first minimum diameter 1614 from the first diameter 1604. In an embodiment, the cylindricity is less than the predetermined threshold. For example, the cylindricity may be less than 1 mm, meaning that a difference between the first diameter 1604 and the first minimum diameter 1614 is 1 mm or less. As a practical example, experimental data has been generated indicating that, when the compliant balloon 108 is inflated to a pressure of 10 psi, the maximum deviation in diameter across the working section 1600 is approximately 0.5 mm. That is, the cylindricity is approximately 0.5 mm, which is less than 1 mm.

A cylindricity of the working section 1600 when the balloon wall 502 has the second profile 1606 can also be less than the predetermined threshold. For example, a difference between the second diameter 1608 measured midway between the distal plane 1610 and the proximal plane 1612, and a second minimum diameter measured at the distal plane 1610, can be less than, e.g., 1 mm. As a practical example, experimental data has been generated indicating that, when the compliant balloon 108 is inflated to a pressure of 30 psi, the maximum deviation in diameter across the working section 1600 is approximately 0.75 mm. That is, the cylindricity is approximately 0.75 mm, which is less than 1 mm.

It will be appreciated that the cylindricity threshold of 1 mm is provided by way of example. As described above, compliant balloons 108 having the substantially cylindrical working sections 506 may have cylindricities below 0.75 mm, 0.5 mm, etc. over their normal inflation range. Accordingly, the cylindricity threshold of 1 mm is not limiting. The predetermined threshold of cylindricity may be between 0.25 to 1 mm. Nonetheless, such cylindricity is understood to be relatively straight as compared to typical compliant balloons that inflate to spherical shapes. The cylindricity contributes to effectively supporting the transducer 214, and thus, when the compliant balloon 108 is inflated to the second inflation pressure, the ultrasound transducer 214 is radially centered within the compliant balloon 108. Additional manners of defining the predetermined straightness are described below.

Figure 17:
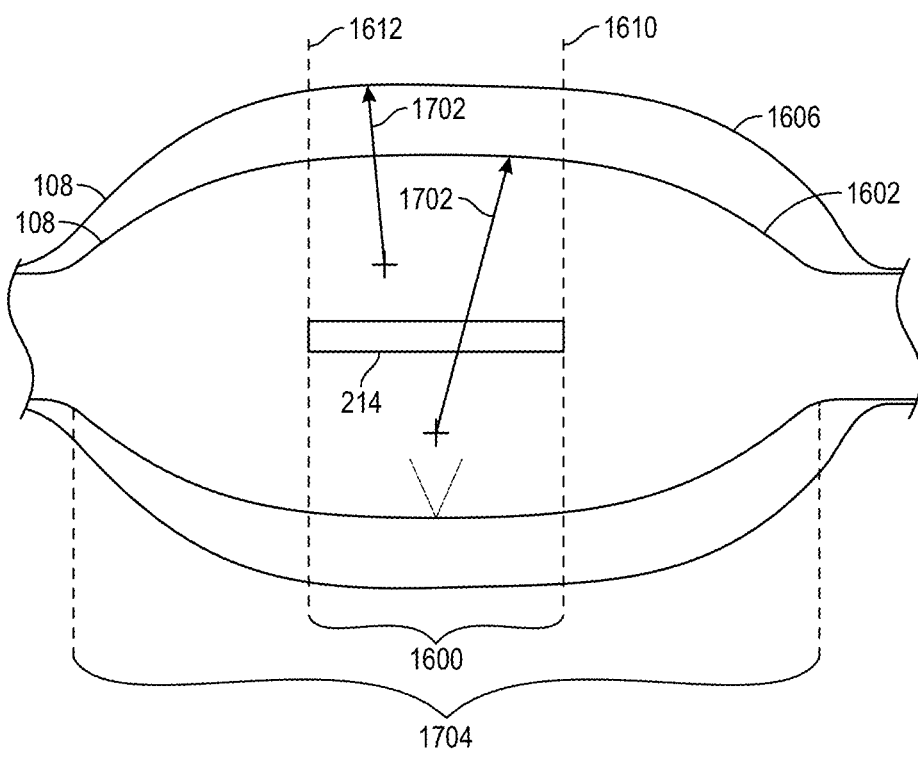
FIG. 17 is a profile view of a compliant balloon of a tissue treatment system, in accordance with an embodiment.

Referring to FIG. 17, a profile view of a compliant balloon of a treatment system is shown in accordance with an embodiment. The illustrated profiles can be characteristic of the compliant balloon 108 inflated in free space (unconstrained and outside of a body vessel) at several inflation pressures. Furthermore, the profiles may be characteristic of a compliant balloon 108 formed from Pellethane®, and sized and shaped to be used in the hybrid approach described above. The first profile 1602 may be assumed by the balloon wall 502 when the balloon 108 is inflated to an inflation pressure of 2 psi. The second profile 1606 may be assumed by the balloon wall 502 when the balloon 108 is inflated to an inflation pressure of 20 psi.

In an embodiment, the predetermined straightness of the working section 1600 can include a ratio of a measurement of the working section 1600 relative to a measurement of the entire balloon 108. For example, the ratio of a radius of curvature 1702 of the working section 1600 to a length 1704 of the compliant balloon 108 may be greater than the predetermined threshold. The curvature of the working section 1600 may be defined by a radius of curvature 1702. The radius of curvature 1702 can be a distance from an imaginary point to the balloon wall 502, where the imaginary point is situated such that the distance from the imaginary point to each point along the working section 1600 is equal. The length 1704 of the compliant balloon 108 may be measured from a proximal location at which the balloon wall 502 meets the catheter shaft 212 to a distal location at which the balloon wall 502 meets the catheter shaft 212. In the example, the predetermined threshold may be 1.0. Accordingly, the radius of curvature 1702 of the working section 1600 can be greater than the length 1704 of the compliant balloon 108. Such predetermined threshold is provided by way of example, however, and other predetermined thresholds may be used which also represent substantial straightness of the compliant balloon 108.

It will be appreciated that as the balloon 108 inflates, the radius of curvature 1702 can decrease. More particularly, as the balloon 108 inflates, the curvature of the working section 1600 may become slightly more pronounced, and thus, the radius of curvature 1702 will decrease. Nonetheless, when the balloon 108 is inflated to the second profile 1606, the ratio of the radius of curvature 1702 to the length 1704 of the compliant balloon 108 can be less than the predetermined threshold. For example, the ratio of the radius of curvature 1702 of the balloon working section 1600 to a length 1704 of the balloon, when the balloon has the second profile 1606, may be greater than 1.0. It will be appreciated that the illustrated radii of curvature in FIG. 17 are not longer than the balloon 108 length 1704. This is so because the actual radius of curvatures 1702 may not even fit on the drawing sheet, given that the working section 1600 is so straight. Accordingly, the illustrated radii are provided for visualization purposes only, and are not intended to limit the description.

Figure 18:
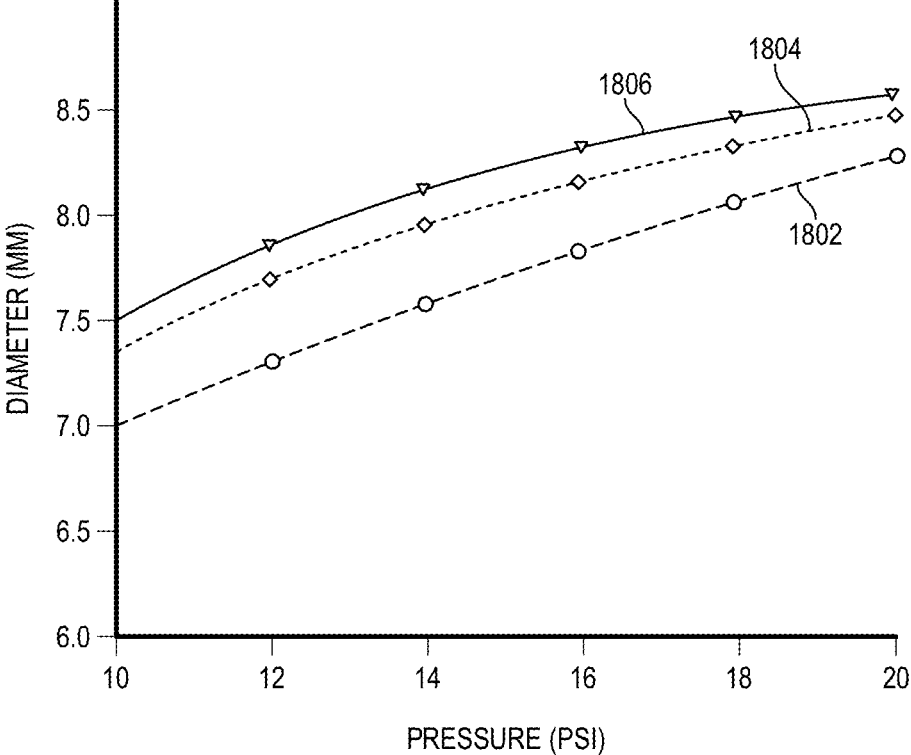
FIG. 18 is a diagram of balloon pressure curves of a compliant balloon being inflated sequentially into free space, in accordance with an embodiment.

Referring to FIG. 18, a diagram of balloon pressure curves of a compliant balloon being inflated sequentially into free space is shown in accordance with an embodiment. The compliance curves represent inflation diameters 704 of the balloon 108 described with respect to FIG. 17 at various inflation pressures over several runs. More particularly, each run has a respective compliance curve that varies as the balloon 108 is inflated and deflated several times. For example, the compliance curve for a first run 1802 has an initial inflation diameter of 7.0 mm at an inflation pressure of 10 psi, and then progressively increases in diameter to 8.3 mm at an inflation pressure of 20 psi.

The compliance curve for a second run 1804 shifts upward relative to the first run 1802. For example, the compliance curve for the second run 1804 has an initial inflation diameter of 7.4 mm at an inflation pressure of 10 psi, and then progressively increases in diameter to 8.5 mm at an inflation pressure of 20 psi. Similarly, the compliance curve for the fifth run 1806 shifts upward relative to the second run 1804. For example, the compliance curve for the fifth run 1806 has an initial inflation diameter of 7.5 mm at an inflation pressure of 10 psi, and then progressively increases in diameter to 8.6 mm at an inflation pressure of 20 psi.

Compliance curves for a third and fourth run of the compliant balloon 108 are omitted to avoid clutter, however, it will be appreciated that those compliance curves would fit in between the second run 1804 and the fifth run 1806. More particularly, differences in diameters at each inflation pressure for the third run and the fourth run are between the diameters at those inflation pressures for the second run 1804 and the fifth run 1806.

In an embodiment, when the compliant balloon 108 is inflated to an inflation pressure five times, a diameter of the working section 1600 after being inflated a fourth time is within 10% of the diameter of the working section 1600 when being inflated a fifth time. Still referring to FIG. 18, such characteristic is supported by a comparison between the second run 1804 compliance curve and the fifth run 1806 compliance curve. More particularly, at the inflation pressure of 10 psi, the difference in diameters of the working section 1600 during the second run 1804 and the fifth run 1806 is 0.1 mm, which is approximately 1% of the working section diameter during the fifth run 1806. Similarly, at the inflation pressure of 20 psi, the difference in diameters of the working section 1600 during the second run 1804 and the fifth run 1806 is 0.1 mm, which is approximately 1% of the working section diameter during the fifth run 1806. Accordingly, the diameter of the working section 1600 over sequential runs is tightly controlled and therefore the balloon 108 will apply similar pressure to the vessel wall 303 during each sequential inflation.

Figure 19:
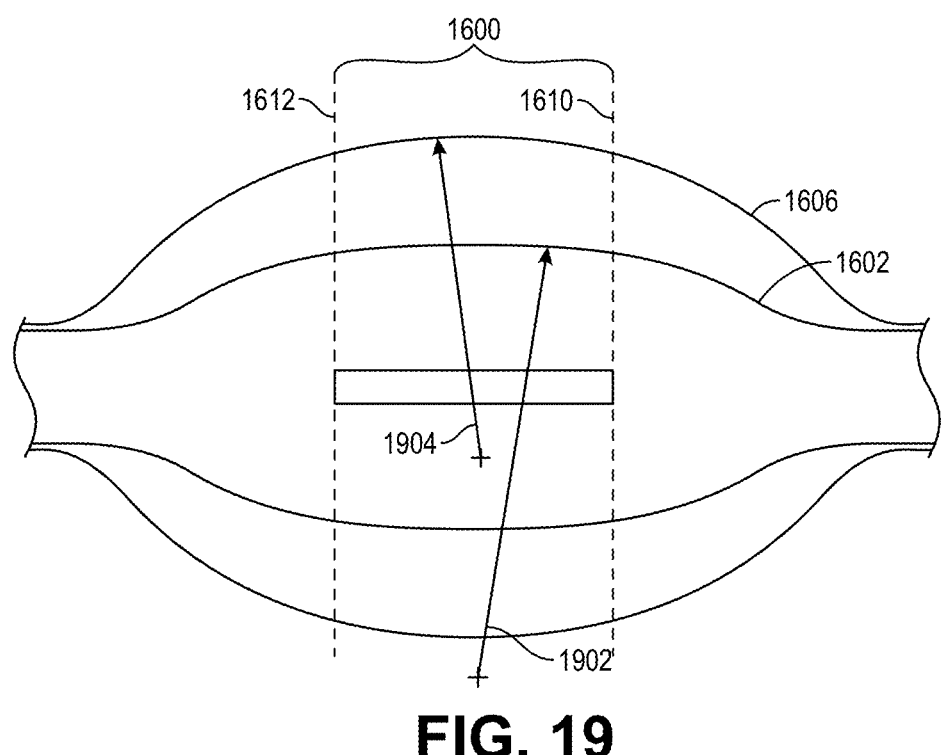
FIG. 19 is a profile view of a compliant balloon of a tissue treatment system, in accordance with an embodiment.

Referring to FIG. 19, a profile view of a compliant balloon of a treatment system is shown in accordance with an embodiment. The illustrated profiles can be characteristic of the compliant balloon 108 inflated in free space (unconstrained and outside of the blood vessel) at several inflation pressures. Furthermore, the profiles may be characteristic of a compliant balloon 108 formed from Isothane®, and sized and shaped to be used in the hybrid approach described above. The first profile 1602 may be assumed by the balloon wall 502 when the balloon 108 is inflated to an inflation pressure of 2 psi. The second profile 1606 may be assumed by the balloon wall 502 when the balloon 108 is inflated to an inflation pressure of 20 psi.

In an embodiment, the predetermined straightness of the working section 1600 can include a difference between a measurement of the working section 1600 when measured at each inflation state. For example, the difference between a first radius of curvature 1902 of the working section 1600 when the working section has the first diameter of the first profile 1602 may be within a predetermined percent difference of a second radius of curvature 1904 of the working section 1600 when the working section has the second diameter of the second profile 1606. As described above, the radius of curvature can be a distance from an imaginary point to the balloon wall 502, where the imaginary point is situated such that the distance from the imaginary point to each point along the working section 1600 is equal. By way of example, the predetermined percent difference can be 30% or less, e.g., 20%. Accordingly, in an embodiment, the first radius of curvature 1902 is within 20% of the second radius of curvature 1904. Such predetermined threshold is provided by way of example, however, and other predetermined thresholds may be used which also represent substantial straightness of the compliant balloon 108.

It will be appreciated that as the balloon 108 inflates, the radius of curvature 1702 can decrease. More particularly, as the balloon 108 inflates, the curvature of the working section 1600 may become slightly more pronounced, and thus, the radius of curvature 1702 will decrease. Nonetheless, when the balloon 108 is inflated to the second profile 1606, the difference of the radius of curvatures can be less than the predetermined threshold. For example, the percent difference of the radii of curvature when the balloon 108 has the first profile 1602 compared to when the balloon 108 has the second profile 1606 may be less than 20%. It will be appreciated that the illustrated radii of curvature in FIG. 19 are provided for visualization purposes only, and are not intended to limit the description.

Figure 20:
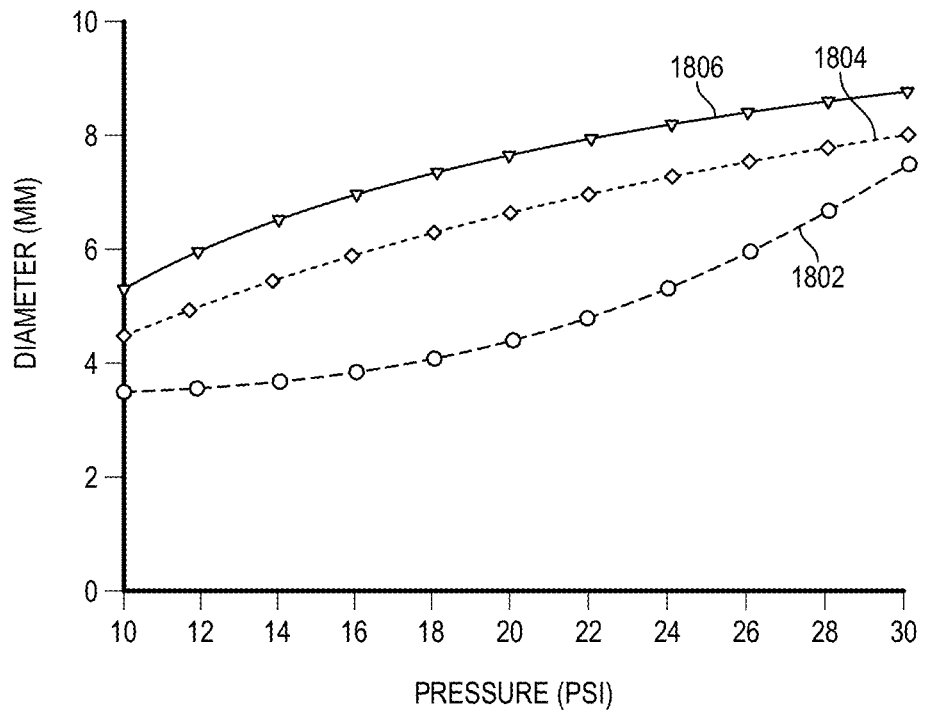
FIG. 20 is a diagram of balloon pressure curves of a compliant balloon being inflated sequentially into free space.

Referring to FIG. 20, a diagram of balloon pressure curves of a compliant balloon being inflated sequentially into free space. The compliance curves represent inflation diameters 704 of the balloon 108 described with respect to FIG. 19 at various inflation pressures over several runs. More particularly, each run has a respective compliance curve that varies as the balloon 108 is inflated and deflated several times. For example, the compliance curve for a first run 1802 has an initial inflation diameter of 3.5 mm at an inflation pressure of 10 psi, and then progressively increases in diameter to 7.5 mm at an inflation pressure of 30 psi.

The compliance curve for a second run 1804 shifts upward relative to the first run 1802. For example, the compliance curve for the second run 1804 has an initial inflation diameter of 4.5 mm at an inflation pressure of 10 psi, and then progressively increases in diameter to 8.0 mm at an inflation pressure of 30 psi. Similarly, the compliance curve for the fifth run 1806 shifts upward relative to the second run 1804. For example, the compliance curve for the fifth run 1806 has an initial inflation diameter of 5.3 mm at an inflation pressure of 10 psi, and then progressively increases in diameter to 8.3 mm at an inflation pressure of 30 psi.

Compliance curves for a third and fourth run of the compliant balloon 108 are omitted to avoid clutter, however, it will be appreciated that those compliance curves would fit in between the second run 1804 and the fifth run 1806. More particularly, differences in diameters at each inflation pressure for the third run and the fourth run are between the diameters at those inflation pressures for the second run 1804 and the fifth run 1806.

In an embodiment, when the compliant balloon 108 is inflated to an inflation pressure five times, a diameter of the working section 1600 when being inflated the fourth time is within 20% of the diameter of the working section 1600 when being inflated the fifth time. Still referring to FIG. 20, such characteristic is supported by a comparison between the second run 1804 compliance curve and the fifth run 1806 compliance curve. More particularly, at the inflation pressure of 10 psi, the difference in diameters of the working section 1600 during the second run 1804 and the fifth run 1806 is 0.8 mm, which is approximately 15% of the working section diameter during the fifth run 1806. Similarly, at the inflation pressure of 30 psi, the difference in diameters of the working section 1600 during the second run 1804 and the fifth run 1806 is 0.3 mm, which is approximately 4% of the working section diameter during the fifth run 1806. Accordingly, the diameter of the working section 1600 over sequential runs is tightly controlled and therefore the balloon 108 will apply similar pressure to the vessel wall 303 during each sequential inflation.

Notably, the compliance curve of the first run 1802 has a concave upward shape. More particularly, during the first run 1802, balloon diameters over the inflation pressures between 10 to 20 psi increase at a lower rate than balloon diameters over the inflation pressures between 20 to 30 psi. By contrast, the compliance curve profiles of the second run 1804 and the fifth run 1806 have concave downward shapes. The difference in profile shape of the first run 1802, may be attributed to the balloon design. The compliant balloon 108 described with respect to FIG. 19 can be formed with shoulders that are more rounded as compared to the shoulders of the compliant balloon 108 described with respect to FIG. 17. Accordingly, it will be appreciated that the balloon design can be manipulated to adjust the rate of balloon diameter increase over sequential runs.

Referring to both FIG. 17 and FIG. 20, it will be appreciated that the compliance curve of the first run 1802 may be substantially different than the compliance curves of the second and greater runs. In particular, the initial inflation diameter at the inflation pressure of 10 psi can differ substantially between the first and subsequent runs. Such difference may be attributed to a time-dependent polymer chain relaxation of the balloon material that occurs after the balloon 108 is inflated once. Due to the relaxation, the initial inflation diameter may increase after the first run 1802 is complete. Relaxation of the balloon material may plateau after the first run 1802, however, and initial inflation diameters 704 between the second and subsequent runs may be similar. It is contemplated that this balloon characteristic may be exploited to ensure that sequential inflations of the balloon 108 within the target lumen are similar. For example, the balloon 108 may be inflated several times outside of the patient to cause the balloon material to relax. The balloon 108 may then be deployed into the target vessel 302, as described above, and inflated one or more times to closely controlled diameters corresponding to the compliance curves of the second and greater runs.

The tight control of inflation diameters over sequential runs can be expressed in different terms than percent difference of working section diameter. In an embodiment, a run-to-run stability of the balloon 108 can be expressed in terms of a standard deviation of a maximum diameter of the working section 106. For example, when a same balloon is inflated over a range of inflation pressures of 10 to 30 psi during a third through fifth run, a standard deviation of the maximum diameter of the working section 106 can be less than 0.2 mm. The maximum diameter can be measured at a longitudinal midpoint of the balloon. Accordingly, when a balloon is inflated five times to an inflation pressure of 20 psi, a standard deviation of the maximum diameter of the balloon measured during the third, fourth, and fifth runs can be 0.2 mm or less.

A generalized description of the balloon 108 is provided above, and it will be appreciated that the concepts included in the generalized description may be applied to develop a compliant balloon having the advantageous characteristics described. Some of the dimensions of the balloons illustrated in FIGS. 21-23 can be identical to those described above. For example, the balloon double wall thickness can be 0.0009 inch. Other dimensions may vary, however. Accordingly, to further describe the balloon 108, several specific examples of balloons and respective dimensions are provided below.

Figure 21:
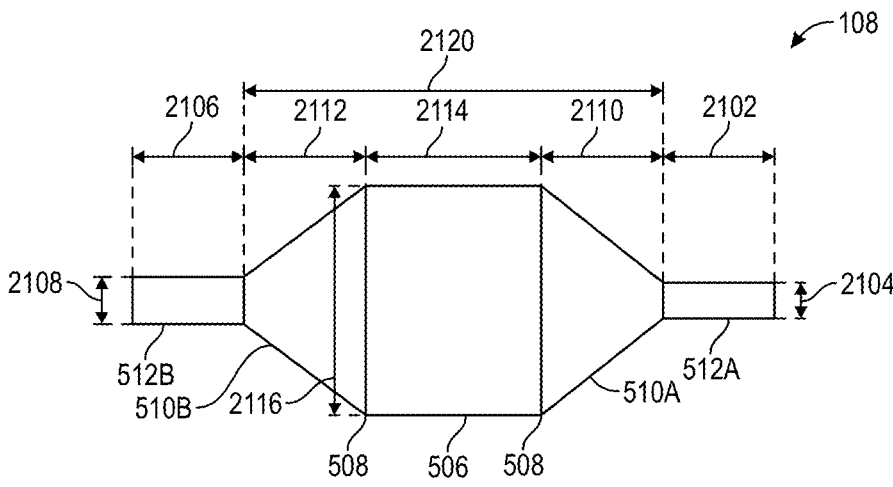
FIGS. 21-23 are side views of various compliant balloons in accordance with several embodiments.

Referring to FIG. 21, a side view of a compliant balloon is shown in accordance with an embodiment. The balloon 108 may be used in the arterial limiting approach described above. The balloon 108 may be formed from the materials described above. The balloon 108 can include portions corresponding to those described above with respect to, e.g., FIG. 5. More particularly, the portions of the balloon can include mounting sections, shoulders, corners, and a balloon body, having respective lengths and characterized by respective diameters at a given inflation pressure. The balloon 108 is illustrated in FIG. 21 at a nominal (native) inflation pressure of 2 ATM. Each of the balloon portions and their respective dimensions are described in further detail below.

The distal mounting section 512A can have a distal mounting section length 2102 and a distal mounting section diameter 2104. The distal mounting section length 2102 can be 0.155 to 0.160 inch, e.g., 0.157 inch. The distal mounting section diameter 2104 can be 0.050 to 0.055 inch, e.g., 0.052 inch.

The proximal mounting section 512B can have a proximal mounting section length 2106 and a proximal mounting section diameter 2108. The proximal mounting section length 2106 can be 0.155 to 0.160 inch, e.g., 0.157 inch. The proximal mounting section diameter 2108 can be 0.060 to 0.070 inch, e.g., 0.064 inch.

The distal shoulder 510A and the proximal shoulder 510B can have respective shoulder lengths 2110 and 2112. For example, the shoulder lengths can be 0.150 to 0.200 inch, e.g., 0.170 inch. One or more of the distal shoulder 510A and the proximal shoulder 510B can transition into the working length 506 at respective corners 508A, 508B. It will be appreciated that the corners can be angular, rather than rounded. The angular shoulders can be evident at the native inflation pressure. When inflated above the native inflation pressure, the angular corners may round slightly. The angular corners in the native diameter balloon can provide effective support and centering of the transducer 214 within a target vessel.

The balloon body 506 can have a balloon body length 2114 and a balloon body diameter 2116. The balloon body length 2114 can be 0.245 to 0.255 inch, e.g., 0.250 inch. The balloon body diameter 2116 can be 7.5 to 8.5 mm, e.g., 8.0 mm. An overall length 2120 of the balloon 108 can be measured between the proximal and distal mounting sections. The overall length 2120 can include the lengths of the balloon body 506 and the shoulders 510A, 510B. In an embodiment, the overall length 2120 is 0.550 to 0.650 inch, e.g., 0.590 inch.

Figure 22:
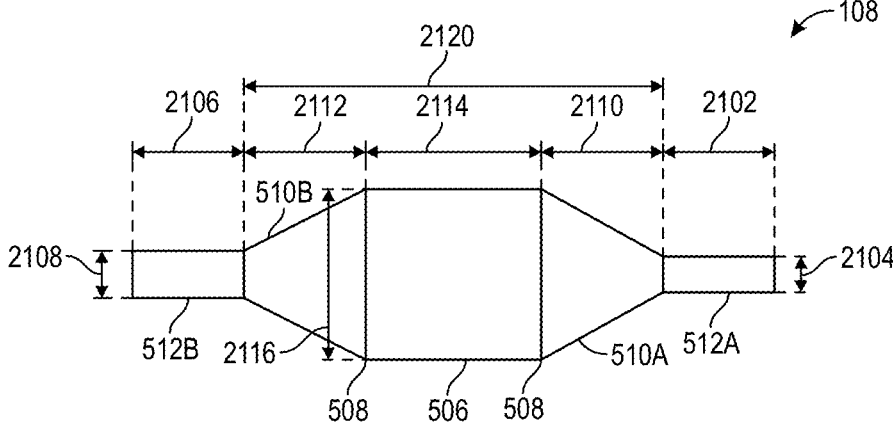

Referring to FIG. 22, a side view of a compliant balloon is shown in accordance with an embodiment. The balloon 108 may be used in the hybrid inflation approach described above. The balloon 108 may be formed from the materials described above. The balloon 108 can include portions corresponding to those described above with respect to, e.g., FIG. 5. More particularly, the portions of the balloon can include mounting sections, shoulders, corners, and a balloon body, having respective lengths and characterized by respective diameters at a given inflation pressure. The balloon 108 is illustrated in FIG. 22 at a nominal (native) inflation pressure of 2 ATM. Each of the balloon portions and their respective dimensions are described in further detail below.

The distal mounting section 512A can have a distal mounting section length 2102 and a distal mounting section diameter 2104. The distal mounting section length 2102 can be 0.155 to 0.160 inch, e.g., 0.157 inch. The distal mounting section diameter 2104 can be 0.050 to 0.055 inch, e.g., 0.052 inch.

The proximal mounting section 512B can have a proximal mounting section length 2106 and a proximal mounting section diameter 2108. The proximal mounting section length 2106 can be 0.155 to 0.160 inch, e.g., 0.157 inch. The proximal mounting section diameter 2108 can be 0.060 to 0.070 inch, e.g., 0.064 inch.

The distal shoulder 510A and the proximal shoulder 510B can have respective shoulder lengths 2110 and 2112. For example, the shoulder lengths can be 0.150 to 0.200 inch, e.g., 0.170 inch. One or more of the distal shoulder 510A and the proximal shoulder 510B can transition into the working length 506 at respective corners 508A, 508B. It will be appreciated that the corners can be angular, rather than rounded. The angular shoulders can be evident at the native inflation pressure. When inflated above the native inflation pressure, the angular corners may round slightly. The angular corners in the native diameter balloon can provide effective support and centering of the transducer 214 within a target vessel.

The balloon body 506 can have a balloon body length 2114 and a balloon body diameter 2116. The balloon body length 2114 can be 0.245 to 0.255 inch, e.g., 0.250 inch. The balloon body diameter 2116 can be 5.5 to 6.5 mm, e.g., 6.0 mm. An overall length 2120 of the balloon 108 can be measured between the proximal and distal mounting sections. The overall length 2120 can include the lengths of the balloon body 506 and the shoulders 510A, 510B. In an embodiment, the overall length 2120 is 0.550 to 0.650 inch, e.g., 0.590 inch.

Figure 23:
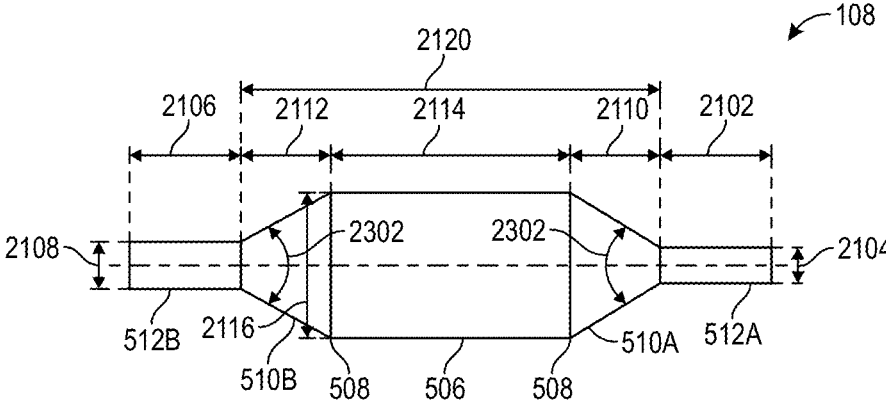

Referring to FIG. 23, a side view of a compliant balloon is shown in accordance with an embodiment. The balloon 108 may be used in the hybrid inflation approach described above. The balloon 108 may be formed from the materials described above, such as Isothane® having a Shore D durometer of 55. The balloon 108 can include portions corresponding to those described above with respect to, e.g., FIG. 5. More particularly, the portions of the balloon can include mounting sections, shoulders, corners, and a balloon body, having respective lengths and characterized by respective diameters at a given inflation pressure. The balloon 108 is illustrated in FIG. 22 at a nominal (native) inflation pressure of 2 ATM. Each of the balloon portions and their respective dimensions are described in further detail below.

The distal mounting section 512A can have a distal mounting section length 2102 and a distal mounting section diameter 2104. The distal mounting section length 2102 can be at least 0.0157 inch. The distal mounting section diameter 2104 can be 0.050 to 0.055 inch, e.g., 0.052 inch.

The proximal mounting section 512B can have a proximal mounting section length 2106 and a proximal mounting section diameter 2108. The proximal mounting section length 2106 can be at least 0.157 inch. The proximal mounting section diameter 2108 can be 0.060 to 0.070 inch, e.g., 0.062 inch.

The distal shoulder 510A and the proximal shoulder 510B can have respective shoulder lengths 2110 and 2112. For example, the shoulder lengths can be 0.075 to 0.110 inch, e.g., 0.098 inch. One or more of the distal shoulder 510A and the proximal shoulder 510B can transition into the working length 506 at respective corners 508A, 508B. It will be appreciated that the corners can be angular, rather than rounded. The angular shoulders can be evident at the native inflation pressure. When inflated above the native inflation pressure, the angular corners may round slightly. The angular corners in the native diameter balloon can provide effective support and centering of the transducer 214 within a target vessel.

The balloon body 506 can have a balloon body length 2114 and a balloon body diameter 2116. The balloon body length 2114 can be 0.250 to 0.300 inch, e.g., 0.276 inch. The balloon body diameter 2116 can be 4.25 to 4.75 mm, e.g., 4.5 mm at the native inflation pressure. At an inflation pressure of 30 psi, the balloon body diameter 2116 may be 8 mm. An overall length 2120 of the balloon 108 can be measured between the proximal and distal mounting sections. The overall length 2120 can include the lengths of the balloon body 506 and the shoulders 510A, 510B. In an embodiment, the overall length 2120 is 0.425 to 0.525 inch, e.g., 0.472 inch.

The balloon 108 may include a cone angle 2302 corresponding to an angle that one or more of the shoulders have relative to a central axis of the balloon. The cone angle 2302 may be a full angle, e.g., an angle measured between opposite sides of the shoulder. In an embodiment, the cone angle 2302 can be between 55° to 70°. For example, the cone angle 2302 can be 60° or 65°. The cone angle 2302 of the distal shoulder 510A may differ from the cone angle 2302 of the proximal shoulder 510B. For example, the distal shoulder 510A can have a cone angle 2302 of 65°, and the proximal shoulder 510B can have a cone angle of 60°.

Embodiments of a tissue treatment system are described above. More particularly, embodiments of the tissue treatment system are described, either explicitly or implicitly. The following paragraphs summarize some of the described embodiments.

In an embodiment, a catheter includes a catheter shaft having a fluid channel. The catheter includes an ultrasound transducer. The catheter includes a compliant balloon mounted on the catheter shaft and having an interior in fluid communication with the fluid channel and containing the ultrasound transducer. The compliant balloon includes a balloon wall having a working section radially surrounding the ultrasound transducer. The working section has a pre-determined straightness when the working section has a first diameter and when the working section has a second diameter that is at least 2 mm greater than the first diameter.

In an embodiment, the first diameter is within a range of 3.5 to 6 mm. The second diameter is within a range of 8 to 9 mm.

In an embodiment, the first diameter is 5 mm. The second diameter is 8.5 mm.

In an embodiment, the predetermined straightness includes a cylindricity of the working section being less than 1 mm.

In an embodiment, the predetermined straightness includes a ratio of a radius of curvature of the working section to a length of the compliant balloon being greater than 1.

In an embodiment, the predetermined straightness includes a first radius of curvature of the working section when the working section has the first diameter being within 20% of a second radius of curvature of the working section when the working section has the second diameter.

In an embodiment, the compliant balloon has a first inflation pressure of 2 psi to 10 psi when the working section has the first diameter. The compliant balloon has a second inflation pressure of 30 psi when the working section has the second diameter.

In an embodiment, when the compliant balloon is inflated to the second inflation pressure five times, a fourth diameter of the working section when being inflated a fourth time is within 10% of a fifth diameter of the working section when being inflated a fifth time.

In an embodiment, when the compliant balloon has the second inflation pressure, the ultrasound transducer is radially centered within the compliant balloon.

In an embodiment, fluid is circulated through the interior at a flow rate of 15 to 35 mL/min to inflate the compliant balloon to the first inflation pressure. Fluid is circulated through the interior at a flow rate of 35 to 50 mL/min to inflate the compliant balloon to the second inflation pressure.

In an embodiment, the balloon wall includes a proximal shoulder proximal to the working section, and a distal shoulder distal to the working section. The proximal shoulder and the distal shoulder are rounded.

In an embodiment, the proximal shoulder and the distal shoulder include several longitudinal ribs.

In an embodiment, the balloon wall is thicker at the proximal shoulder and the distal shoulder than at the work-ing section.

In an embodiment, the compliant balloon is formed from an elastomeric material.

In an embodiment, the elastomeric material includes a polyether-based thermoplastic polyurethane.

In an embodiment, the polyether-based thermoplastic polyurethane has a Shore D durometer in a range of 50 to 60.

In an embodiment, the polyether-based thermoplastic polyurethane has a Shore D durometer of 55.

In an embodiment, the balloon wall includes no foreign particles or bubbles greater than 0.2 mm$^2$.

In an embodiment, the working section of the balloon wall has a double wall thickness of 0.0004 inch to 0.0014 inch.

In an embodiment, a distal centering mechanism mounted on the catheter shaft distal to the compliant balloon, and a proximal centering mechanism mounted on the catheter shaft proximal to the compliant balloon.

In an embodiment, the compliant balloon is configured to treat a blood vessel having a vessel lumen diameter between 3 mm to 9 mm in diameter.

In an embodiment, the blood vessel is a renal artery.

In an embodiment, a method includes advancing a cath-eter of a tissue treatment system into the target vessel having a vessel wall. The catheter includes a catheter shaft having a fluid channel, an ultrasound transducer, and a compliant balloon mounted on the catheter shaft and having an interior in fluid communication with the fluid channel and contain-ing the ultrasound transducer. The compliant balloon includes a balloon wall having a working section radially surrounding the ultrasound transducer. The working section has a predetermined straightness when the working section has a first diameter and when the working section has a second diameter that is at least 2 mm greater than the first diameter. The method includes inflating the compliant bal-loon to an inflation pressure against the vessel wall. The method includes delivering ultrasonic energy from the ultra-sound transducer to the vessel wall.

In an embodiment, the target vessel includes a vessel lumen diameter smaller than a nominal inflation diameter of the compliant balloon such that a hoop strength of the target vessel prevents the compliant balloon from expanding to the nominal inflation diameter of the compliant balloon.

In an embodiment, the constrained compliant balloon includes several wrinkles at the vessel wall.

In an embodiment, the target vessel includes a vessel lumen diameter larger than a nominal inflation diameter of the compliant balloon such that the inflation pressure expands the compliant balloon to a diameter that is larger than the nominal inflation diameter of the compliant balloon.

In an embodiment, inflating the compliant balloon includes circulating fluid within the compliant balloon at a first flow rate to inflate the compliant balloon to the inflation pressure.

In an embodiment, circulating fluid within the compliant balloon is based on a lumen diameter of the target vessel.

In an embodiment, inflating the compliant balloon includes inflating the compliant balloon to a predetermined inflation pressure regardless of a lumen diameter of the target vessel. The target vessel constrains the compliant balloon.

In an embodiment, a kit includes a first catheter including a first catheter shaft having a first compliant balloon mounted on the first catheter shaft and having a first interior in fluid communication with a first fluid channel of the first catheter and containing a first ultrasound transducer. The first compliant balloon has a first inflation diameter range when fluid is circulated through the first fluid channel at a first flow rate to cause a first inflation pressure in a range of 10 to 30 psi. The kit includes a second catheter including a second catheter shaft having a second compliant balloon mounted on the second catheter shaft and having a second interior in fluid communication with a second fluid channel of the second catheter and containing a second ultrasound transducer. The second compliant balloon has a second inflation diameter range when fluid is circulated through the second fluid channel at a second flow rate to cause a second inflation pressure in a range of 10 to 30 psi. The respective compliant balloons include respective balloon walls having respective working sections radially surrounding the respective ultrasound transducers. The respective working sections have a predetermined straightness when the respective working sections have the respective inflation diameter ranges. The first inflation diameter range overlaps the second inflation diameter range.

In an embodiment, the first inflation diameter range is 3 to 5 mm. The second inflation diameter range is 4 mm to 9 mm.

In an embodiment, a tissue treatment system is configured to treat renal arteries of various sizes and includes a catheter including a catheter shaft having an inlet channel and an outlet channel. The catheter includes an ultrasound transducer mounted on the catheter shaft. The catheter includes a compliant balloon mounted on the catheter shaft. The compliant balloon has an interior in fluid communication with the inlet channel and the outlet channel. The catheter includes a balloon wall having a shape and a stiffness such that when the compliant balloon is inflated to a first inflation pressure of 10 psi, a working section of the balloon wall has a cylindrical profile and a first inflation diameter of 3.5 mm to 6 mm, and when the compliant balloon is inflated to a second inflation pressure of 30 psi, the working section has the cylindrical profile and a second inflation diameter of 8 to 9 mm.

In an embodiment, a tissue treatment system is configured to treat renal arteries of various sizes. The tissue treatment system includes a catheter including a catheter shaft having an inlet channel and an outlet channel. The catheter includes an ultrasound transducer mounted on the catheter shaft. The catheter includes a compliant balloon mounted on the catheter shaft. The compliant balloon has an interior in fluid communication with the inlet channel and the outlet channel, and includes a balloon wall having a shape and a stiffness such that when fluid is circulated through the interior between the inlet channel and the outlet channel at a flow rate of 15 to 35 mL/min, the compliant balloon is inflated to a first inflation pressure of 10 psi and a working section of the balloon wall has a cylindrical profile and a first inflation diameter of 3.5 mm to 6 mm, and when fluid is circulated through the interior between the inlet channel and the outlet channel at a flow rate of 35 to 50 mL/min, the compliant balloon is inflated to a second inflation pressure of 30 psi and the working section has the cylindrical profile and a second inflation diameter of 8 to 9 mm.

In an embodiment, the balloon wall has a shape and a stiffness such that when fluid is circulated through the interior between the inlet channel and the outlet channel at the flow rate of 30 mL/min, the compliant balloon is inflated to the first inflation pressure of 10 psi and the working section has the cylindrical profile and the first inflation diameter of 3.5 mm, and when fluid is circulated through the interior between the inlet channel and the outlet channel at the flow rate of 40 to 45 mL/min, the compliant balloon is inflated to the second inflation pressure of 30 psi and the working section has the cylindrical profile and the second inflation diameter of 8 mm.

In an embodiment, when fluid is circulated through the interior between the inlet channel and the outlet channel at the flow rate of 40 to 45 mL/min, the cylindrical profile of the working section has a proximal profile end proximal to the ultrasound transducer and a distal profile end distal to the ultrasound transducer.

In an embodiment, the compliant balloon is formed from a polyether-based thermoplastic polyurethane having a Shore D durometer of 55.

In an embodiment, the balloon wall includes no foreign particles or bubbles greater than 0.2 mm$^2$.

In an embodiment, a vessel wall of the renal artery has a vessel diameter of 3 mm to 9 mm.

In an embodiment, when the catheter is disposed within the renal artery and fluid is circulated through the interior between the inlet channel and the outlet channel, the ultrasound transducer is centered within the renal artery such that ultrasound energy generated by the ultrasound transducer is uniformly distributed around the vessel wall to a depth of 1 mm to 6 mm.

In an embodiment, a tissue treatment system is configured to treat renal arteries of various sizes. The tissue treatment system includes a catheter including a catheter shaft having an inlet channel and an outlet channel. The catheter includes an ultrasound transducer mounted on the catheter shaft. The tissue treatment system includes a compliant balloon mounted on the catheter shaft. The compliant balloon has an interior in fluid communication with the inlet channel and the outlet channel. The compliant balloon includes a distal mounting section and a proximal mounting section mounted on the catheter shaft, and several shoulders connecting respective mounting sections to the working section. The mounting sections have cylindrical profiles. When the compliant balloon is inflated to the first inflation pressure, the shoulders have rounded profiles.

In an embodiment, the rounded profiles of the shoulders have axial lengths between respective mounting sections and the working section that are at least three times larger than a radial dimension between the mounting sections and the working section.

In an embodiment, the compliant balloon is formed from a polyether-based thermoplastic polyurethane having a Shore D durometer of 55.

In an embodiment, the balloon wall includes no foreign particles or bubbles greater than 0.2 mm$^2$.

In an embodiment, when the compliant balloon is inflated to the first inflation pressure five times, a first inflated diameter of the compliant balloon when being inflated a first time is within 10% of a second inflated diameter of the compliant balloon when being inflated a fifth time.

In an embodiment, a vessel wall of the renal artery has a vessel diameter of 3 mm to 9 mm.

In an embodiment, when the catheter is disposed within the renal artery and fluid is circulated through the interior between the inlet channel and the outlet channel, the ultrasound transducer is centered within the renal artery such that ultrasound energy generated by the ultrasound transducer is uniformly distributed around the vessel wall to a depth of 1 mm to 6 mm.

In an embodiment, a tissue treatment system is configured to treat renal arteries of various sizes. The tissue treatment system includes a catheter including a catheter shaft having an inlet channel and an outlet channel. The catheter includes an ultrasound transducer mounted on the catheter shaft. The catheter includes a compliant balloon mounted on the catheter shaft. The compliant balloon has an interior in fluid communication with the inlet channel and the outlet channel. A working section of the compliant balloon has a double wall thickness of 0.0004 inch to 0.0014 inch at a proximal profile end, a middle, and a distal profile end of the working section.

In an embodiment, the compliant balloon is formed from a polyether-based thermoplastic polyurethane having a Shore D durometer of 55.

In an embodiment, the balloon wall includes no foreign particles or bubbles greater than 0.2 mm$^2$.

In an embodiment, when the compliant balloon is inflated to the first inflation pressure five times, a first inflated diameter of the compliant balloon when being inflated a first time is within 10% of a second inflated diameter of the compliant balloon when being inflated a fifth time.

In an embodiment, a vessel wall of the renal artery has a vessel diameter of 3 mm to 9 mm.

In an embodiment, when the catheter is disposed within the renal artery and fluid is circulated through the interior between the inlet channel and the outlet channel, the ultrasound transducer is centered within the renal artery such that ultrasound energy generated by the ultrasound transducer is uniformly distributed around the vessel wall to a depth of 1 mm to 6 mm.

In an embodiment, a tissue treatment system is configured to treat renal arteries of various sizes. The tissue treatment system includes a catheter including a catheter shaft having an inlet channel and an outlet channel. The catheter includes an ultrasound transducer mounted on the catheter shaft. The catheter includes a compliant balloon mounted on the catheter shaft. The compliant balloon has an interior in fluid communication with the inlet channel and the outlet channel, and includes a balloon wall having a shape and a stiffness such that when the compliant balloon is inflated to an inflation pressure five times, a first inflated diameter of the compliant balloon when being inflated a first time is within 10% of a second inflated diameter of the compliant balloon when being inflated a fifth time.

In an embodiment, a tissue treatment system is configured to treat renal arteries of various diameters. The tissue treatment system includes a catheter including a catheter shaft having an inlet channel and an outlet channel. The catheter includes an ultrasound transducer mounted on the catheter shaft. The catheter includes a compliant balloon mounted on the catheter shaft. The compliant balloon has an interior in fluid communication with the inlet channel and the outlet channel, the compliant balloon having a nominal inflation diameter, and includes a balloon wall having a shape and a stiffness such that when the compliant balloon is inflated to a first inflation pressure within a renal artery having a first arterial diameter that is smaller than the nominal inflation diameter of the compliant balloon, the hoop strength of the renal artery and the inflation pressure prevents the compliant balloon from expanding to the nominal inflation diameter of the compliant balloon. When the compliant balloon is inflated to a second inflation pressure higher than the first inflation pressure within a renal artery having a second diameter larger than the nominal inflation diameter of the compliant balloon, the second inflation pressure expands the compliant balloon to a diameter that is larger than the nominal inflation diameter of the compliant balloon.

In an embodiment, the compliant balloon has a nominal inflation diameter of about 4 mm. When the compliant balloon is inflated to a first inflation pressure within a first arterial diameter of a renal artery having a diameter less than 4 mm, the hoop strength of the renal artery and the inflation pressure prevents the compliant balloon from expanding to a diameter larger than the first arterial diameter of the renal artery. When the compliant balloon is inflated to a second inflation pressure higher than the first inflation pressure within a renal artery having a second diameter larger than 4 mm, the second inflation pressure expands the diameter of the compliant balloon to be in apposition with the second diameter of the renal artery.

In an embodiment, the compliant balloon wall is formed from a urethane material having a Shore D durometer in a range of 50 to 60.

In an embodiment, the urethane material has a Shore D durometer of 55.

In an embodiment, the urethane material is Isothane® having a Shore D durometer of 55.

In an embodiment, a method includes advancing a distal region of a catheter of a tissue treatment system into a target vessel having a vessel wall. The distal region includes a balloon mounted on a catheter shaft. The balloon includes a balloon wall having a distal mounting section, a proximal mounting section, and several shoulders connecting the distal mounting section and the proximal mounting section to a working section. The working section and the several shoulders meet at round corners such that, when the balloon is inflated within the target vessel, the catheter shaft remains centered in the target vessel. The method includes circulating fluid within the balloon at a first flow rate to inflate the balloon to a first predetermined inflation pressure within a first portion of a renal artery having a first arterial diameter that is smaller than a nominal inflation diameter of the compliant balloon, the hoop strength of the renal artery and the first predetermined inflation pressure preventing the compliant balloon from expanding to a diameter larger than the first arterial diameter of the renal artery. The method includes delivering ultrasonic energy from the transducer to the first portion of the renal artery. The method includes circulating fluid within the balloon at a second flow rate to inflate the balloon to a second predetermined inflation pressure within a second portion of the renal artery having a second diameter that is larger than the nominal inflation diameter of the compliant balloon, the second inflation pressure expanding the compliant balloon to a diameter that is larger than the nominal inflation diameter of the compliant balloon; and delivering ultrasonic energy from the transducer to the second portion of the renal artery.

In an embodiment, a kit includes a first catheter and a second catheter configured to treat renal arteries of various sizes, each of the catheters including respective catheter shafts having respective inlet channels and respective outlet channels, respective ultrasound transducers mounted on the respective catheters shafts, and respective compliant balloons mounted on the respective catheter shafts. When fluid is circulated through the inlet channel and the outlet channel of the first catheter at a flow rate to cause an inflation pressure of 10 to 30 psi, the compliant balloon inflates to a diameter of 3 mm to 5 mm, and when fluid is circulated through the inlet channel and the outlet channel of the second catheter at the flow rate to cause the inflation pressure of 10 to 30 psi, the compliant balloon inflates to a diameter of 4 mm to 8 mm.

In an embodiment, a tissue treatment system is configured to treat renal arteries of various diameters. The tissue treatment system includes a catheter including a catheter shaft having an inlet channel and an outlet channel. The catheter includes an ultrasound transducer mounted on the catheter shaft. The catheter includes a compliant balloon mounted on the catheter shaft. The compliant balloon has an interior in fluid communication with the inlet channel and the outlet channel, the compliant balloon having a nominal inflation diameter, and includes a balloon wall having a shape and a stiffness such that the compliant balloon is inflated to an inflation pressure within a renal artery of a first arterial diameter smaller than the nominal inflation diameter of the compliant balloon, the hoop strength of the renal artery and the inflation pressure prevents the compliant balloon from expanding to the nominal inflation diameter of the compliant balloon.

In an embodiment, the nominal inflation diameter of the compliant balloon is 8 mm and the inflation pressure is 10 psi.

In an embodiment, the compliant balloon wall is formed from a urethane material having a Shore D durometer in a range of 50 to 60.

In an embodiment, the urethane material has a Shore D durometer of 55.

In an embodiment, the urethane material is Isothane® having a Shore D durometer of 55.

In an embodiment, a medical balloon includes a balloon wall having a distal mounting section, a proximal mounting section, and several shoulders connecting the distal mounting section and the proximal mounting section to a working section. The working section and several shoulders meet at round corners. The balloon wall is formed from a urethane material having a Shore D durometer in a range of 50 to 60.

In an embodiment, the urethane material has a Shore D durometer of 55.

In an embodiment, the medical balloon has a first inflation diameter of about 3.5 mm at a first inflation pressure of 10 psi, and a second inflation diameter of about 8 mm at a second inflation pressure of 30 psi.

In an embodiment, a first inflation diameter when the medical balloon is inflated a first time is within 10% of a first inflation diameter when the medical balloon is inflated a fifth time.

In an embodiment, several shoulders include several longitudinal ribs.

In an embodiment, the balloon wall is thinner at the several shoulders than at the working section.

In an embodiment, a tissue treatment system includes a catheter including a catheter shaft. The tissue treatment system includes a balloon including a balloon wall having a distal mounting section and a proximal mounting section mounted on the catheter shaft. The catheter includes several shoulders connecting the distal mounting section and the proximal mounting section to a working section. The working section and the several shoulders meet at round corners such that, when the balloon is inflated within a target vessel, the catheter shaft remains centered in the target vessel.

In an embodiment, the balloon wall is formed from a urethane material.

In an embodiment, the urethane material has a Shore D durometer in a range of 50 to 60.

In an embodiment, the urethane material has a Shore D durometer of 55.

In an embodiment, the catheter shaft includes an inlet channel and an outlet channel in fluid communication with the balloon to circulate fluid through the balloon at a flow rate between 25 and 45 mL/min. An inflation pressure to inflate the balloon is proportional to the flow rate.

In an embodiment, the catheter includes an ultrasound transducer mounted on the catheter shaft within an interior of the balloon. The ultrasound transducer is surrounded by the working section of the balloon.

In an embodiment, the catheter includes a distal centering mechanism mounted on the catheter shaft distal to the balloon, and a proximal centering mechanism mounted on the catheter shaft proximal to the balloon.

In an embodiment, a method includes advancing a distal region of a catheter into a target vessel having a vessel wall.

The distal region includes a balloon mounted on a catheter shaft. The balloon includes a balloon wall having a distal mounting section, a proximal mounting section, and several shoulders connecting the distal mounting section and the proximal mounting section to a working section. The working section and the several shoulders meet at round corners such that, when the balloon is inflated within the target vessel, the catheter shaft remains centered in the target vessel. The method includes inflating the balloon against the vessel wall. The method includes delivering ultrasonic energy from the transducer to the vessel wall.

In an embodiment, the balloon wall is formed from a urethane material.

In an embodiment, the urethane material has a Shore D durometer in a range of 50 to 60.

In an embodiment, inflating the balloon includes circulating fluid within the balloon based on a lumen diameter of the target vessel.

In an embodiment, inflating the balloon includes inflating the balloon to a predetermined inflation pressure regardless of a lumen diameter of the target vessel. The target vessel constrains the balloon.

In an embodiment, the constrained balloon includes several wrinkles at the vessel wall.

In an embodiment, a method of treating a target tissue from a target vessel includes measuring a size of the target vessel, and advancing a catheter of a tissue treatment system into the target vessel having a vessel wall. The catheter includes a catheter shaft having a fluid channel, an ultrasound transducer, and a compliant balloon mounted on the catheter shaft and having an interior in fluid communication with the fluid channel and containing the ultrasound transducer. The compliant balloon includes a balloon wall having a working section radially surrounding the ultrasound transducer. The method includes inflating the compliant balloon based upon the size of the target vessel such that a substantial portion of the working section of the balloon contacts the vessel wall and the ultrasound transducer is centered within the target vessel. The method includes delivering ultrasonic energy from the ultrasound transducer to the target tissue based upon the size of the target vessel. The balloon is configured to have a predetermined straightness in the working section when the balloon is inflated in a free space from a first diameter to a second diameter 2 mm larger than the first diameter.

In an embodiment, a method of treating a target tissue includes measuring the size of the target vessel is after advancing the catheter.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A catheter, comprising:
a catheter shaft having a fluid channel;
an ultrasound transducer; and
a compliant balloon mounted on the catheter shaft and having an interior in fluid communication with the fluid channel and containing the ultrasound transducer, wherein the compliant balloon includes a balloon wall having a working section radially surrounding the ultrasound transducer, and wherein, the working section has a predetermined straightness both when the working section has a first diameter and when the working section has a second diameter that is at least 2 mm greater than the first diameter, wherein the predetermined straightness includes a cylindricity of the working section being less than 1 mm.

2. The catheter of claim 1, wherein the first diameter is within a range of 3.5 to 6 mm, and wherein the second diameter is within a range of 8 to 9 mm.

3. The catheter of claim 2, wherein the first diameter is 5 mm, and wherein the second diameter is 8.5 mm.

4. The catheter of claim 1, wherein the predetermined straightness includes a ratio of a radius of curvature of the working section to a length of the compliant balloon being greater than 1.

5. The catheter of claim 1, wherein the predetermined straightness includes a first radius of curvature of the working section when the working section has the first diameter being within 20% of a second radius of curvature of the working section when the working section has the second diameter.

6. The catheter of claim 1, wherein the compliant balloon has a first inflation pressure of 2 psi to 10 psi when the working section has the first diameter, and wherein the compliant balloon has a second inflation pressure of 10 to 30 psi when the working section has the second diameter.

7. The catheter of claim 6, wherein, when the compliant balloon is inflated to the second inflation pressure five times, a fourth diameter of the working section when being inflated a fourth time is within 10% of a fifth diameter of the working section when being inflated a fifth time.

8. The catheter of claim 6, wherein, when the compliant balloon has the second inflation pressure, the ultrasound transducer is radially centered within the compliant balloon.

9. The catheter of claim 6, wherein fluid is circulated through the interior at a flow rate of 15 to 35 mL/min to inflate the compliant balloon to the first inflation pressure.

10. The catheter of claim 1, wherein the balloon wall includes a proximal shoulder proximal to the working section, and a distal shoulder distal to the working section, and wherein the proximal shoulder and the distal shoulder are rounded.

11. The catheter of claim 10, wherein the proximal shoulder and the distal shoulder include a plurality of longitudinal ribs.

12. The catheter of claim 10, wherein the balloon wall is thicker at the proximal shoulder and the distal shoulder than at the working section.

13. The catheter of claim 1, wherein the compliant balloon is formed from an elastomeric material.

14. The catheter of claim 13, wherein the elastomeric material includes a polyether-based thermoplastic polyurethane.

15. The catheter of claim 14, wherein the polyether-based thermoplastic polyurethane has a Shore D durometer in a range of 50 to 60.

16. The catheter of claim 15, wherein the polyether-based thermoplastic polyurethane has a Shore D durometer of 55.

17. The catheter of claim 16, wherein the working section of the balloon wall has a double wall thickness of 0.0004 inch to 0.0014 inch.

18. The catheter of claim 17, wherein the compliant balloon is configured to treat a blood vessel having a vessel lumen diameter between 3 mm to 9 mm in diameter.

19. The catheter of claim 1, wherein the balloon wall includes no foreign particles or bubbles greater than 0.2 mm².

20. The catheter of claim 1, wherein the working section of the balloon wall has a double wall thickness of 0.0004 inch to 0.0014 inch.

21. The catheter of claim 1, wherein the compliant balloon is configured to treat a blood vessel having a vessel lumen diameter between 3 mm to 8 mm in diameter.

22. The catheter of claim 21, wherein the blood vessel is a renal artery.

23. The catheter of claim 1, wherein when the compliant balloon is inflated in free space:

the compliant balloon has a first inflation pressure of 2 psi when the working section has the first diameter, and the compliant balloon has a second inflation pressure of 10 psi when the working section has the second diameter.

24. The catheter of claim 1, wherein the compliant balloon has an inflation pressure of 10 psi or less when the working section has the first diameter and the second diameter.

25. The catheter of claim 1, wherein the compliant balloon has a burst strength of greater than 45 psi.

26. The catheter of claim 1, wherein the working section has a maximum diameter and a minimum diameter over the length of the working section defining the cylindricity of the working section, and wherein the difference between the maximum diameter and a minimum diameter of the working section is less than 1 mm.

27. The catheter of claim 1, wherein the difference between a maximum diameter and a minimum diameter of the working section is less than 0.75 mm.

28. The catheter of claim 1, wherein the difference between a maximum diameter and a minimum diameter of the working section is approximately 0.5 mm when the compliant balloon is inflated to 10 psi.

29. A kit, comprising:

a first catheter including a first catheter shaft having a first compliant balloon mounted on the first catheter shaft and having a first interior in fluid communication with a first fluid channel of the first catheter and containing a first ultrasound transducer, wherein the first compliant balloon has a first inflation diameter range of at least 2 mm when fluid is circulated through the first fluid channel at a first flow rate;

a second catheter including a second catheter shaft having a second compliant balloon mounted on the second catheter shaft and having a second interior in fluid communication with a second fluid channel of the second catheter and containing a second ultrasound transducer, wherein the second compliant balloon has a second inflation diameter range of at least 2 mm when fluid is circulated through the second fluid channel at a second flow rate;

wherein the respective compliant balloons include respective balloon walls having respective working sections radially surrounding the respective ultrasound transducers, and wherein the respective working sections have a predetermined straightness when the respective working sections have the respective inflation diameter ranges;

wherein the first inflation diameter range overlaps the second inflation diameter range, and wherein the predetermined straightness includes a cylindricity of the respective working section being less than 1 mm.

30. The kit of claim 29, wherein the first inflation diameter range is 3 to 5 mm, and wherein the second inflation diameter range is 4 mm to 8 mm.

31. A tissue treatment catheter, comprising:

an elongated catheter shaft extending longitudinally from a proximal end to a distal end, wherein an inlet channel, an outlet channel, electrical cabling, and a guidewire lumen extend through the catheter shaft;

a proximal hub coupled to the proximal end, wherein the hub includes an inlet port coupled to the inlet channel and an outlet port coupled to the outlet channel, and wherein the electrical cabling extends through the proximal hub to a proximal cabling end;

an electrical coupling mounted on the proximal cabling end and configured to receive electrical power from an electrical generator;

an ultrasound transducer mounted on the catheter shaft and electrically connected to the electrical coupling through the electrical cabling; and a compliant balloon mounted on the catheter shaft and having an interior in fluid communication with the inlet channel and the outlet channel, and containing the ultrasound transducer, wherein the compliant balloon includes a balloon wall having a working section radially surrounding the ultrasound transducer, and wherein the working section has a predetermined straightness both when the working section has a first diameter and when the working section has a second diameter that is at least 2 mm greater than the first diameter, wherein the predetermined straightness includes a cylindricity of the working section being less than 1 mm.

32. A catheter, comprising:

a catheter shaft having a fluid channel;

an ultrasound transducer; and a compliant balloon mounted on the catheter shaft and having an interior in fluid communication with the fluid channel and containing the ultrasound transducer, wherein the compliant balloon includes a balloon body having a balloon wall, the balloon wall having a working section radially surrounding the ultrasound transducer, wherein the balloon body has a proximal end, a midpoint, and a distal end, wherein the first diameters of the balloon at the proximal end, a midpoint, and a distal end are approximately the same when the working section has a first diameter, and wherein the second diameters of the balloon at the proximal end, a midpoint, and a distal end are approximately the same when the working section has a second diameter that is at least 2 mm greater than the first diameter of the working section.

33. The catheter of claim 32, wherein the diameters of the balloon at the proximal end, a midpoint, and a distal end are the same within a tolerance of 0.020 inches when the balloon is inflated to 2 atm, 10 atm, or 30 atm.

34. The catheter of claim 32, wherein when the compliant balloon is inflated to a pressure of 10 psi, the maximum deviation in diameter across the working section is approximately 0.5 mm.

35. The catheter of claim 32, wherein the balloon wall includes a proximal shoulder proximal to the working section, and a distal shoulder distal to the working section, and wherein the proximal shoulder and the distal shoulder are configured to transition from angular to rounded when the balloon pressure increases.

36. The catheter of claim 32, wherein the balloon wall includes a proximal shoulder proximal to the working section, and a distal shoulder distal to the working section, wherein the proximal shoulder and the distal shoulder are angular when the compliant balloon is inflated to a native balloon pressure, and wherein the proximal shoulder and the distal shoulder are configured to round when the balloon pressure increases above the native balloon pressure.

* * * * *